United States Patent
Erdogan et al.

(10) Patent No.: US 7,123,416 B1
(45) Date of Patent: *Oct. 17, 2006

(54) METHOD OF MAKING HIGH PERFORMANCE OPTICAL EDGE AND NOTCH FILTERS AND RESULTING PRODUCTS

(75) Inventors: Turan Erdogan, Spencerport, NY (US); Joseph T. Foss, Rochester, NY (US); Ligang Wang, Rochester, NY (US)

(73) Assignee: Semrock, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/248,456

(22) Filed: Oct. 11, 2005

Related U.S. Application Data

(63) Continuation-in-part of application No. 10/840,134, filed on May 6, 2004.

(60) Provisional application No. 60/637,697, filed on Dec. 21, 2004, provisional application No. 60/468,245, filed on May 6, 2003.

(51) Int. Cl.
    *G02B 5/28* (2006.01)
    *G02B 1/10* (2006.01)

(52) U.S. Cl. .................. 359/589; 359/588; 359/580; 359/587

(58) Field of Classification Search ................ 359/589, 359/588, 580, 587
    See application file for complete search history.

(56) References Cited

U.S. PATENT DOCUMENTS

| | | | |
|---|---|---|---|
| 4,142,958 A | 3/1979 | Wei et al. | |
| 4,793,908 A | 12/1988 | Scott et al. | |
| 5,112,127 A | 5/1992 | Carrabba et al. | |
| 5,512,131 A | 4/1996 | Kumar et al. | |
| 5,656,138 A | 8/1997 | Scobey et al. | |
| 5,712,715 A | 1/1998 | Erdogan et al. | |
| 5,828,489 A * | 10/1998 | Johnson et al. | ............. 359/487 |
| 5,900,160 A | 5/1999 | Whitesides et al. | |
| 6,518,168 B1 | 2/2003 | Clem et al. | |
| 6,623,803 B1 | 9/2003 | Krivokapic | |
| 6,649,208 B1 | 11/2003 | Rodgers | |
| 6,704,130 B1 | 3/2004 | Ford et al. | |
| 6,809,859 B1 | 10/2004 | Erdogan et al. | |
| 2005/0110999 A1 | 5/2005 | Erdogan et al. | |

OTHER PUBLICATIONS

Becker, J., "Ion-Beam Sputtering," Handbook of Optical Properties, vol. 1, Thin Films for Optical Coatings, Ed. By R.E. Hummel and K.H. Guenther, Chapter 7, pp. 189-211, (CRC Press, Boca Raton, 1995).

Macleod, H. Angus, "Thin-Film Optical Filters," 3rd Ed., Institute of Physics (2001).

(Continued)

*Primary Examiner*—Fayez G. Assaf
(74) *Attorney, Agent, or Firm*—Lowenstein Sandler PC

(57) ABSTRACT

High performance optical edge and notch filters and methods of making the same are disclosed. The multi-layer, thin-film optical edge filters have an edge steepness greater than about 0.8% as measured by dividing (a) the edge width from the 50% transmission wavelength to the optical density 6 ("OD6") wavelength by (b) the 50% transmission wavelength. The optical edge filters also have an average transmission above about 95%. The notch filters exhibit a blocking of OD>6, very high transmission (>90%) outside the notch(es), and a narrow notch bandwidth comparable to that of holographic notch filters. The methods for making such filters accurately determine when deposition of each layer of the filter should terminate.

53 Claims, 18 Drawing Sheets

OTHER PUBLICATIONS

Macleod, H. Angus, "Turning value monitoring of narrow-band all-dielectric thin-film optical filters," Optica Acta, vol. 19, pp. 1-28 (1972).

Press, W.H., et al., The Levenberg-Marquardt method implemented under the name "mrqmin( )", *Numerical Recipes in C: The Art of Scientific Computing*, 2nd ed., Chapter 15, pp. 683-688 (1995).

Martin, P.J. et al., "Ion-beam-assisted deposition of thin films," Applied Optics, vol. 22, No. 1, pp. 178-184 (1983).

"Interference Filters," Melles Griot, pp. 13.25-13.29.

J.M.E. Harper, "Ion Beam Deposition," In *Thin Film Processes*, Ed. by J.L. Vossen and W. Kern, pp. 175-206 (Academic Press, New York, 1978).

U.J. Gibson, "Ion-Beam Processing of Optical Thin Films," in *Physics of Thin Films*, vol. 13, Ed. by G. Hass and M.H. Fancombe, pp. 109-150 (Academic Press, New York, 1978).

J.M.E. Harper et al., "Modification of Thin Film Properties by Ion Bombardment During Deposition," in *Ion Bombardment Modification of Surfaces*, Ed. by O. Auciello and R. Kelly, from *Beam Modification of Materials*, vol. 1, pp. 127-162 (Elsevier, Amsterdam, 1984).

W.H. Press et al., *Numerical Recipes*, "Numerical Recipes in C: The Art of Scientific Computing," 2nd ed., Cambridge University Press, Cambridge, Chapter 15.7, pp. 699-706 (1995).

\* cited by examiner

Fig. 10 - LWP
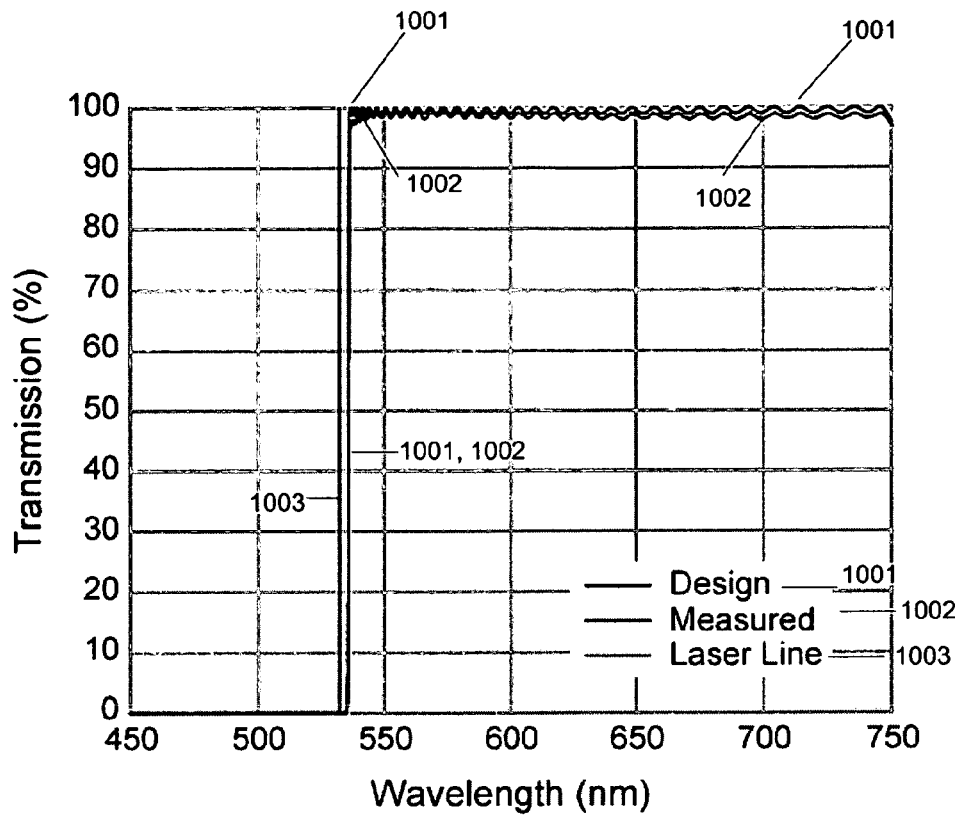
Fig. 11 - LWP
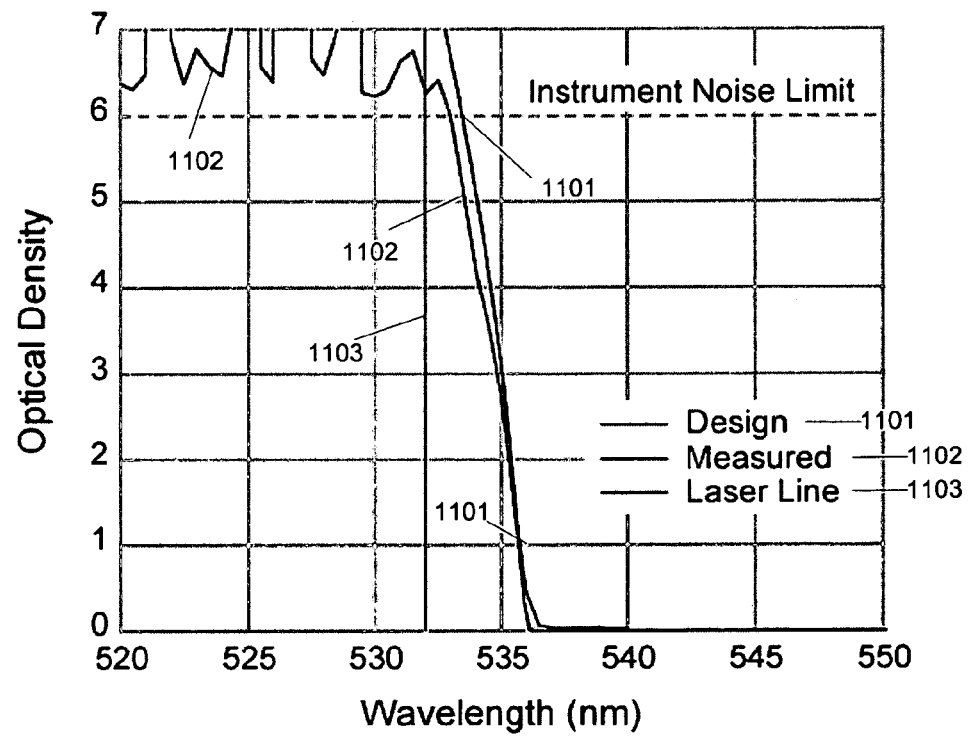

Fig. 12 - SWP
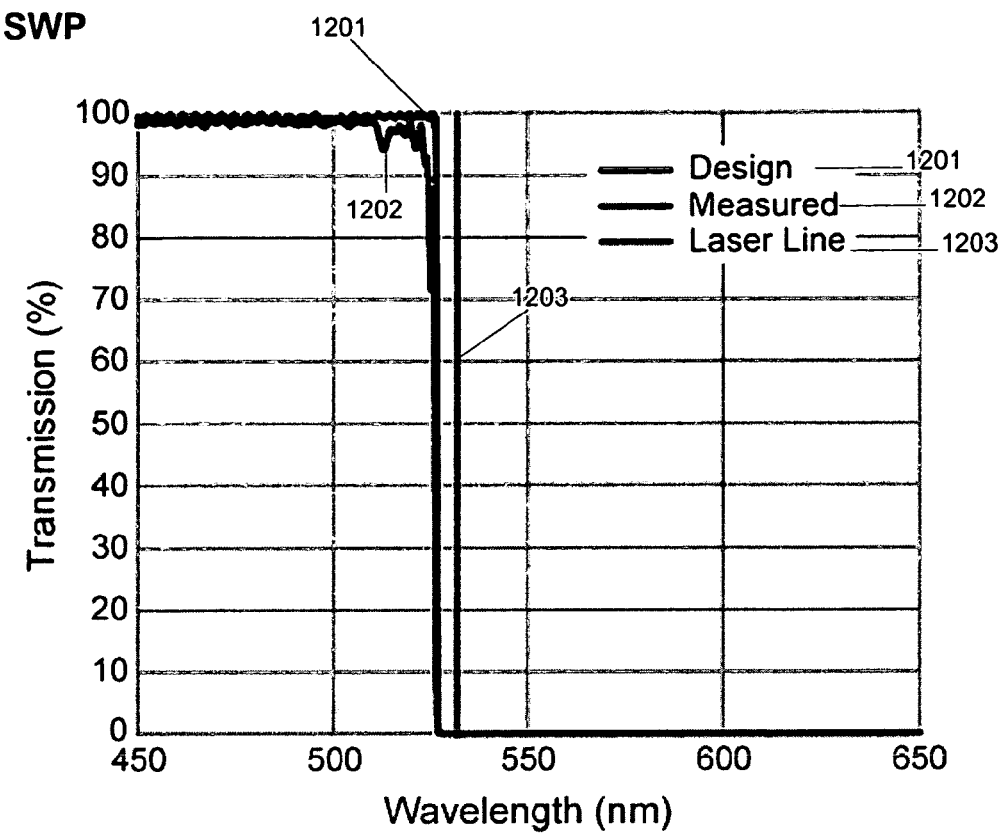
Fig. 13 - SWP
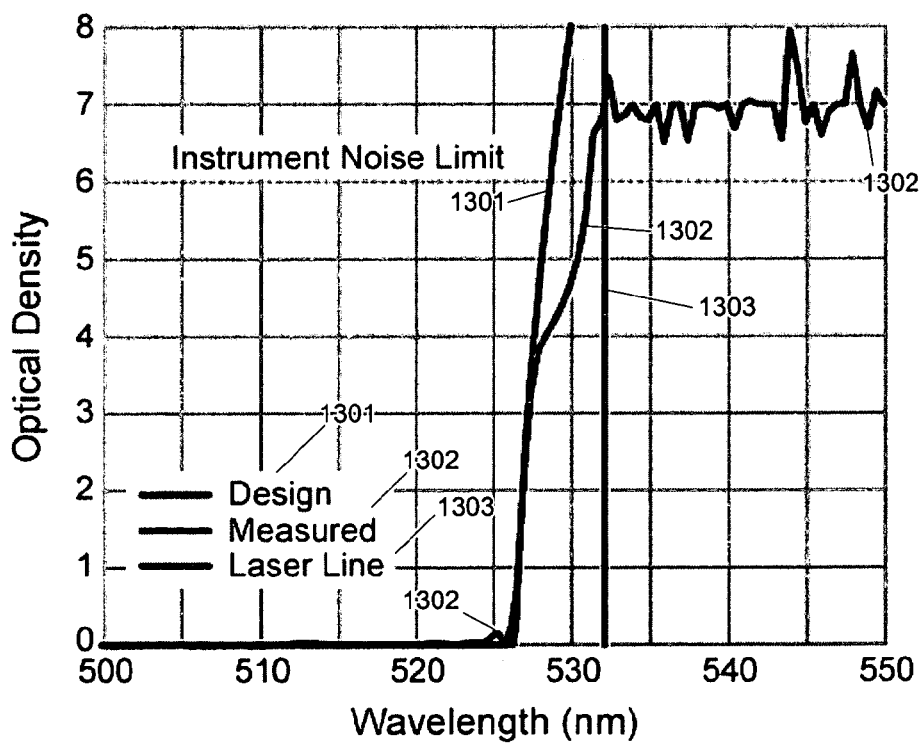

Fig. 14 [633 nm single-notch filter example]
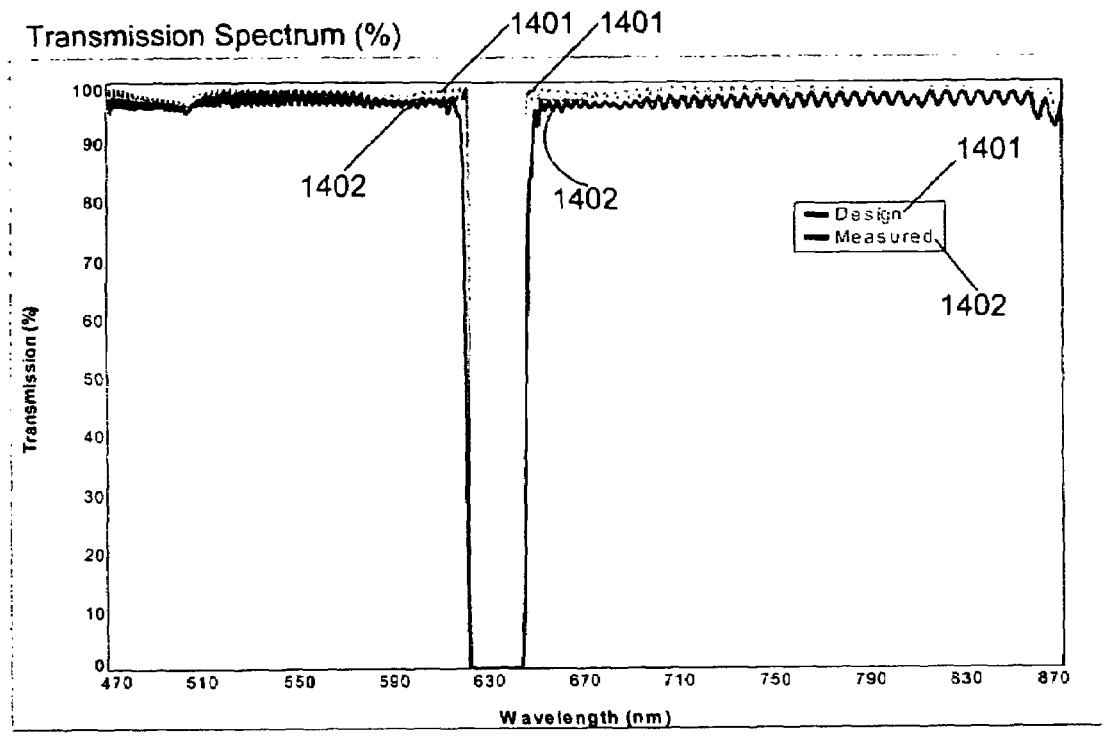
Fig. 15
Optical Density (OD) Spectrum
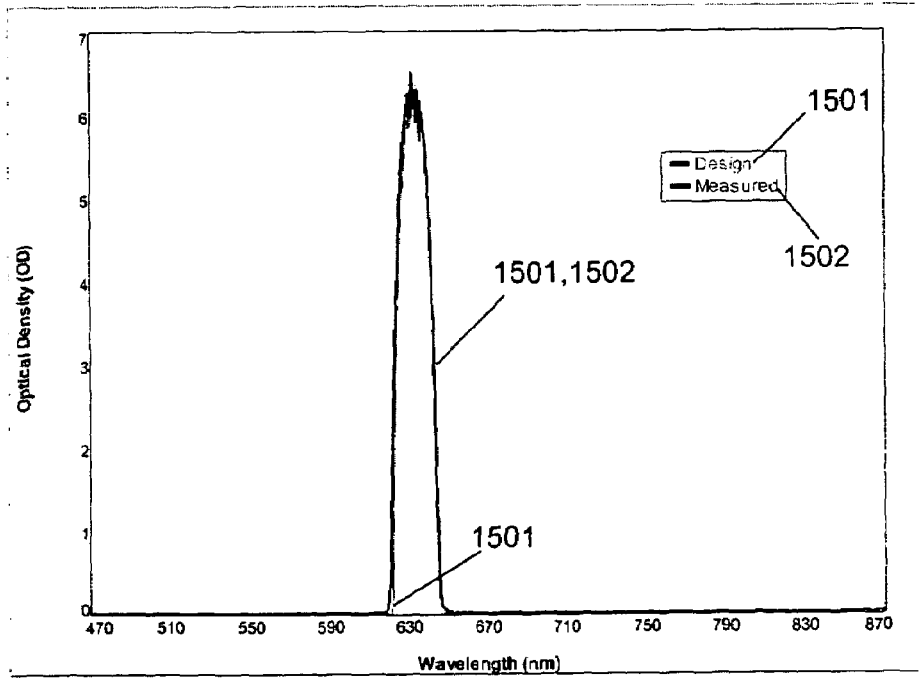

Fig. 16 [Triple-notch filter (triple-notch in a single coating)]
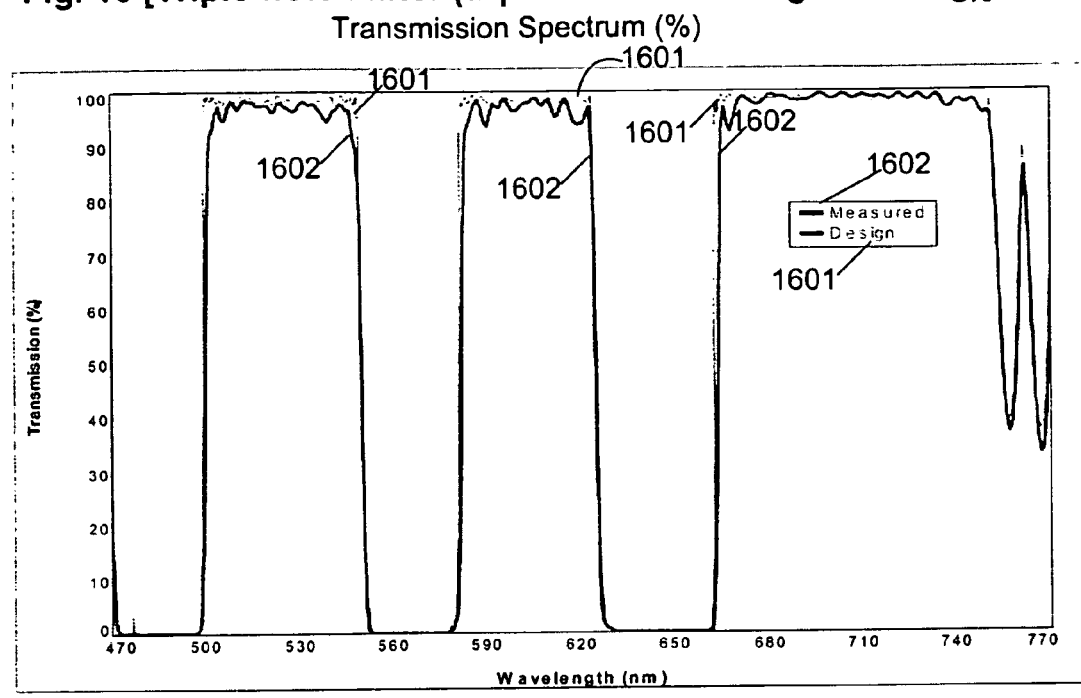
Fig. 17
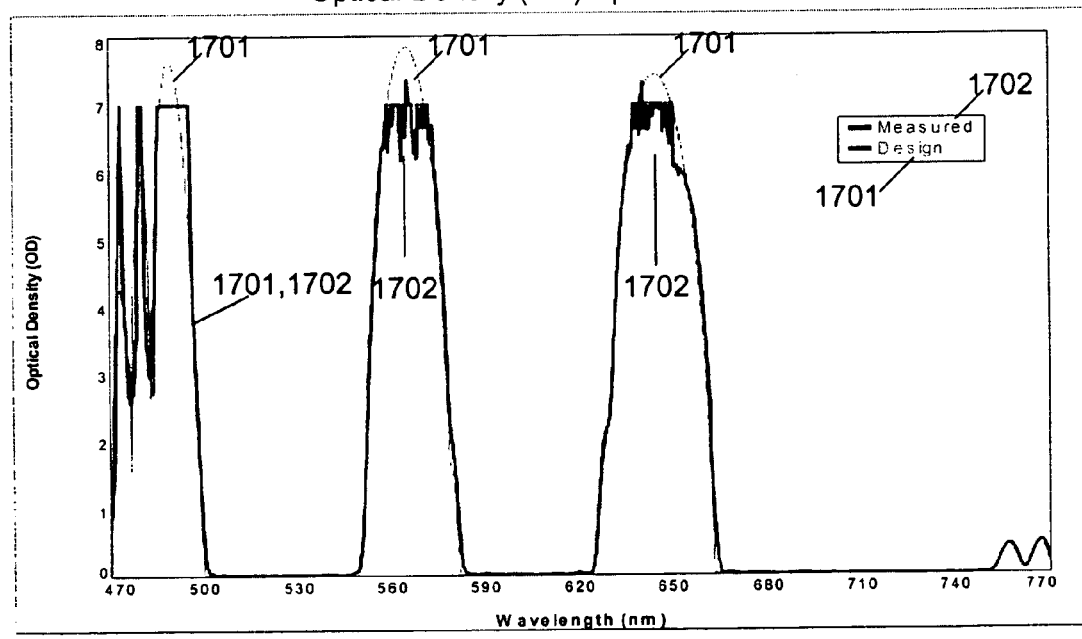

Fig. 18 [Triple-notch filter example 2 (dual-notch plus LWP)]
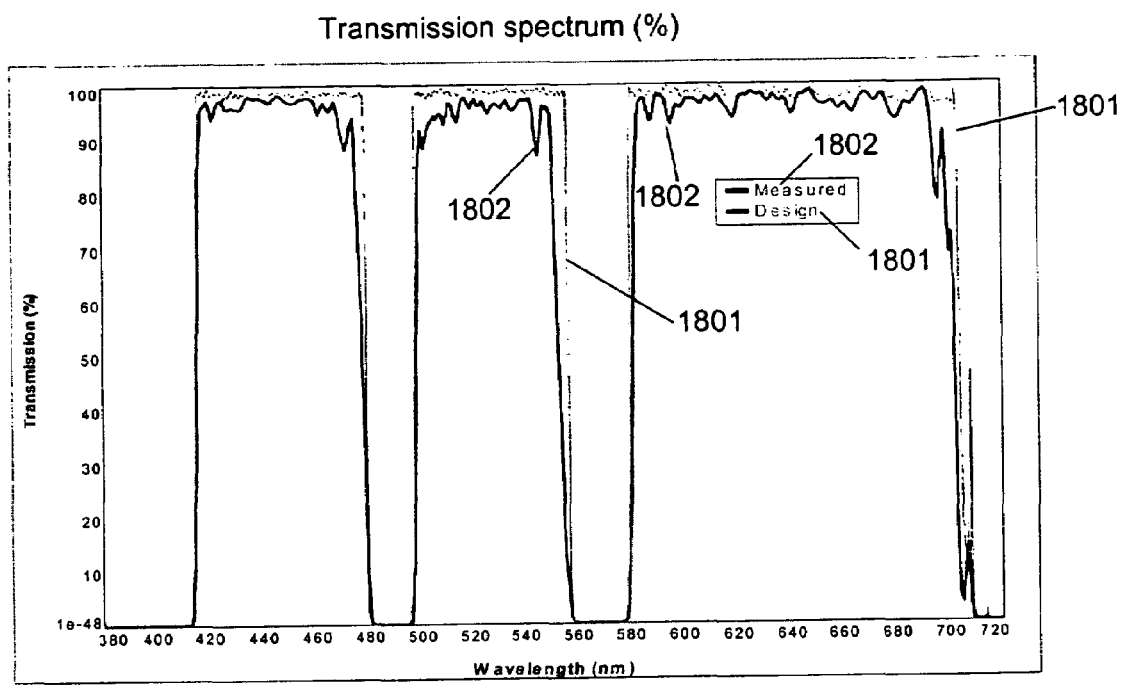
Fig. 19
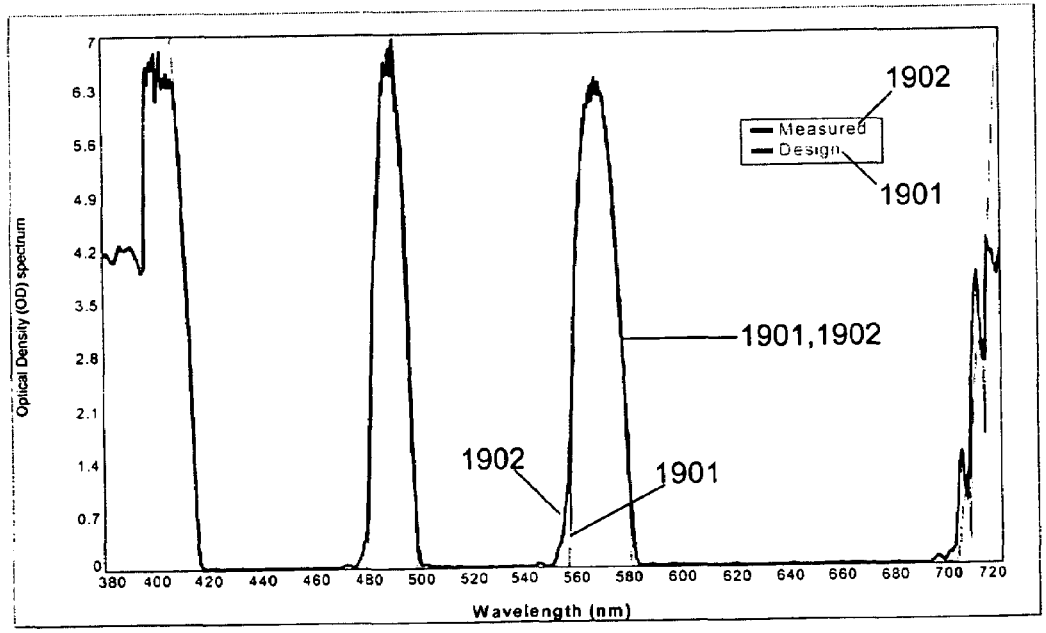

Fig. 20 [Triple-notch filter example 2 - Continued]
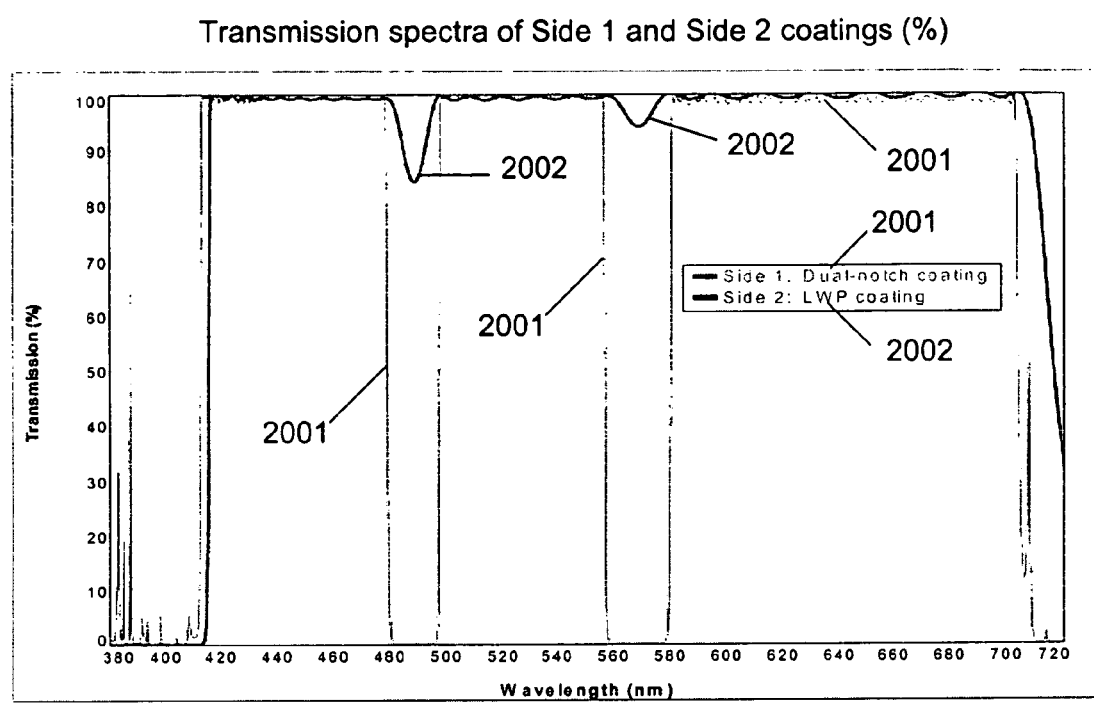

Fig. 21 [45 degree single-notch filter example]
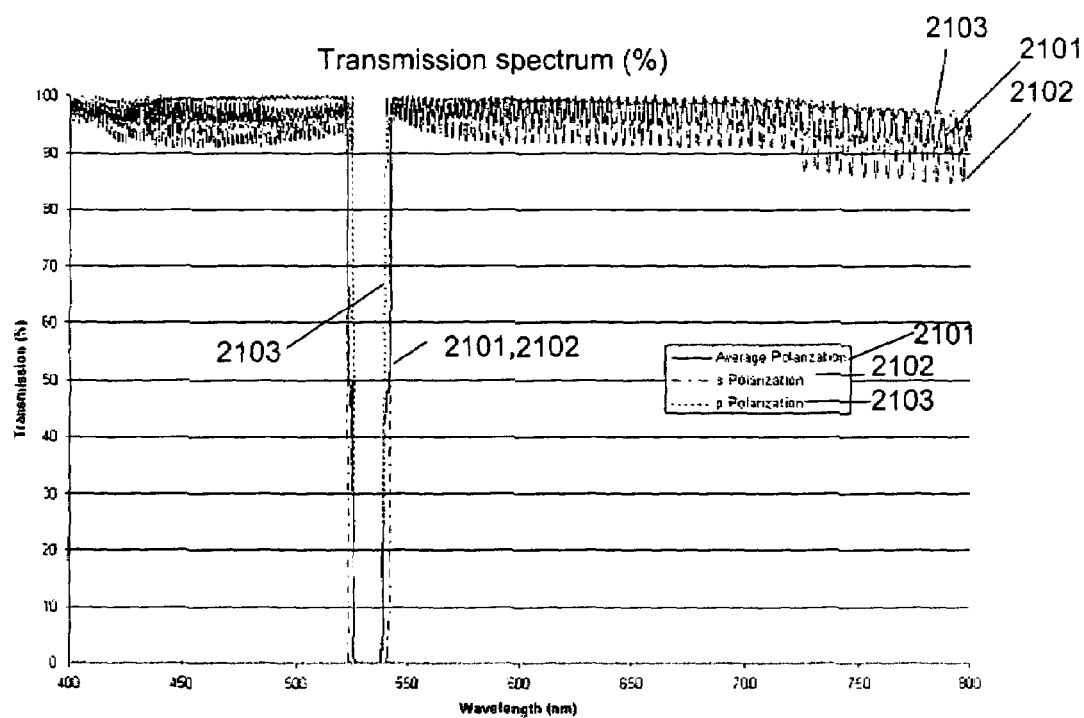

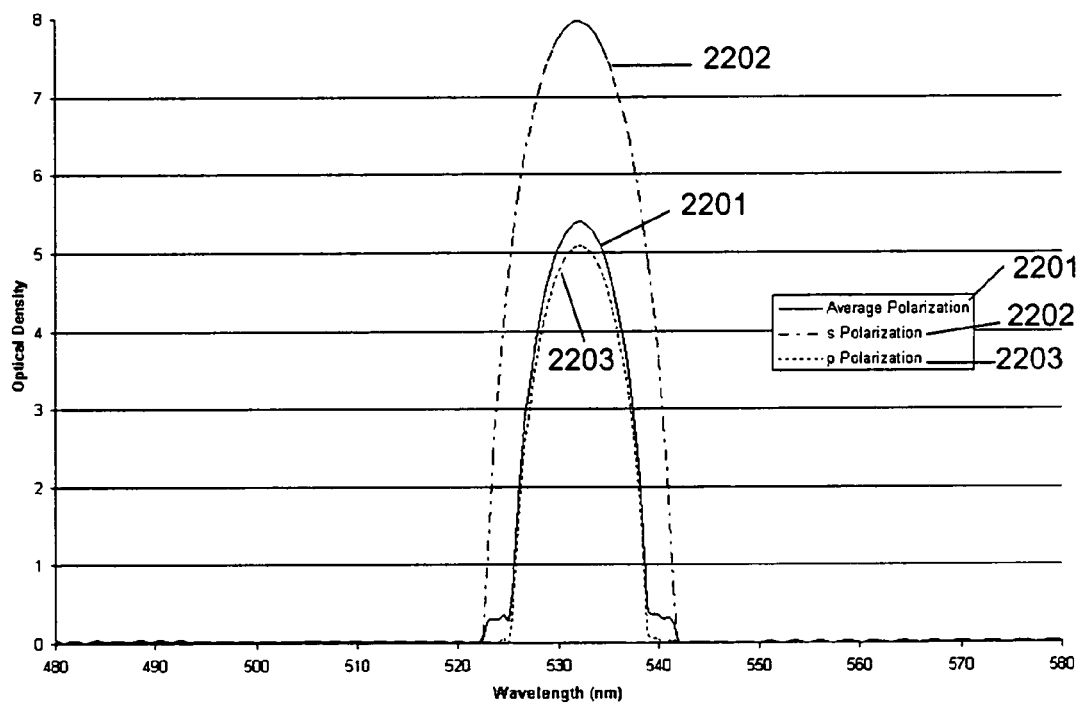
Fig. 22 [45 degree single-notch filter example continued]

Fig. 23 [Quadruple-notch filter]
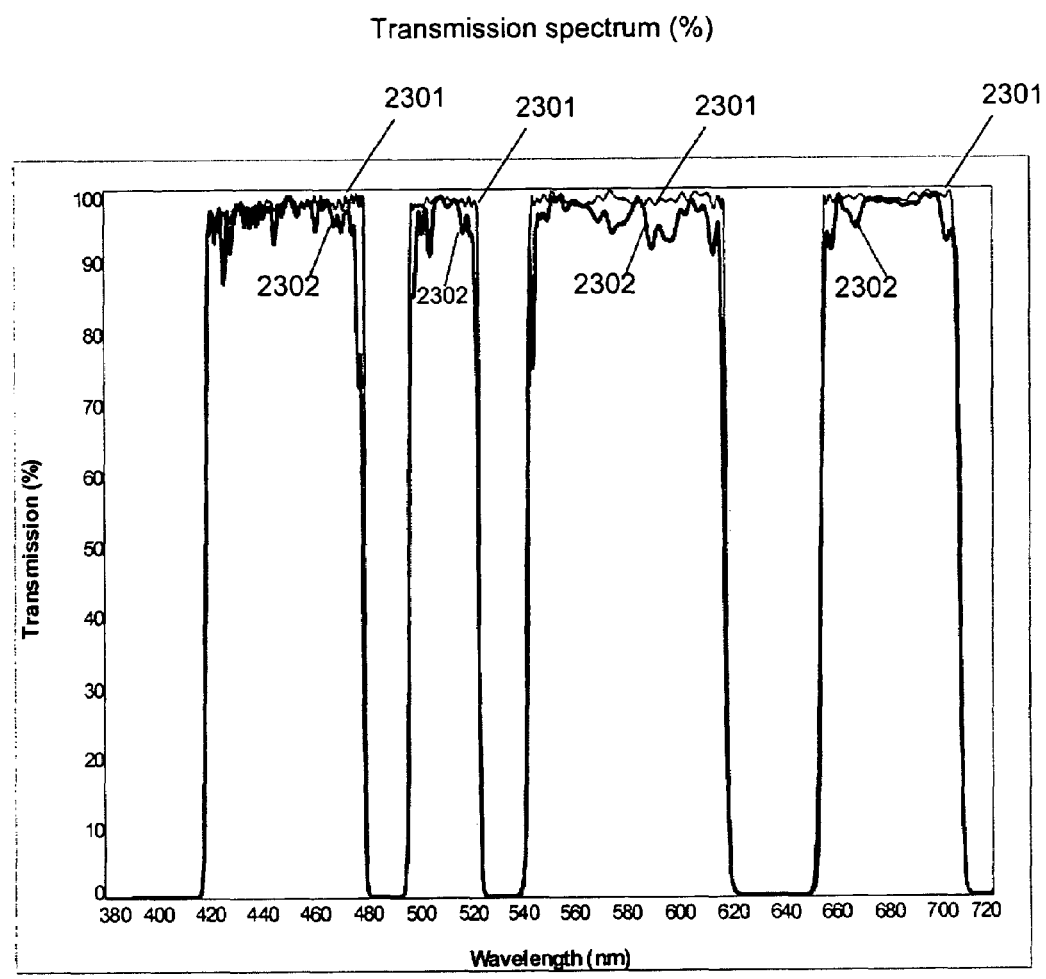

Fig. 24 [Quadruple-notch filter]
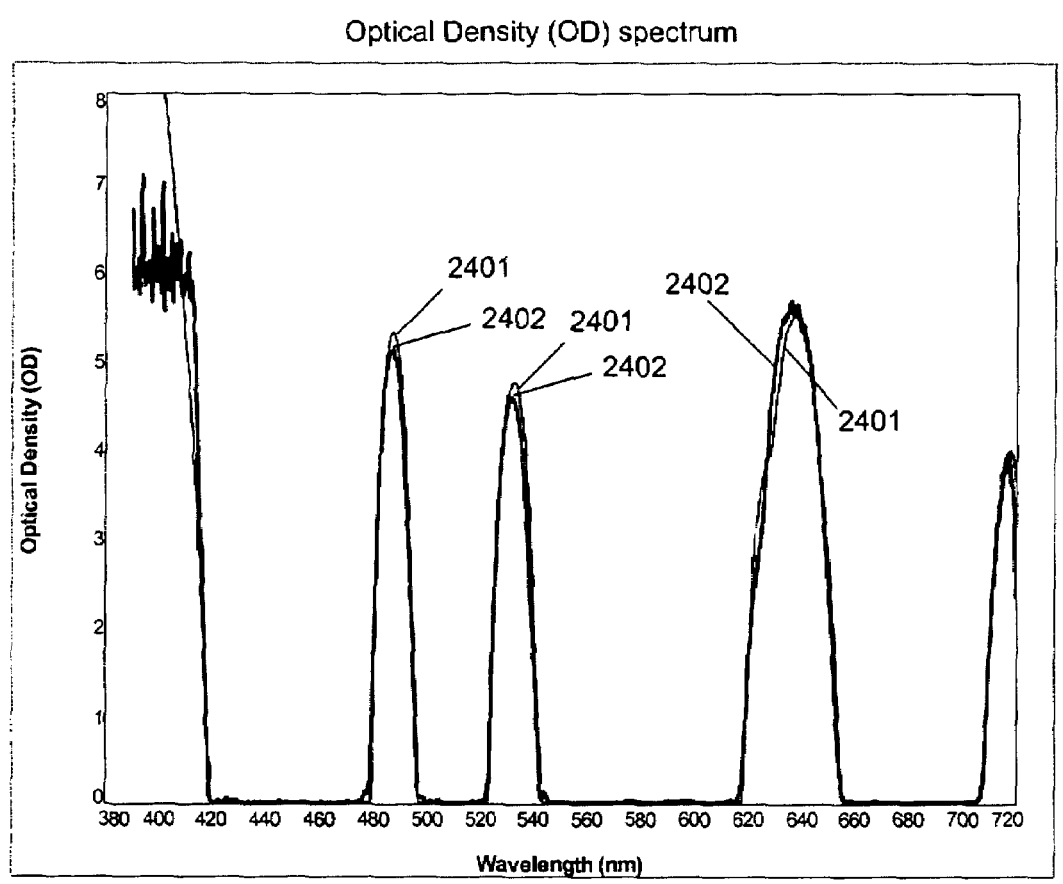

US 7,123,416 B1

METHOD OF MAKING HIGH PERFORMANCE OPTICAL EDGE AND NOTCH FILTERS AND RESULTING PRODUCTS

CROSS REFERENCE TO RELATED APPLICATIONS

This application claims the benefit of U.S. Provisional Application No. 60/637,697, titled High Performance Thin Film Notch Filters, filed on Dec. 21, 2004 by Turan Erdogan, Joseph T. Foss, and Ligang Wang, and is a continuation-in-part of prior U.S. patent application Ser. No. 10/840,134, filed May 6, 2004, which claims the benefit of U.S. Provisional Application Ser. No. 60/468,245, filed May 6, 2003. The entire disclosures of U.S. Provisional Application No. 60/637,697, U.S. patent application Ser. No. 10/840,134, and U.S. Provisional Application No. 60/468,245 are hereby incorporated herein by reference.

FIELD OF INVENTION

This invention relates to methods of making optical edge filters and optical notch filters and also relates to the resulting improved filters.

BACKGROUND OF THE INVENTION

A. Optical Edge Filters, Optical Notch Filters, and Their use

Optical edge filters and thin-film notch filters are important components in systems for optical measurement and analysis including Raman spectroscopy and fluorescence spectroscopy. Optical edge filters and/or notch filters are used in such systems to block unwanted light that would otherwise constitute or generate spurious optical signals and swamp the signals to be detected and analyzed.

Optical edge filters block unwanted light having wavelengths above or, alternatively, below a chosen "transition" wavelength $\lambda_T$ while transmitting light on the unblocked side of $\lambda_T$. Edge filters which transmit optical wavelengths longer than $\lambda_T$ are called long-wave-pass filters (LWP filters), and edge filters which transmit wavelengths shorter than $\lambda_T$ are short-wave-pass or SWP filters.

Referring to the drawings, FIGS. 1A and 1B schematically illustrate the spectral transmission of idealized long-wave-pass and short-wave-pass filters respectively. As can be seen from FIG. 1A, a LWP filter blocks light with wavelengths below $\lambda_T$ and transmits light with wavelengths above $\lambda_T$. As shown in FIG. 1B, a SWP filter transmits light with wavelengths below $\lambda_T$ and blocks light with wavelengths above $\lambda_T$. $\lambda_T$ is the wavelength at which the filter "transitions" from blocking to transmission, or vice versa.

While an ideal edge filter has a precise transition wavelength $\lambda_T$ represented by a vertical line at $\lambda_T$, real edge filters change from blocking to transmission over a small range of wavelengths and are more accurately represented by a non-vertical but steeply sloped line near $\lambda_T$. Similarly, while an ideal edge filter transmits all light in the transmission region (transmission T=1), real filters invariably block a small portion of the light to be transmitted (T<1). The steepness of the line and the proportion of the light transmitted are important parameters in many applications.

Turning now to FIGS. 1C and 1D, the spectral transmission of an ideal and a realistic notch filter are illustrated respectively. Notch filters block a specific and narrow range of wavelengths (ideally a single laser "line" $\lambda_L$) and pass light with high transmission on both sides of the narrow blocking range. Because lasers emit a very small, but non-zero, bandwidth of light, an ideal notch filter blocks light at wavelengths within this bandwidth (($\lambda_L-(BW/2)$) to ($\lambda_L+(BW/2)$)) with no ripple and perfectly steep (vertical) transition edges, as shown in FIG. 1C. The ideal notch filter passes light at wavelengths longer than the blocking band ($\lambda>(\lambda_L+(BW/2))$) and passes light at wavelengths shorter than the blocking band ($\lambda<(\lambda_L-(BW/2))$). A realistic notch filter does not have complete transmission outside of the blocking band (($\lambda_L-(BW/2)$) to ($\lambda_L+(BW/2)$)), does not completely block radiation within the blocking band, and has non-vertical transition edges, thereby changing from blocking to transmission over a small range of wavelengths, as shown in FIG. 1D. Accordingly, the steepness of the edges, the transmission amount outside of the blocking band, and the blocking effectiveness within the blocking band are important parameters of notch filters in many applications.

Edge filters and notch filters are particularly useful in optical measurement and analysis systems that use laser light to excite a sample at one wavelength (or a small band of wavelengths) $\lambda_L$ and measure or view an optical response of the excited sample at other wavelengths. The excitation light $\lambda_L$ is delivered to the sample by an excitation light path, and the optical response of the sample is delivered to the eye or measuring instrument by a collection path. Edge filters can be used to block spurious light from the excitation path. Edge filters and/or notch filters can be used to block excitation light from entry into the collection path. The steeper the filter edge(s), the more effectively spurious signals are blocked. In the case of both edge filters and notch filters, the lower the transmission loss, the more light from the sample reaches the measuring instrument.

Raman spectroscopy is one such optical analysis system. It is based on the fact that when molecular material is irradiated with high intensity light of a given wavelength (or series of wavelengths) $\lambda_L$, a small portion of the incident light scattered by the material will be shifted in wavelength above and below $\lambda_L$. This Raman shifting is attributed to the interaction of the light with resonant molecular structures within the material, and the spectral distribution of the Raman-shifted light provides a spectral "fingerprint" characteristic of the composition of the material. As a practical example, a Raman probe can identify the contents of a bottle without opening the bottle.

FIG. 2 is a simplified schematic diagram of a Raman probe 20. In essence, the probe 20 comprises an optical excitation path 22, and a collection path 23. These paths advantageously comprise optical fiber. In operation, excitation light $\lambda_L$ from a laser 24 passes through the fiber path 22 and one or more edge filters or a narrowband laser-line filter 22A to illuminate a portion of the sample 21 with high intensity light. The edge filter(s)/laser-line filter 22A act(s) to block light outside of $\lambda_L$ from the sample 21. Light scattered from the sample 21 passes through a notch filter (or one or more edge filters) 23A and then through fiber collection path 23 to a spectral analyzer 25 where the "fingerprint" of the sample is determined.

The light scattered from the sample 21 is a mixture of unshifted scattered excitation light $\lambda_L$ Rayleigh scattering) and Raman-shifted light at wavelengths longer and shorter than $\lambda_L$. The scattered excitation light $\lambda_L$ would not only swamp the analyzer, it would also excite spurious Raman scattering in a collection fiber. Thus the unshifted excitation light $\lambda_L$ should be removed from the collection path. This can be accomplished by disposing a notch filter (or one or more edge filters) 23A between the sample 21 and the collection fiber 23, the notch filter (or edge filter(s)) 23A blocking the unshifted scattered excitation light $\lambda_L$.

Edge filters and notch filters also are useful in fluorescence spectroscopy. Here, laser excitation light $\lambda_L$ is used to excite longer wavelength emissions from fluorescent markers. The markers can be fluorescent atoms chemically bonded to a biological molecule to track the molecule in a body or cell. Edge filters may be used to reject spurious light from an excitation path and to reject excitation light from a collection path. Notch filters may be used to reject excitation light from the collection path.

In the case of edge filters, it should now be clear that the steeper the filter slope at the transition wavelength $\lambda_T$, the greater the amount of spurious light that can be filtered out. In addition, the steeper the slope, the greater the amount of shifted light from the sample that will reach the analyzer. Similarly, higher levels of transmission of the shifted light through the filters provide more light for analysis. Higher edge filter blocking provides better rejection of the laser excitation light from the spectrum analyzer, thus decreasing the noise and improving both specificity and sensitivity of the measurement. Higher edge-filter transmission enables the maximum signal to reach the analyzer, further improving the signal-to-noise ratio and hence the measurement or image fidelity. A steeper filter edge also permits shifts to be resolved much closer to the excitation wavelength, thus increasing the amount of information from the measurement.

In the case of notch filters, the steeper the edges of the notch filter at the laser wavelength $\lambda_L$, the greater the amount of unshifted excitation light $\lambda_L$ that can be filtered out before reaching an analyzer. Similarly, the higher the levels of transmission outside of the blocking band, the more information there is for measurement.

B. Edge Filter and Notch Filter Structure and Conventional Fabrication

FIG. 3 is a simplified schematic illustration of an optical filter 30, which may be either an edge filter or a notch filter. The optical filter 30 comprises a transparent substrate 31 having a flat major surface 32 supporting many thin coatings 33A, 33B. The thickness of the coatings is exaggerated and the number is reduced for purposes of illustration. Coatings 33A and 33B are typically alternating and of different respective materials chosen to present markedly different indices of refraction (index contrast). The coating indices and thicknesses are chosen and dimensioned to filter impinging light by interference effects in a desired manner. Specifically, if a light beam 34 impinges on the filter, a first wavelength portion 34T of a beam is transmitted and a second wavelength portion 34R is reflected and thus rejected by the filter. What is transmitted and what is reflected depends on the precise thicknesses and indices of the thin coatings.

Two basic types of thin-film edge filters and thin-film notch filters exist: those based on "soft coatings" and those based on "hard coatings," both of which are typically manufactured by an evaporation technique (either thermal evaporation or electron-beam evaporation). Hard coating filters, however, may also be manufactured by non-evaporative techniques such as ion-beam sputtering.

Soft coatings imply literally what the name suggests-they are physically soft and can be readily scratched or damaged. They are fairly porous, which also means they tend to be hygroscopic (absorb water vapor) leading to dynamic changes in the film index and hence the resulting filter spectrum in correlation to local humidity. There are two main reasons soft coatings are used. First, an advantageous larger index contrast can be realized with soft coatings. (The index contrast is the relative difference between the index of refraction of the low-index material and that of the high-index material.) For example, many high-performance soft-coated filters are made using sodium aluminum fluoride ("cryolite"), with a chemical composition of $Na_3AlF_6$ and an index of about 1.35 for visible wavelengths, and zinc sulfide, with a chemical composition of ZnS and an index of about 2.35. The second reason for using these materials is that the evaporation process can be controlled well for these materials, largely because they have relatively low melting temperatures. Hence it is possible to maintain fairly accurate control over the layer thicknesses even for filter structures with many tens of layers and perhaps even up to 100 layers. As described above, edge filter performance is measured by edge steepness, depth of blocking, and high transmission with low ripple. A larger index contrast and a larger number of layers both yield more steepness and more blocking. High transmission with low ripple is improved with more layers and higher layer thickness accuracy. For these reasons the highest performance conventional thin-film edge filters have been made with soft-coating technology.

Hard coatings are made with tougher materials (generally oxides), and result from "energetic" deposition processes, in which energy is explicitly supplied to the film itself during the deposition process. This is accomplished with a beam of ions impinging directly on the coating surface. The ion bombardment acts to "hammer" the atoms into place in a more dense, less porous film structure. Such processes are usually called ion-assisted deposition (IAD) processes. High-performance edge filters have been made with ion-assisted electron-beam evaporation. Typically the index contrast available with hard-coating (oxide) thin-film materials is not as high as that of the soft-coating materials, and consequently more layers must be deposited to achieve a comparable level of performance. This problem, coupled with the more difficult to control deposition rates and overall processes of high-melting-temperature oxides, leads to much more stringent requirements on the layer-thickness control techniques to achieve a reasonable level of layer thickness accuracy for good edge steepness and high, low-ripple transmission.

For the best filters, some kind of "optical monitoring" (direct measurement of filter transmission or reflection during deposition) is necessary to determine when to terminate the deposition of each layer. Optical monitoring can be performed on the actual filters of interest or on "witness pieces" often positioned in the center of the deposition chamber. There are three basic types of optical monitoring algorithms. The first is often called "drop-chip" monitoring, and is based on measuring the transmission (or reflection) vs. time through a new witness piece for each new layer. Since the theoretical transmission vs. time can be calculated accurately for each layer deposited on a blank piece of glass, then a good comparison between the measured and theory curves can be made independent of the history of the deposition (thickness errors in previous layers). This technique is accurate and useful for layers of arbitrary thickness, but it is cumbersome, especially for filters comprised of at least many 10's of layers.

The second type of monitoring is called "turning-point" monitoring, and is used for depositing layers that are precisely a quarter of a wavelength in thickness (or multiples thereof). The technique is based on the fact that the transmission vs. time reaches a turning point (or extremum) at each multiple of a quarter wave of thickness, so an algorithm is developed to cut layers precisely at the turning points. The elegant feature of this method is that there is inherent compensation for layer thickness errors from previous layers, so long as one adheres to the rule of cutting exactly at turning points. It thus works extremely well even for very thick coatings with even hundreds layers (it is the basis for manufacturing very high-performance filters for DWDM telecom applications, which can have as many as 200–400 quarter-wave layers).

The third type of monitoring is called "level monitoring," and is applicable for non-quarter-wave thick layers. Monitoring can be done through the actual filters or through witness piece(s). The concept is to cut layers at predetermined transmission levels, based on a calculated prediction of transmission vs. time for the entire structure. However, because small layer errors lead to large variations in the absolute transmission values, one must instead rely on cutting at the correct transmission level relative to the local maximum and minimum values. Hence the method works well only for non-quarter-wave thick layers that are more than a half-wave thick, so that there is both a maximum and a minimum transmission value in the transmission vs. time curve for that layer. Even in this case, this method does not contain inherent compensation for errors in the thickness of previously deposited layers, and thus is not as forgiving as the turning-point method. However, to obtain an edge filter with high transmission and low ripple requires primarily non-quarter-wave thick layers, and hence turning-point monitoring is not applicable for edge filters.

Besides thin-film filters, the other predominant type of optical filter used for the applications described herein is the volume holographic filter. These filters accomplish blocking of unwanted excitation light with a "notch" of very low transmission over a relatively narrow bandwidth, and hence are often called "holographic notch filters." The non-transmitted light is diffracted at an acute angle relative to the direction of the transmitted light. The holograms are exposed and developed in a thick gelatinous film that is typically sandwiched between two glass substrates. Because the film can be relatively thick, allowing a very large number of fringes in the holographic grating, such filters can achieve a narrow notch bandwidth with accordingly steep edges.

A need in the art exists for an improved method of making optical edge filters and notch filters and for improved edge filters and notch filters having increased edge steepness and increased transmission.

SUMMARY OF THE INVENTION

These problems are addressed and a technical solution achieved in the art by high performance optical edge filters, high performance notch filters, and methods of making the same according to an embodiment of the present invention. In particular, the optical edge filters have an edge steepness less than about 0.8% as measured by dividing (a) the edge width from the 50% transmission wavelength to the optical density 6 ("OD6") wavelength by (b) the 50% transmission wavelength. The optical edge filters also have an average transmission above about 95%.

The notch filters exhibit a blocking of OD>6, very high transmission (>90%) outside the notch(es), and a narrow notch bandwidth comparable to that of holographic notch filters. In addition, this performance can be achieved with a single notch or multiple notches. Finally, the inventive notch filters achieve almost the same performance for filters at a 45 degree angle of incidence, with the exception that the blocking is OD>5.

The methods for making these edge and notch filters accurately determine when deposition of each layer of a filter should terminate. The methods include calculating theoretical transmission data for a layer of the filter and calculating an expected deposition duration for the layer. The methods also include measuring transmission through the layer during deposition for a period less than the expected deposition duration. When the measuring period elapses, a new deposition duration is calculated based upon the theoretical transmission data and the measured transmission data, thereby providing an accurate deposition duration for the layer.

BRIEF DESCRIPTION OF THE DRAWINGS

The advantages, nature and various additional features of the invention will appear more fully upon consideration of the illustrative embodiments now to be described in detail in connection with the accompanying drawings. In the drawings:

FIGS. 10 and 11 are transmission and optical density spectra, respectively, of an LWP filter fabricated in accordance with an embodiment of the invention;

FIGS. 12 and 13 are transmission and optical density spectra, respectively, of an SWP filter fabricated in accordance with an embodiment of the invention;

FIGS. 14 and 15 illustrate transmission and optical density spectra, respectively, of a 633 nm single-notch filter fabricated in accordance with an embodiment of the invention;

FIGS. 16 and 17 illustrate transmission and optical density spectra, respectively, of a first triple-notch filter fabricated in accordance with an embodiment of the invention;

FIGS. 18 and 19 illustrate transmission and optical density spectra, respectively, of a second triple-notch filter fabricated in accordance with an embodiment of the invention;

FIG. 20 illustrates transmission spectra of the first and second sides of the second triple-notch filter associated with FIGS. 18 and 19;

FIGS. 21 and 22 illustrate predicted transmission and optical density spectra, respectively, of a single-notch filter fabricated in accordance with an embodiment of the invention, wherein light impinges the filter at a 45 degree angle of incidence; and FIGS. 23 and 24 illustrate transmission and optical density spectra, respectively, of a quadruple-notch filter fabricated in accordance with an embodiment of the invention.

It is to be understood that these drawings are for illustrating the concepts of the invention and, except for data graphs, are not to scale.

DETAILED DESCRIPTION OF THE INVENTION

The invention has four aspects: A) apparatus programmed to make improved optical edge and notch filters; B) the method of making the improved filters; C) the improved filters made by the method and D) applications of the improved filters. These aspects will be described in the order presented.

A. Apparatus for Making Optical Edge and Notch Filters in Accordance with an Embodiment of the Invention Optical edge filters and notch filters in accordance with an embodiment of the invention are made using a computer-controlled deposition system. Advantageously the deposition is an ion beam sputtering deposition system using a beam assist source for depositing hard coatings and having an integral optical monitoring system to monitor deposition. A data processor, responsive to signals from the monitoring system, processes these signals and directs the growth of improved optical edge filters in accordance with algorithms described below.

Figure 4:
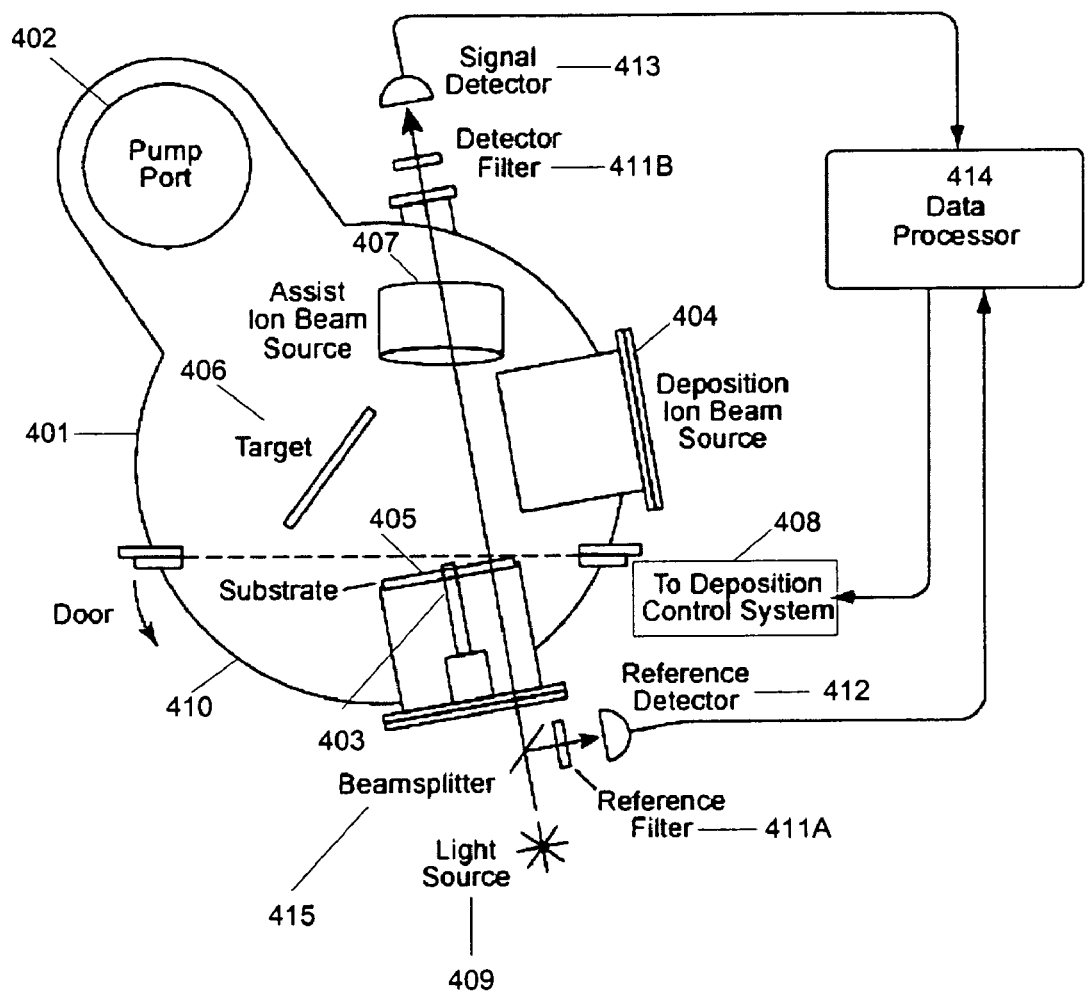
FIG. 4 is a schematic diagram of apparatus useful in making an optical edge filters and notch filters in accordance with an embodiment of the invention.

FIG. 4 is a schematic view of an advantageous computer-controlled deposition apparatus 400 for practicing ion-assisted, ion-beam sputtering disposition and optical monitoring under data processor control. The apparatus 400 comprises a vacuum chamber 401 having an interior accessible by a sealable port 402 such as an o-ring sealed door. The chamber 401 includes a pump port 402 for coupling to one or more evacuation pumps (not shown) such as mechanical and low pressure cryogenic pumps.

Within the chamber 401 is a substrate mount 403 which is advantageously a rotatable spindle mount. Also within the chamber are a plurality of material targets, a deposition ion beam source 404, and a mounted substrate 405. One of the targets 406 is positioned in relation to the ion beam source and the substrate so that an ion beam from the source will sputter material from the target onto the substrate in a substantially uniform layer. Typically there are separate targets for each material to be deposited on the substrate, and the targets are movable to and from the sputtering position. There are usually two material targets: one a high optical index material and the other a low index material. The targets are movable so that deposition can be switched automatically from one material to the other.

An assist ion beam source 407 is disposed in the chamber 401 in position to bombard the substrate 405 with an ion beam. During the deposition of any one material, the substrate is simultaneously bombarded by sputtered material and by ions from the assist ion beam source 407. The assist ion bombardment serves to energize the adhesion of particles onto the surface of the substrate and thereby produce a substantially more dense ("hard") film than would otherwise be formed by sputter deposition. See J. M. E. Harper et al., "Modification of Thin Film Properties by Ion Bombardment During Deposition," in *Ion Bombardment Modification of Surfaces*, Ed. By O. Auciello and R. Kelly, from *Beam Modifications of Materials*, Vol. 1 (Elsevier, Amsterdam, 1984).

Both the sputter deposition and the assist bombardment can be activated by a deposition control system 408. The control system 408 can start or stop deposition precisely by turning on and off the deposition ion beam source 404 or by removing or engaging a mechanical shutter (not shown) that covers the substrate. Further details concerning ion beam sputtering deposition systems can be found in U.S. Pat. No. 4,142,958 issued to David Wei et al. on Mar. 6, 1979 and U.S. Pat. No. 4,793,908 issued to Gene Scott et al. on Dec. 27, 1988, both of which are incorporated herein by reference. See also Juergen Becker, "Ion Beam Sputtering," Handbook of Optical Properties, Vol. 1, Thin Films for Optical Coatings, pgs 189–211, Ed. by R. E. Hummel and K. H. Guenther (CRC Press, Boca Raton, 1995).

The optical monitoring system advantageously comprises a light source 409, filters 411A and 411B, detectors 412 and 413 and a data processor 414. The light source 409 can be any sufficiently bright, broadband light source, such as a quartz halogen bulb or a Xenon discharge lamp. The detectors can include a reference detector 412 and a signal detector 413. The detectors can be semiconductor (Si) photodiodes, photomultiplier tubes or any other sensitive, low-noise detectors capable of detecting light at the monitoring wavelength.

In the advantageous arrangement shown here, a beamsplitter 415 picks off a portion 416 of the monitoring light beam 417 from source 409 and detects it with reference detector 412. The signal detector 413 detects the portion 418 of the beam 417 that passes through the coated substrate (or a "witness" substrate) being monitored. Advantageously, the filters 411A and 411B are positioned to ensure that a sufficiently narrow band of wavelengths is monitored.

The filters 411A, 411B can be narrow band interference filters, adjustable diffraction-grating monochromators or combinations thereof. Advantageously an interference filter is used for reference filter 411A and a monochromator is used for detector filter 411B. Further details concerning optical monitoring of thin films as they are being deposited can be found in U.S. Pat. No. 6,649,208 issued to Wayne Rodgers on Nov. 18, 2003, which is incorporated herein by reference. See also H. Angus Macleod, *Thin Film Optical Filters* ($3^{rd}$ Ed., Institute of Physics, Bristol, 2001) and H. A. Macleod, "Turning Value Monitoring of Narrow-Band All-Dielectric Thin-Film Optical Filters," *Optica Acta*, vol. 19, pp. 1–28(1972).

The data processor 414 collects data from the signal and reference detectors 413, 412, implements the mathematics associated with optical monitoring algorithms and instructs the deposition control system 408 when to stop depositing any given thin film layer based on the result of the mathematical calculations prescribed in the algorithm.

B. Methods of Making the Improved Edge Filters and Notch Filters

The manner in which the data processor 414 controls the apparatus 400 via the deposition control system 408 to generate the optical edge filters and/or notch filters according to an embodiment of the present invention will now be described. In particular, the data processor 414 is programmed to instruct the apparatus 400 when to stop depositing each layer of the filter being manufactured. In regard to edge filters, the data processor 414 follows two separate processes in determining when deposition of a layer should terminate depending upon whether a long-wave-pass or a short-wave-pass filter is being manufactured. These two processes will be described in turn. A description of the processes performed for manufacturing a notch filter will follow.

FIG. 4 illustrates the process flow executed by the data processor 414 when manufacturing a long-wave-pass ("LWP") filter according to an embodiment of the present invention. However, prior to initiating the process of FIG. 4, a design for the LWP filter is prepared. In the exemplary embodiment, the LWP filter has N layers and comprises two materials: a low-refractive-index material and a high-refractive-index material. The exemplary initial design for a steep LWP edge filter includes a quarter-wave ("QW") stack of (0.5H L 0.5H)^N, where L and H represent layers of high and low index materials with a quarter-wave of optical thickness at the reference wavelength. The reference wavelength is chosen so that the longer-wavelength edge of the QW stopband is close to the desired transition wavelength of the LWP filter design.

Once the initial design is setup, a desired target spectrum is constructed, which typically includes the wavelength ranges of both the blocking and passband regions, as well as the required blocking level and minimum transmission and allowable ripple within the passband. The edge steepness is thus indirectly defined as the wavelength separation between the blocking region and the passband.

The layer thicknesses of the initial design are then optimized against the target spectrum by an optimization routine known in the art. Exemplary optimization routines include the variable-metric or simplex methods implemented in standard commercial thin-film design software packages, such as TFCalc by Software Spectra, Inc., and The Essential Macleod by Thin Film Center Inc. Usually, with the proper choice of the initial design, the optimization quickly converges and the optimized structure is not very different from the initial structure. Special treatments may be necessary for the first layer (toward substrate) and the last layer. For instance, the optical thickness of the first layer may need to be manually increased—a typical minimum thickness in this case is two QWs. As for the last layer, it sometimes becomes too thin and thus may be eliminated. The structure should be re-optimized whenever there is any modification to the layer thickness.

With the LWP filter design at hand, the data processor 414 receives design data and deposition rate data as input at 501. The design data describes the designed thin-film structure of the LWP filter with a physical thickness $d_i$ and an index $n_i$ for each $i^{th}$ layer. $n_i$ is either $n_L$ or $n_H$, where $n_L$ is the refractive index of the low-index material and $n_H$ is the refractive index of the high-index material. $n_L$ and $n_H$ are each known as a function of wavelength $\lambda$. The deposition rate data describes the known starting deposition rate of the deposition apparatus 400 shown in FIG. 4 for each of the two materials. In the exemplary embodiment, the deposition rate data is within about +/−5% of the actual deposition rate and is in units of Å/sec. The starting rate estimates for each of the two materials are referred to as $r_L$ and $r_H$, and hence each layer will have a starting rate estimate $r_i$ depending on whether it is made of low-index or high-index material.

At 502, the transmission $T_i$ as a function of physical thickness d for each $i^{th}$ layer is calculated at a series of wavelengths in the transmissive band of the finished filter. Consequently, the calculations at 502 result in a series of curves $T_i$ vs. d at each of the series of wavelengths in the transmissive band of the finished filter. Such calculations are performed using standard mathematical methods for calculating the optical properties of thin-film filters. See, for example, H. A. Macleod, *Thin-film Optical Filters*, 3$^{rd}$ edition (Institute of Physics, Bristol, 2001).

Advantageously, instead of calculating each $T_i$ vs. d curve at one corresponding wavelength in the series of wavelengths, each $T_i$ vs. d curve is calculated by averaging a plurality of $T_i$ vs. d curves calculated at a range of wavelengths surrounding the corresponding wavelength. For instance, assume that the series of wavelengths includes 501 nm and 502 nm. Instead of calculating a $T_i$ vs. d curve at just 501 nm, this $T_i$ vs. d curve is advantageously calculated by averaging $T_i$ vs. d curves calculated at, for instance, 500 nm, 501 nm, and 502 nm. Further, the $T_i$ vs. d curve at 502 nm is advantageously calculated by averaging $T_i$ vs. d curves calculated at, for instance, 501 nm, 502 nm, and 503 nm. One skilled in the art will appreciate that invention is not limited to this averaging procedure and the range of wavelengths used.

At 503, an optical monitoring wavelength $\lambda_m$ is selected from the series of wavelengths in the transmissive band of the finished filter, thereby identifying a single curve $T_i$ vs. d at $\lambda_m$ from the series of curves computed at 502. The monitoring wavelength $\lambda_m$ is determined based on the contrast of the monitoring signal within each layer. The contrast is defined as the relative range of the monitoring signal within the layer of interest. The higher the contrast, the more robust the process flow of FIG. 4 will be with respect to random signal noise.

Advantageously, the relative separation between the monitoring and cutoff wavelengths should be at least about 2%. Once above 2%, the monitoring wavelength $\lambda_m$ should be chosen to maximize the contrast of each layer. In addition, the optical thickness of the first layer toward the substrate has a significant impact on the signal contrast for the rest of the structure. Therefore, the optical thickness of the first layer should be close to an odd-integer number of quarter-wavelengths at the monitoring wavelength $\lambda_m$.

Having determined the monitoring wavelength $\lambda_m$ at 503, processing advances to 504 where it is determined how the deposition duration for each layer will be calculated. For layers that are predicted to have little error between the designed thickness d and a simulated actual thickness, deposition duration is controlled by optically monitoring transmission levels $T_m$ through the layer during deposition. For the other layers, their deposition durations are controlled using an expected deposition time $t_i$ based upon designed ("theoretical") thickness $d_i$ and deposition rate $r_i$. Accordingly, at 504, the data processor 414 determines which layers are to be optically monitored and which layers are to be timed using an expected deposition time.

To determine which layers will be optically monitored, the data processor 414 enters a simulation mode to simulate deposition of each of the layers of the optical filter. Only the layers that are determined by the simulation to have the least amount of error are selected for optical monitoring. The simulation mode is nearly identical to the process described below with reference to 505 to 522, except that layers are not actually deposited at 505 and 506, the processing described at 508 is skipped, and instead of actually measuring transmission data $T_m$ vs. t at 511, it is generated. $T_m$ vs. t is generated by adding random noise to the theoretical data $T_i$ vs. d at $\lambda_m$ from 502 and 503. In the exemplary embodiment, 0.2% peak-to-peak random noise is used, and the maximum amount of error ("threshold") to select a layer for optical monitoring is to have no more than about 0.2% error from the theoretical thickness $d_i$. The error calculation, in this regard, is discussed in more detail below with reference to 518 and 519. The layers that are simulated to exceed the threshold amount of error are flagged to have their deposition duration controlled by the best estimate of the deposition rate $r_i$ for that layer or from an average of the rates of the previous layers of like material (typically 10 to 20 of such layers).

After determining which layers are to be optically monitored at 504, actual deposition of the layers of the LWP filter begins at 505. In particular, the substrate is loaded into the deposition apparatus 400 of FIG. 4, the apparatus is pumped down to a vacuum, and deposition of the first layer (current layer i) is initiated at 506. The expected deposition time $t_i$ for layer i is calculated as the desired thickness $d_i$ divided by the estimated deposition rate $r_i$ for the layer or from an average of the rates of the previous layers of like material at 507. It should be noted, however, that calculation of the expected deposition time $t_i$ at 507 may be calculated prior to beginning actual deposition of the current layer i at 506.

After calculating the expected deposition time $t_i$, it is determined whether the current layer i has been identified as a layer to be optically monitored for controlled deposition duration. If the current layer has not been so identified, deposition of the current layer terminates when the expected deposition time $t_i$ from 507 expires, as shown at 509. After the expected deposition time $t_i$ has expired, processing advances to 521 where the next layer is queued up for deposition, as shown at 510.

If it is determined at 508 that the current layer i is to be optically monitored, the actual transmission $T_m$ is measured at 511 as a function of actual time transpired t until about 95% of the expected deposition time $t_i$ has elapsed. Once about 95% of $t_i$ has elapsed, a new deposition duration is calculated at 512–520. In particular, at 512, 513, and 514, using the $T_i$ vs. d at $\lambda_m$ curve from 502 and 503, a two-dimensional (2D) array of additional curves is generated by plotting the values of $T_i$ against a 2D array of time vectors $t_{jk}$. In particular, at 513, transmission $T_{ij}$ is generated by plotting $T_i$ against the values $t_j=d/r_j$, where $r_j$ represents, for each j, a deposition rate having a value close to the predicted value $r_i$. That is, the set of all $r_j$ values is a range of values surrounding the predicted value $r_i$. Accordingly, j is an index that counts the number of r values that come from the range surrounding the predicted value $r_i$. At 514, for each value of j, transmission $T_{ijk}$ is generated by plotting $T_{ij}$ against the values $t_{jk}=t_j+\Delta t_k$, where $\Delta t_k$ represents various values used for a uniform time shift.

At 515, it is determined whether there is more than one extremum in the curve $T_i$ vs. d at $\lambda_m$. If there is more than one extremum at 515, then each of the 2D array of curves generated at 512–514, is scaled in two ways at 516. First, the mid-point between the two extrema for each $T_{ijk}$ curve is scaled by a factor so that it equals the mid-point between the two extrema of the measured data $T_m$ vs. t. Second, the maximum and minimum values on each $T_{ijk}$ curve are scaled by scaling uniformly about their mean so that the difference between the maximum and minimum for each curve $T_{ijk}$ is the same as that on the measured curve $T_m$ vs. t. If there is one or no extremum at 515, then the mean of each $T_{ijk}$ curve is scaled at 517 by a uniform factor so that it is equal to the mean of the measured curve $T_m$ vs. t.

After scaling at 516 or 517, processing advances to 518 where error is calculated. For each of the 2D array of generated $T_{ijk}$ curves, the root-mean-square (RMS) error between each $T_{ijk}$ curve and the measured curve $T_m$ vs. t is computed. Typically this computation is performed only for data between about 10% and 95% of the expected deposition time $t_i$. Afterwards, the values of j and k that yield a minimum RMS error at 518 are identified at 519. Therefore, the curve $T_{ijk}$ vs. $t_{ijk}$ is taken to be the best approximation of the actual curve $T_m$ vs. t for layer i. At 520, the curve $T_{ijk}$ vs. $t_{ijk}$ is compared against the design curve $T_i$ vs. d at $\lambda_m$ from 502 and 503, and the time $t_{ijk}$ at which the layer should be terminated is computed. When the measured time t reaches $t_{jk}$, the deposition for the optically monitored layer i is terminated.

After deposition of the current layer i has completed, the apparatus 400 of FIG. 4 is reconfigured at 521 to start depositing the material associated with layer i+1, and the process loops back to 506. However, if all layers of the filter have been deposited, the LWP filter is complete, and processing stops at 522.

Figure 5:
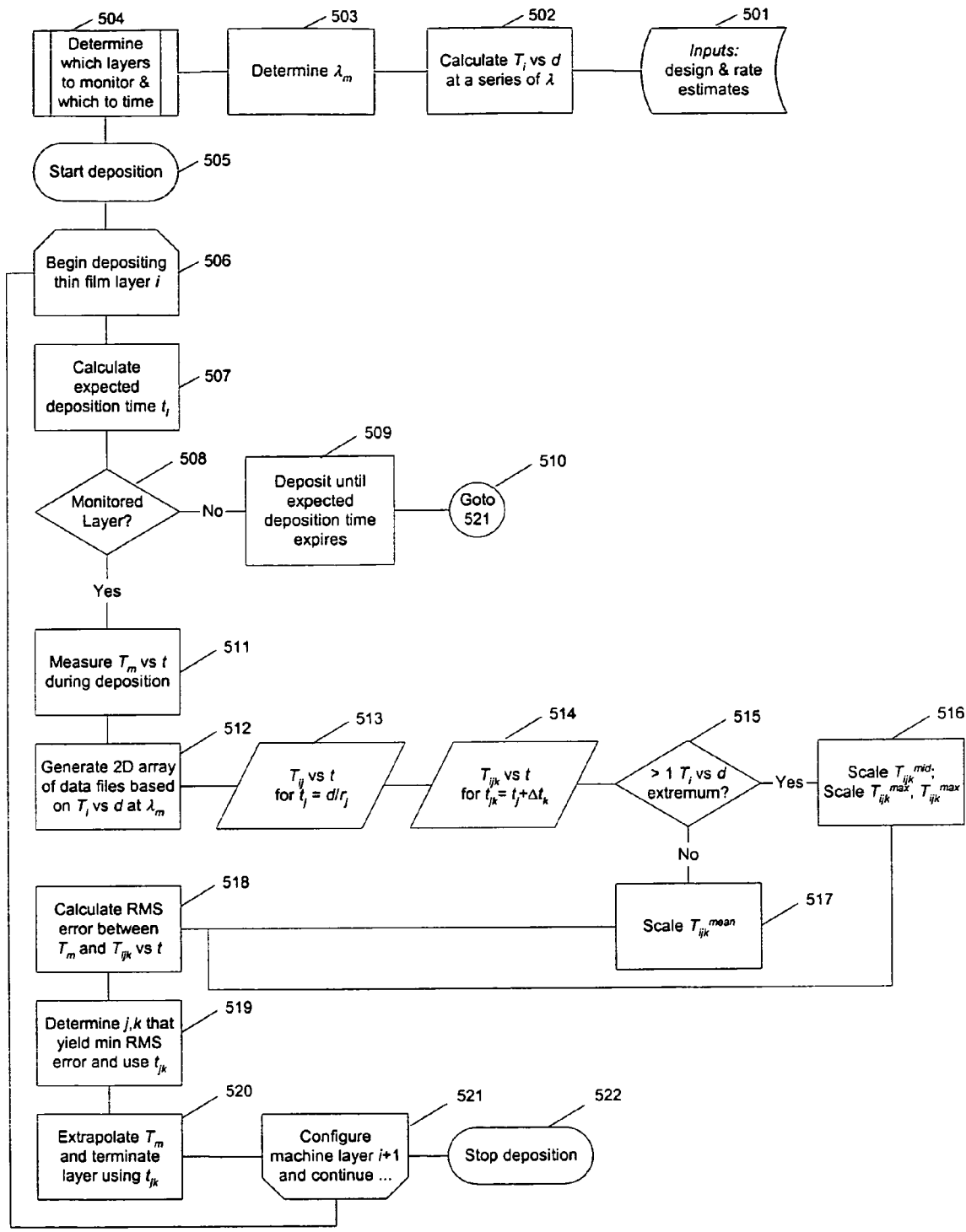
FIG. 5 is a process flow illustrating the process of manufacturing a long-wave-pass filter in accordance with an embodiment of the invention.

Turning now to FIG. 5, the process flow executed by the data processor 414 when manufacturing a short-wave-pass ("SWP") filter according to the exemplary embodiment of the present invention is described. The process illustrated with FIG. 5 is based on the inventor's observation that the inverse of the monitoring trace (i.e., the transmission of the monitoring light as a function of time) within each layer follows a sinusoidal pattern. As will be shown, only four parameters, $\beta_1$, $\beta_2$, $\beta_3$, and $\theta_{m+1}$, are needed to fully describe the behavior of the monitoring trace for each layer.

Assume that at the monitoring wavelength the incident medium, deposited materials, and substrate are all lossless (practically true). At normal incidence, each layer may be described by its characteristic matrix:

$$\begin{bmatrix} \cos\theta & -i\sin\theta/n \\ -in\sin\theta & \cos\theta \end{bmatrix} \quad (1)$$

where n is the refractive index of the layer, θ is the accumulated phase within the layer, and i in equations 1 through 8 (and only in these equations) is the square root of −1, or $i=\sqrt{-1}$. (It should be noted that although this specification is described in the context of light striking a filter at normal incidence, one skilled in the art will appreciate that this invention also applies to polarized light striking a filter at non-normal incidence.) θ is expressed as:

$$\theta = \frac{2\pi}{\lambda_m} nd \quad (2)$$

where d is the metric thickness of the layer and $\lambda_m$ is the monitoring wavelength. Assuming an assembly of m layers have already been deposited, the transmission of the monitoring light within the $(m+1)^{st}$ layer, the present layer, may be expressed as:

$$T = \frac{4n_a n_s}{H} \quad (3)$$

where T is the level of monitoring signal within the present layer (transmission), and $n_a$ and $n_s$ are the refractive indices of the incident medium and substrate, respectively. H is defined as:

$$H = \beta_1 + \beta_2 \cos 2\theta_{m+1} + \beta_3 \sin 2\theta_{m+1} \quad (4)$$

$\beta_1$, $\beta_2$, and $\beta_3$ are defined as:

$$\beta_1 = \frac{n_a^2 + n_{m+1}^2}{2}\left(|p|^2 + \frac{|q|^2}{n_{m+1}^2}\right) + 2n_a \text{Re}(pq^*) \quad (5)$$

where Re(pq*) is the Real Part of the product of the complex number p and the complex conjugate of the complex number q. p and q are defined in equation (8) below.

$$\beta_2 = \frac{n_a^2 - n_{m+1}^2}{2}\left(|p|^2 - \frac{|q|^2}{n_{m+1}^2}\right) \quad (6)$$

$$\beta_3 = \left(\frac{n_a^2}{n_{m+1}} - n_{m+1}\right)\text{Im}(p^*q) \quad (7)$$

where $\theta_l$ is accumulated phased in the $l_{th}$ layer. Im(pq*) is the Imaginary Part of the product of the complex conjugate of the number p and the complex number q. p and q are defined as:

$$\begin{bmatrix} p \\ q \end{bmatrix} = \prod_{l=1}^{m} \begin{bmatrix} \cos\theta_l & -i\sin\theta_l/n_l \\ -in_l\sin\theta_l & \cos\theta_l \end{bmatrix} \begin{bmatrix} 1 \\ n_s \end{bmatrix} \quad (8)$$

Based on the above equations, the relationship between the monitoring trace T and the accumulated phase $\theta m+1$ within the present layer is established. The inverse of the monitoring trace is sinusoidal, as demonstrated by the expression for H. Further, only four parameters, $\beta_1$, $\beta_2$, $\beta_3$, and $\theta_{m+1}$, are needed to fully describe the behavior of the monitoring trace in the present layer. Because the thickness d=rxt, where r is the deposition rate and t is the deposition time, a relationship between T and r or t is also established. If the deposition rate is constant, the accumulated phase $\theta_{m+1}$ is proportional to the deposition rate. Therefore, during the deposition process, the deposition rate may be retrieved with high accuracy by fitting the in-situ measurement of the monitoring trace to the four parameters.

With this groundwork, the process of FIG. 5 will now be described in greater detail. However, prior to initiating the process of FIG. 5, a design for the SWP filter is prepared. The process of designing a SWP edge filter is very similar to that of LWP filter, with several exceptions. First, the initial structure is (0.5L H 0.5L)^N. Second, the shorter wavelength edge of the QW stopband should be aligned with the desired cutoff wavelength. Third, if the first layer next to the substrate is a low index layer, it should be removed. Finally, it is advantageous, but not necessary, to artificially increase the optical thickness of the first layer.

With the design of the SWP filter at hand, the design data, as well as deposition rate data are received as input at 601. The input data has the content and format described with reference to 501 in FIG. 4. At 602, the transmission curves $T_i$ vs. d at a series of wavelengths for each $i^{th}$ layer are calculated as described with reference to 502 in FIG. 4. Choosing the best monitoring wavelength $\lambda_m$ at 603 is similar to that described with reference to 503 in FIG. 4, except that it may be more advantageous to select $\lambda_m$ by taking an average of a series of wavelengths than it is for an LWP filter.

At 604, the $\beta$ parameters are calculated for each layer at wavelength $\lambda_m$ using equations (1) through (8) described above. At 605, a determination is made as to which layers should have their deposition duration controlled by optical monitoring and which layers should have their deposition duration timed using an expected deposition time $t_i$. Such determination is made by simulating the deposition of each layer and selecting the layers having the least amount of simulated error to be optically monitored. Deposition of the other layers will be timed using the expected deposition time $t_i$.

The simulation process occurs by executing the processes of 606 to 617 as described below. However, actual deposition does not occur at 606 and 607, the processing described at 609 is skipped, and instead of measuring $T_m$ vs. t at 612, it is generated. $\lambda_m$ vs. t is generated by adding random noise to the theoretical data $T_i$ vs. d at $\lambda_m$ from 602 and 603. In the exemplary embodiment, 0.2% peak-to-peak random noise is used, and the maximum amount of error ("threshold") to select a layer for optical monitoring is to have no more than about 0.5% error from the theoretical resulting thickness $d_i$. The error calculation, in this regard, is described in more detail below with reference to 613. The layers that are simulated to exceed the threshold amount of error are flagged to have their deposition duration controlled by the best estimate of the deposition rate $r_i$ for that layer or from an average of the rates of the previous layers of like material (typically 10 to 20 such layers).

Having determined which layers are to be optically monitored at 605, deposition begins at 606. In particular, a substrate is loaded into the deposition apparatus 400, the apparatus 400 is pumped down to vacuum, and deposition of the first layer (current layer i) is initiated at 607. At 608, the expected deposition time $t_i$ for layer i is calculated as the desired thickness $d_i$ divided by the estimated deposition rate for the layer $r_i$ or from an average of the rates of the previous layers of like material. It should be noted, however, that calculation of the expected deposition time $t_i$ at 608 may be calculated prior to beginning actual deposition of the current layer i at 607.

At 609 it is determined whether the current layer i was identified as an optically monitored layer at 605. If not, deposition occurs until the expected deposition time $t_i$ expires, and the deposition apparatus is configured for deposition of the next layer, as shown at 610, 611, and 616. If it is determined that the current layer i is an optically monitored layer at 609, the transmission $T_m$ of the current layer is measured at 612 as a function of actual time t transpired, thereby producing a measured curve $T_m$ vs. $t_i$ until about 95% of time $t_i$ has elapsed. Once about 95% of the time $t_i$ has elapsed, a new layer time is calculated at 613 to 615.

To elaborate, at 613, $T_i$ vs. t (where t=d/r and $T_i$ vs. d at $\lambda_m$ was calculated and selected at 602 and 603, respectively) is fit to the measured curve $T_m$ vs. t from 612. The $T_i$ vs. t curve is fit to the measured curve $T_m$ vs. t by using a function that minimizes the error between the two curves by varying $\beta_1$, $\beta_2$, $\beta_3$, and the deposition rate r. An example of such a function is the Levenberg-Marquardt method implemented under the name "mrqmin( )" in the book *Numerical Recipes in C: The Art of Scientific Computing*, by Press, W. H.; Teukolsky, S. A.; Vetterling, W. T.; and Flannery, B. P., 2nd ed., Cambridge University Press, Cambridge, 1995. These calculations result in a calculated deposition rate for the current layer i, or $r_{ci}$.

Because of noise in the overall system and the sensitivity of the high-performance SWP filters to small layer-thickness errors, the calculated rates $r_{ci}$ tend to be insufficiently accurate if used directly. Therefore, a "best rate" for each layer, $r_{bi}$, is calculated at 614 as the average of the calculated rate $r_{ci}$ and calculated rates $r_{cj}, r_{cj+2}, \ldots, r_{c,i-4}, r_{c,i-2}$ for a certain number $(i-j)/2$ of previous layers of the same material. In other words, the best rate is a rolling average of the current and previous rates from layers of like material within a certain window. Typically, this window includes about 20 layers.

At 615, the best rate $r_{bi}$ is used to calculate the layer termination time $t_i = d/r_{bi}$, and the layer is terminated when the clock reaches this time. Once deposition of the current layer is complete, the deposition apparatus 400 of FIG. 4 is reconfigured at 616 to start depositing the material associated with the next layer i+1, and the process loops back to 607. However, if all layers have been deposited, manufacturing of the SWP filter is compete, and the process ends at 617.

Having described the processes of making LWP and SWP edge filters, the processes of making a notch filter according to embodiments of the invention will now be described. FIG. 7 illustrates a notch filter coating 701 applicable to both single and multi-notch filters, according to an embodiment of the present invention. The notch filter coating 701 is located on one side 702 of a substrate 703. The notch filter coating 701 includes alternating layers of high-index material 704 and low-index material 705. The materials may be hard oxide coating materials such as $SiO_2$, $Ta_2O_5$, $Nb_2O_5$, $HfO_2$, $TiO_2$, and $Al_2O_5$. Although not shown in FIG. 7, an anti-reflection coating may be present on the side 706 of the substrate 703 opposite to the notch filter coating 701. It should be noted that FIG. 7 is used merely as an illustration, is not to scale, and the number of layers is not necessarily accurate. The notch filter coating 701 may be made according to the method for making SWP coatings described above with reference to FIG. 6.

Figure 7:
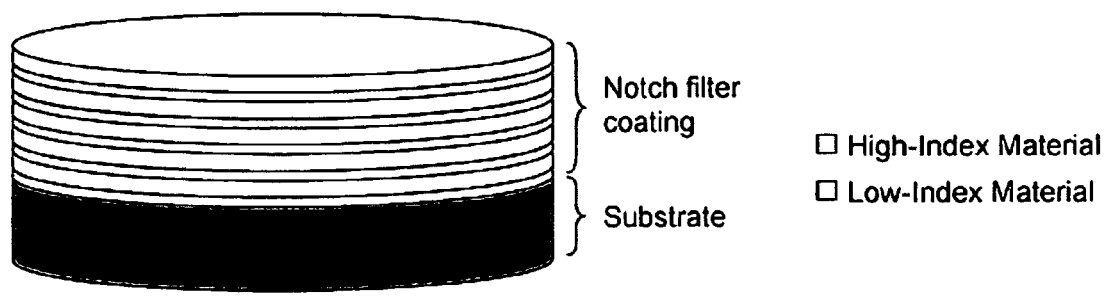
FIG. 7 illustrates a first structure of a notch filter in accordance with an embodiment of the invention.
Figure 8:
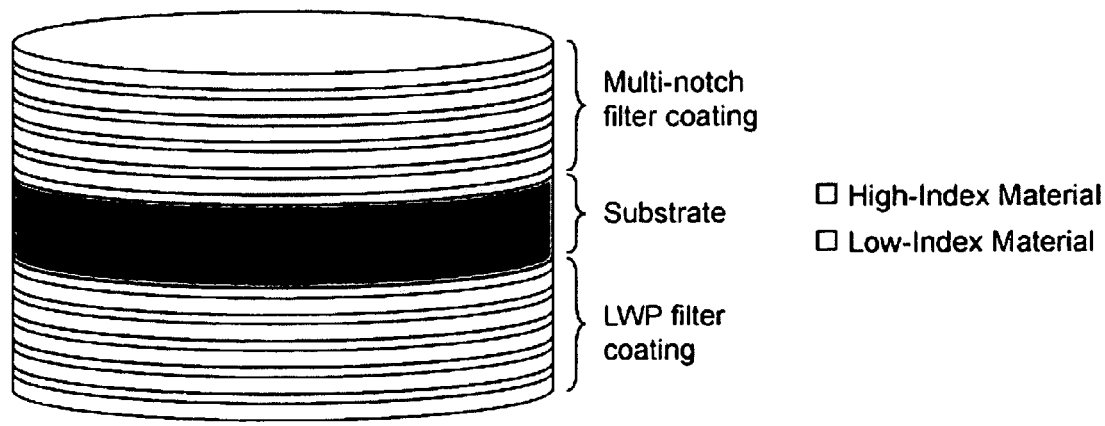
FIG. 8 illustrates a second structure of a notch filter in accordance with an embodiment of the invention.

FIG. 8 illustrates a multi-notch filter coating that utilizes a notch coating 801 on one side 802 of the substrate 803 and a long-wave-pass (LWP) coating 804 on the other side 805 of the substrate 803. Both the notch filter coating 801 and the LWP coating 804 include layers of alternating high-index material 806 and low-index material 807. The materials may be hard oxide coating materials such as $SiO_2$, $Ta_2O_5$, $Nb_2O_5$, $HfO_2$, $TiO_2$, and $Al_2O_5$. It should be noted that FIG. 8 is used merely as an illustration, is not to scale, and the number of layers is not necessarily accurate. As with FIG. 7, the notch filter coating 801 may be made according to the method for making SWP coatings described above with reference to FIG. 6. The LWP coating 804 may be made according to the method of making LWP coatings described above with reference to FIG. 5.

According to an embodiment of the present invention, the LWP coating 804 in FIG. 8 may be replaced with a multi-notch filter coating, like the multi-notch filter coating 801. The same and/or different multi-notch filter coatings may be deposited on both sides of the substrate 803. For example, three notches may be deposited on one side of the substrate 803, and three different notches may be deposited on the other side of the substrate 803, to produce a six-notch filter. Alternatively, several notches may be deposited on one side of the substrate 803 and the same several notches may be deposited on the other side of the substrate 803 to increase the OD of the notches. In particular, notches that are "weak," i.e., have a low OD, are strengthened with corresponding notches of higher OD on the other side of the substrate 803. (It should be noted that, due to interference effects associated with multiple reflections between the two multi-notch coatings on, the total OD associated with the two coatings is not necessarily the sum of the individual OD values.) Further, one side of the substrate 803 may have the same notches as the other side, as well as additional different notches. For instance, one side of the substrate 803 may have two notches, and the other side of the substrate 803 may have the same two notches as well as two additional different notches, thereby resulting in a four-notch filter.

Although the exemplary methods have been described in the context of manufacturing optical edge filters and notch filters, those skilled in the art will appreciate that such methods apply to manufacturing other types of optical filters, or may easily be modified to manufacture other types of optical filters. For instance, the methods are useful for any filter having even a single layer of critical thickness, such as a Fabry-Perot interferometer, where the layer of critical thickness is the resonance cavity. Further, although the exemplary methods are disclosed as having a particular sequence of events, one skilled in the art will appreciate that many of these events may occur in a different order without departing from the scope of the invention. Accordingly, the methods of the present invention are not limited to producing optical edge and notch filters and are not limited to the particular ordering of events described.

C. The Improved Filters

Figure 3:
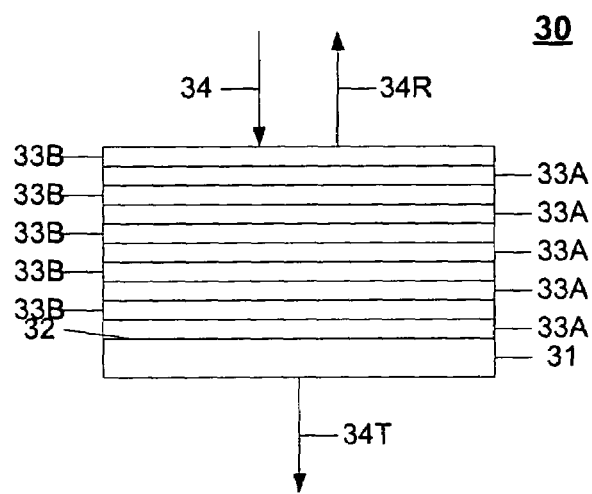
FIG. 3 is a schematic drawing illustrating the structure of a conventional optical filters.
Figure 6:
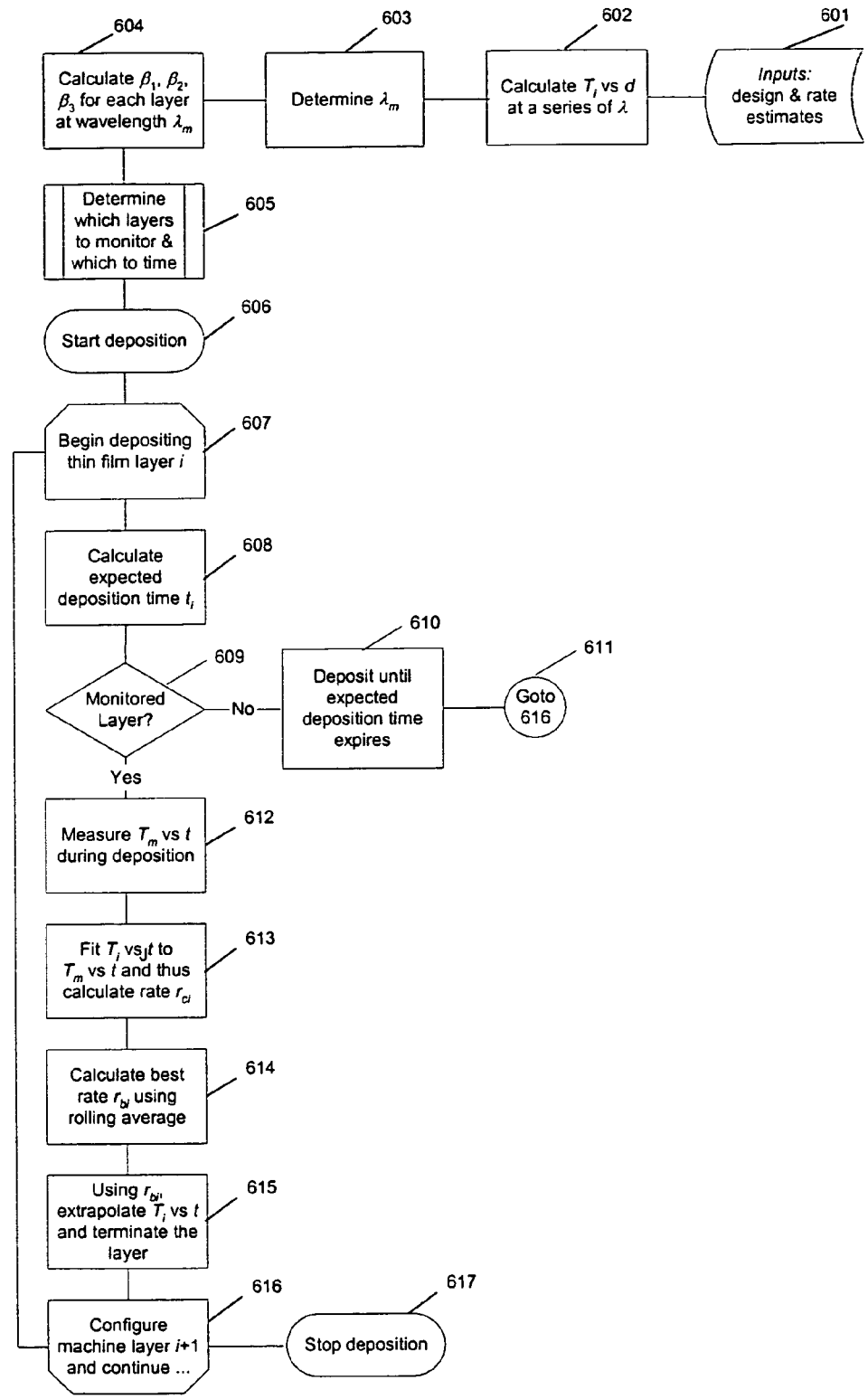
FIG. 6 is a process flow illustrating the process of manufacturing a short-wave-pass filter in accordance with an embodiment of the invention.

The improved edge filters have the general structure schematically illustrated in FIG. 3 but are made by the processes described herein in connection with FIGS. 5 and 6. In essence, the filters comprise a transparent substrate advantageously having a pair of optically flat planar major surfaces and a plurality of alternating layers of relatively high index and relatively low index materials. The materials may be hard oxide coating materials such as $SiO_2$, $Ta_2O_5$, $Nb_2O_5$, $HfO_2$, $TiO_2$, and $Al_2O_5$.

The edge filters differ from conventional edge filters primarily in the number of layers (typically more than 100) and in that the thicknesses of layers deposited are controlled by the processes of FIGS. 5 and 6 to produce an edge steepness less than about 0.8%. The edge steepness, in this regard, is measured by dividing (a) the edge width from the 50% transmission wavelength to the optical density 6 ("OD6") wavelength by (b) the 50% transmission wavelength. Accordingly, lower steepness values indicate greater slope. Optical density ("OD") is a measure of the blockage encountered by impinging light and is defined as follows:

$$OD = -\log_{10}(T) \qquad (9)$$

where T is the transmittance having a value between zero and one. OD6 therefore corresponds to a transmittance of $10^{-6}$.

Advantageously the edge steepness, as defined above, is less than about 0.463%. However, the edge steepness may be increased if necessary. In addition, the filters so made exhibit an average transmission above about 93% and preferably above at least 95% with ripple below about 2% in the operating range. In the case of a filter for a 532 nanometer laser-line, the operating range is approximately 200 nm from the wavelength at which the filter reaches full transmission. One skilled in the art will appreciate that the operating range is larger with filters for laser-lines at higher wavelengths. Transmission of the filters does not drop below 93% and preferably 95% in the operating range. The filters thus provide performance exceeding that of the highest performing conventional soft-coating filters with a more robust and durable hard-coated structure.

The edge filters can be constructed with an edge wavelength as short as 325 nm and as long as 1064 nm. It is contemplated that this range may be extended from as low as 250 nm to as high as 2,000 nm using the materials listed above.

As compared with conventional edge filters, the edge filters of the invention provide substantially higher edge steepness and passband transmission. Table I below presents a comparison between the inventive filters and the best known examples of conventional soft-coated and hard-coated thin-film edge filters. The data in Table I are from filters designed to block a 532 nm laser, where the 50% transmission wavelength is 537 nm. Accordingly, steepness (in percentage) is calculated as Edge Width divided by 537 nm.

TABLE I

|  | Hard-Coated | Soft-Coated | Inventive |
|---|---|---|---|
| Edge Width (50% to OD4) | ≈3 nm* | ≈4 nm* | <1.4 nm |
| Edge Steepness (50% to OD4) | ≈0.556% | ≈0.741% | <0.259% |
| Edge Width (50% to OD6) | ≈5 nm* | ≈6 nm** | <2.5 nm |
| Edge Steepness (50% to OD6) | ≈0.926% | ≈1.111% | <0.463% |
| Laser-Line Attenuation (OD) | >6.0 | >5.0 | >6.0 |
| Average Transmission | Approx. 90% | Approx. 85% | >95% and <= approx. 100% |

*Estimated specification
**Edge width for 50% to OD5 (necessarily less than Edge Width for 50% to OD6)

As can be seen from Table I, the edge filters of the present invention provide an improvement in edge steepness and a reduction of optical loss in the transmission band (optical loss defined as 100%—Average Transmission).

In addition, the inventive edge filters provide a substantial improvement in reliability and durability over soft-coated thin-film filters (the highest performing conventional filters) because the inventive filters are made exclusively with hard oxide glass, whereas soft-coated filters contain soft salts and organic materials susceptible to damage by humidity and temperature extremes.

The improved notch filters made by the processes disclosed herein have made it possible to achieve optical notch filtering in a thin-film format (at normal or near-normal incidence) with a blocking of OD>6, very high transmission (>90%) outside the notch(es), and a narrow notch bandwidth comparable to that of holographic notch filters. In addition, this performance can be achieved with a single notch or multiple notches. Finally, the inventive notch filters achieve almost the same performance for filters at a 45 degree angle of incidence, with the exception that the blocking is OD>5.

Table II summarizes the OD, transmission, and bandwidth specifications of the inventive notch filters (for normal incidence).

TABLE II

| Property | Value | Comments |
|---|---|---|
| Laser Line Blocking | >6 OD | OD = $-\log_{10}$ (transmission) |
| Notch Bandwidth (typical) | 17 nm or 600 cm$^{-1}$ for 532 nm | Full width at 50% transmission points |
| Average Passband Transmission | >90% & <= 100% | |

TABLE II-continued

| Property | Value | Comments |
|---|---|---|
| Passband Bandwidth* | 0.75 × $\lambda_L$ to 1.33 × $\lambda_L$ | $\lambda_L$ is the laser wavelength |
| Angle Tunability | >1% of laser wavelength | Wavelength "blue shift" |
| Temperature Dependence | <5 ppm/° C. | <0.003 nm/° C. at 532 nm |

*The passband includes the wavelength region indicated, but excludes the notch region.

Note that the bandwidth shown in Table II is given only for a 532 nm filter. For other laser wavelengths (we have demonstrated these filters for wavelengths between 405 nm and 830 nm), the typical bandwidth is found from the formula:

$$\text{Notch Bandwidth} = 55 \times 10^{-6} \times \lambda_L^2 + 14 \times 10^{-3} \times \lambda_L - 5.9 \quad (10)$$

$\lambda_L$ is the laser wavelength (in nm) and the Notch Bandwidth (NBW) also is in units of nm. The inventive optical notch filters manufactured in accordance with the invention have been demonstrated to have a transmission greater than 90% and less than or equal to about 100% at wavelengths that are greater than or equal to $\lambda_L$+1.3(NBW) and less than or equal to $\lambda_L$−1.3(NBW). Further, the inventive notch filters have been demonstrated to have a transmission greater than 90% and less than or equal to about 100% at wavelengths that are greater than or equal to $\lambda_L$+0.65(NBW), and less than or equal to $\lambda_L$−0.65(NBW). Further still, the inventive notch filters have been demonstrated to have a transmission greater than 90% and less than or equal to about 100% at wavelengths between ($\lambda_L$+1.3(NBW)) and $\lambda_L$/0.75, and between 0.75($\lambda_L$) and ($\lambda_L$−1.3(NBW)). In addition, the inventive notch filters have been demonstrated to have a transmission greater than 90% and less than or equal to about 100% at wavelengths between ($\lambda_L$+0.65(NBW)) and $\lambda_L$/0.75, and between 0.75($\lambda_L$) and ($\lambda_L$−0.65(NBW)).

Another advantage of the inventive notch filters is that their spectral features largely are unaffected by temperature variations. In particular, spectral features of the inventive notch filters, such as the wavelength at which 50% transmission occurs, or the wavelength at which maximum optical density occurs, shift less than approximately 0.0005% per degree Celsius and greater than approximately 0.00005% per degree Celsius.

Table III compares filters manufactured in accordance with embodiments of the present invention to prior-art holographic notch filters:

TABLE III

| Property | Kaiser Notch-Plus ™ Holographic Filter | Semrock StopLine ™ Notch Filter | Kaiser SuperNotch-Plus ™ Holographic Filter |
|---|---|---|---|
| Notch Bandwidth-frequency (for 532 nm filter) | <700 cm$^{-1}$ | <670 cm$^{-1}$ | <350 cm$^{-1}$ |
| Notch Bandwidth-wavelength (for 532 nm filter) | <20 nm | <19 nm | <10 nm |
| Laser Line Blocking | >6 OD | >6 OD | >6 OD |
| Transmission | >85% % <90% | >90% & <= approx. 100% | >85% & <90% |

In addition to the spectral advantages over the prior art of holographic filters, the new thin-film notch filters also offer the following advantages. Blocked light is back-reflected, rather than diverted at an acute angle, thereby simplifying system layout and improving stray-light management. Because the inventive notch filters are thin-film filters, they are very compact and simple to integrate into a variety of optical systems. Further, thin-film filters are inherently lower in cost because many filters are manufactured simultaneously in a parallel approach. Compared to both holographic filters and thin-film filters made with older technologies (e.g., soft coatings), the inventive filters offer far superior reliability and durability because the all-dielectric coatings are based on hard refractory oxide materials. The dense, all-glass coatings used for notch filters, according to an embodiment of the invention, enable almost-zero temperature dependence to maximize the operating temperature range of instruments without the need for expensive compensation hardware. Additionally, the temperature shift for the inventive notch filters is less than 5 ppm per degree Celsius (or less than 0.003 nm per degree Celsius for a 532 nm filter). The coatings used for the inventive notch filters offer a very high laser damage threshold. A 532 nm notch filter has been tested and proven to have a damage threshold above 1 Joule/cm$^2$ for a 532 nm laser pulse of 10 ns duration.

For multi-notch filters, dual-, triple-, and quadruple-notch filters according to an embodiment of the present invention, have been demonstrated to have OD>6 blocking at the laser lines. The examples below show two ways of making a multi-notch filter. In one embodiment of a triple-notch filter, which may have a structure as described with reference to FIG. 7, all of the filtering is done in a single coating 701, and the other side of a single-substrate 703 might be AR-coated to achieve the highest possible transmission. In another embodiment of a triple-notch filter, which may have a structure as described with reference to FIG. 8, a dual-notch filter 801 on one side 802 of the single substrate 803 is combined with a long-wave-pass (LWP) filter 804 on the other side 805 of the substrate to provide the full OD>6 blocking at the shortest of the three blocking wavelengths.

Figure 9A:
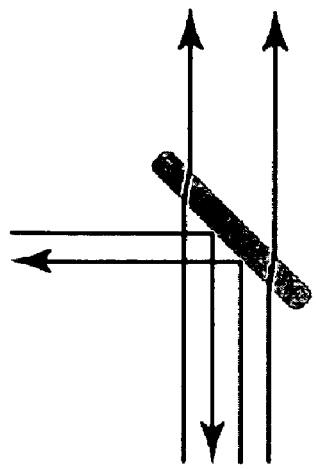
FIGS. 9A to 9C illustrate transmission through a notch filter at a 45 degree angle of incidence.
Figure 9B:
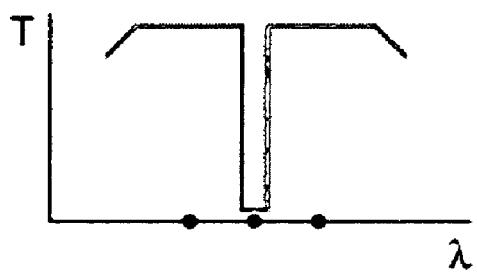
Figure 9C:
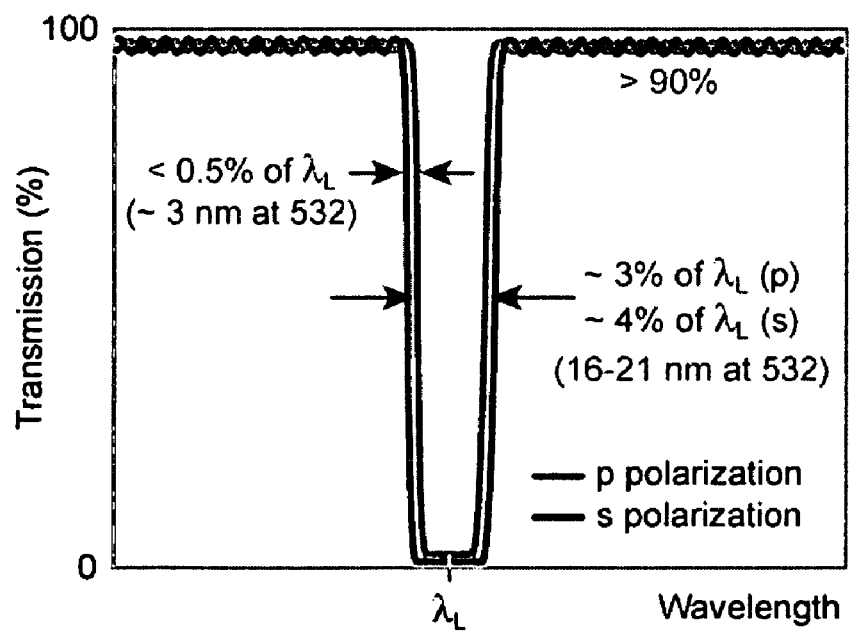

FIG. 9A illustrates a notch filter 901, which may have a structure as described with reference to FIG. 7 or FIG. 8, at a 45 degree angle of incidence. In this example, red light 902 and blue light 904 passes through the filter 901, and green light 903 is blocked by the filter 901. The transmission v. wavelength graph of the filter 901 is shown in FIG. 9B. FIG. 9C illustrates an expanded view of FIG. 9B. As shown in FIGS. 9A to 9C, and contrary to conventional notch filters, the notch filters made according to the present invention work well at a 45 degree angle of incidence. In particular, the notch filters made in accordance with the invention, when operated at an angle of incidence of approximately 45 degrees, exhibit transmission greater than 90% and less than or equal to approximately 100% at wavelengths that are greater than or equal to $\lambda_L$+1.3(NBW) and less than or equal to $\lambda_L$1.3(NBW). Further, the notch filters made in accordance with the invention, when operated at an angle of incidence of approximately 45 degrees, exhibit transmission greater than 90% and less than or equal to approximately 100% at wavelengths between ($\lambda_L$+1.3(NBW)) and $\lambda_L$/0.75, and between 0.75($\mu_L$) and ($\mu_L$−1.3(NBW)). In addition, the inventive notch filters enable very efficient beamsplitting and complete laser-line blocking all in one filter. ("Very efficient" beamsplitting may be described as almost complete reflection (substantially greater than 99% reflection) of light within a notch region, along with very high transmission (>90% transmission) of light outside of a notch region.)

It is believed that the combination of very efficient beamsplitting and complete laser-line blocking in a single notch filter is novel.

To elaborate, a laser may be introduced into a system by reflecting (with near 100% reflection) off of the filter at 45 degrees, then impinges on a sample, and the desired signal light (e.g. Raman scattering or fluorescence) that leaves the sample passes through the filter with high transmission, while the laser light is blocked with very high optical density (OD>5 for average polarization). A fundamental problem for all thin-film filters at a 45 degree angle of incidence is that there is a large degree of "polarization splitting"—that is, the spectral features associated with s- and p-polarized light shift to very different wavelengths. However, the amount of splitting at either edge of the inventive notch filters are extremely small (<0.5% of the laser wavelength), thus enabling this filter to provide very sharp edges for both polarizations simultaneously (and hence for light of average polarization). ("Very sharp" edges may be described as the wavelength range between the point at which high blocking (e.g., >99% blocking) for all polarizations is achieved and the point at which high transmission (e.g. >90% transmission) for all polarizations is achieved is very small, such as substantially less than 2% of the laser wavelength.) No edge filter operated at a 45 degree angle of incidence is known to provide very sharp edges for both polarizations simultaneously this well.

The invention can now be more clearly understood by consideration of the following specific examples.

EXAMPLE 1

Long-Wave-Pass Edge Filter

A steep-edge LWP filter for a 532 nanometer notch was designed and fabricated in accordance with the LWP design strategy described above. The filter blocks the 532 nanometer laser light and light of lesser wavelength but to transmit light of longer wavelength. Appendix A gives the layer structure of the design. The optical thickness is given in units of quarter wavelengths (QWs) at the monitoring wavelength of 568 nanometers. The layers are counted from the substrate outward toward air. The substrate is BK7 glass, marketed by vendors such as Schott Glass. The design has 180 layers with a total metric thickness of 12.7 micrometers.

FIG. 10 shows the theoretical and measured transmission spectra of the resulting 532 nm LWP edge filter in accordance with an embodiment of the invention. Curve 1001 is the theoretical spectrum, curve 1002 is the measured spectrum, and curve 1003 is the laser wavelength line at 532 nm.

FIG. 11 illustrates the optical density spectrum of the 532 nm LWP filter. As previously discussed, optical density (OD) is a measure of the blockage encountered by impinging light. Curve 1101 is the theoretical OD spectrum, curve 1102 is the measured OD spectrum, and curve 1103 is the 532 nm laser line. It is noteworthy that the filter edge is so steep that it is difficult to measure with standard spectrophotometry equipment. The apparent "kink" between OD3 and 4 is not real, but rather is produced by the measuring instrument.

EXAMPLE 2

Short-Wave-Pass Edge Filter

A steep-edge SWP filter was designed and fabricated in accordance with the SWP design strategy described above.

The filter is to block the 532 nanometer laser light and light of greater wavelength but to transmit light of shorter wavelength. Appendix B provides the layer structure of the design. The optical thickness is given in QWs at the monitoring wavelength of 510 nm. The substrate is BK7 glass. The design has 180 layers with a total metric thickness of 15.1 micrometers.

FIG. 12 illustrates the theoretical and measured transmission spectra 1201 and 1202, respectively, of the realized SWP filter. The laser-line at 532 nm is shown at 1203.

FIG. 13 shows the theoretical and measured optical density spectra 1301 and 1302, respectively, and the laser-line 1303. The apparent "kink" that occurs between about OD 4 and 5 is due to the limitations of the measuring instrument, not the filter.

EXAMPLE 3

633 nm Single-Notch Filter

A 633 nm single-notch filter having a structure corresponding to that shown in FIG. 7 was manufactured according to the processes described herein. The actual coating structure of this filter is set forth in Appendix C. A graph showing both the designed 1401 and measured 1402 transmission spectrum for this filter is shown at FIG. 14. FIG. 15 shows the designed 1501 and measured 1502 optical density for the manufactured 633 nm single-notch filter.

EXAMPLE 4

Single-Coating-Triple-Notch Filter

A single-coating-triple notch filter having a structure corresponding to that shown in FIG. 7 was manufactured according to the processes described herein. The actual coating structure of this filter is set forth in Appendix D. A graph showing both the designed 1601 and measured 1602 transmission spectrum for this filter is shown at FIG. 16. FIG. 17 shows the designed 1701 and measured 1702 optical density for the manufactured single-coating-triple notch filter.

EXAMPLE 5

Triple-Notch (Dual-Notch Plus LWP) Filter

A triple-notch (dual-notch plus LWP) filter having a structure corresponding to that shown in FIG. 8 was manufactured according to the processes described herein. The actual coating structure of this filter is set forth in Appendix E. A graph showing both the designed 1801 and measured 1802 transmission spectrum for this filter is shown at FIG. 18. FIG. 19 shows the designed 1901 and measured 1902 optical density for this filter. FIG. 20 separately shows the transmission spectra for the dual-notch coating 2001 and the LWP coating 2002 of this triple-notch filter.

EXAMPLE 6

Single-Notch Filter with 45 Degree Angle of Incidence

Characteristics were simulated of a single-notch filter manufacturable by the processes described herein and having a structure corresponding to that shown in FIG. 7. The coating structure of this filter is set forth in Appendix F. The predicted average polarization transmission spectrum 2101, the predicted s polarization transmission spectrum 2102, and the predicted p polarization spectrum for this filter with light impinging at a 45 degree angle of incidence are shown at FIG. 21. FIG. 22 shows the predicted average polarization optical density 2201, the predicted s polarization optical density 2202, and the predicted p polarization optical density 2203 for this filter with light impinging at a 45 degree angle of incidence.

EXAMPLE 7

Quadruple-Notch (Triplenotch Plus LWP) Filter

A quadruple-notch (triple-notch plus LWP) filter having a structure corresponding to that shown in FIG. 8 was manufactured according to the processes described herein. The actual coating structure of this filter is set forth in Appendix G. A graph showing both the designed 2301 and measured 2302 transmission spectrum for this filter is shown at FIG. 23. FIG. 24 shows the designed 2401 and measured 2402 optical density for this filter.

D. Applications of the Filters

Figure 1A:
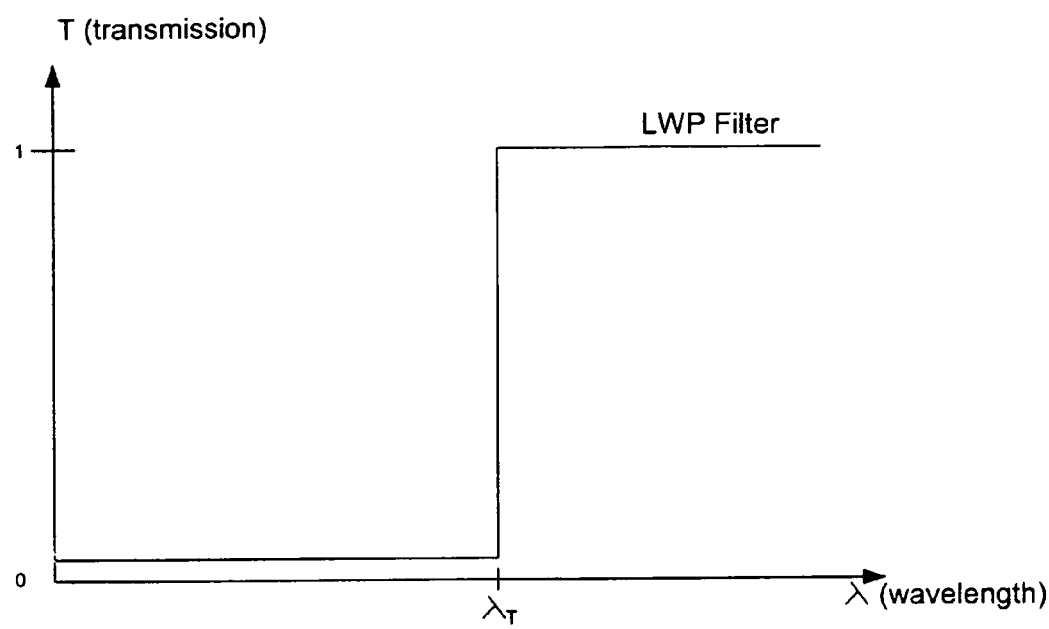
FIGS. 1A and 1B are schematic graphical illustrations showing the spectral transmission of long-wave-pass and short-wave-pass optical edge filters, respectively.
Figure 1B:
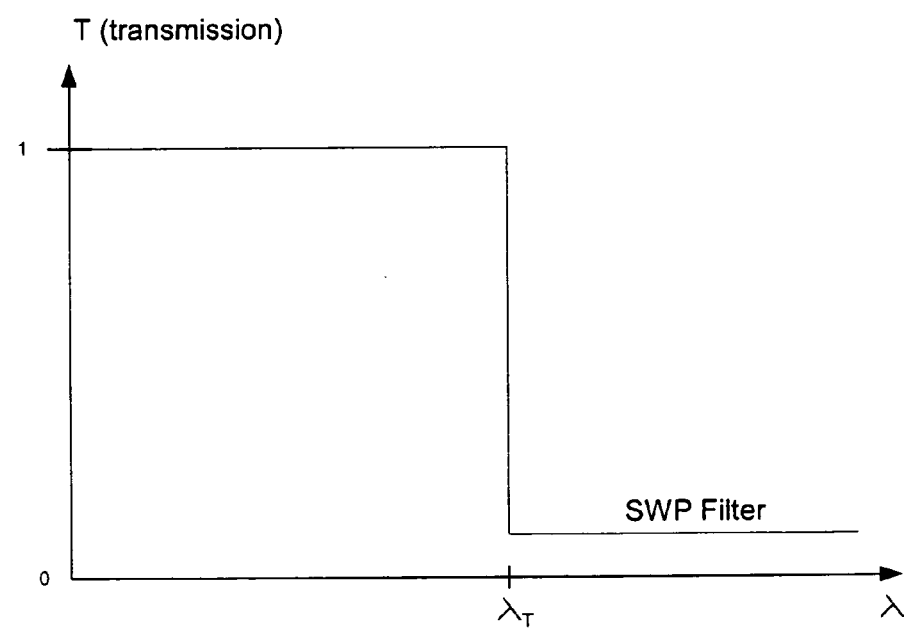
Figure 1C:
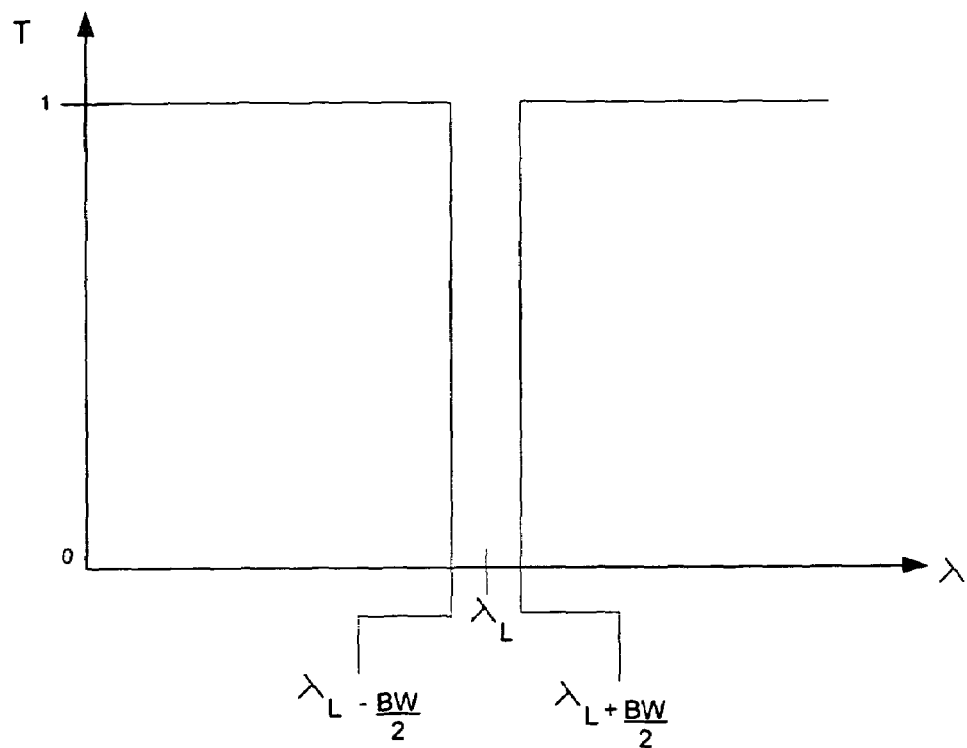
FIGS. 1C and 1D are schematic graphical illustrations showing the spectral transmission of an ideal and realistic notch filter, respectively.
Figure 1D:
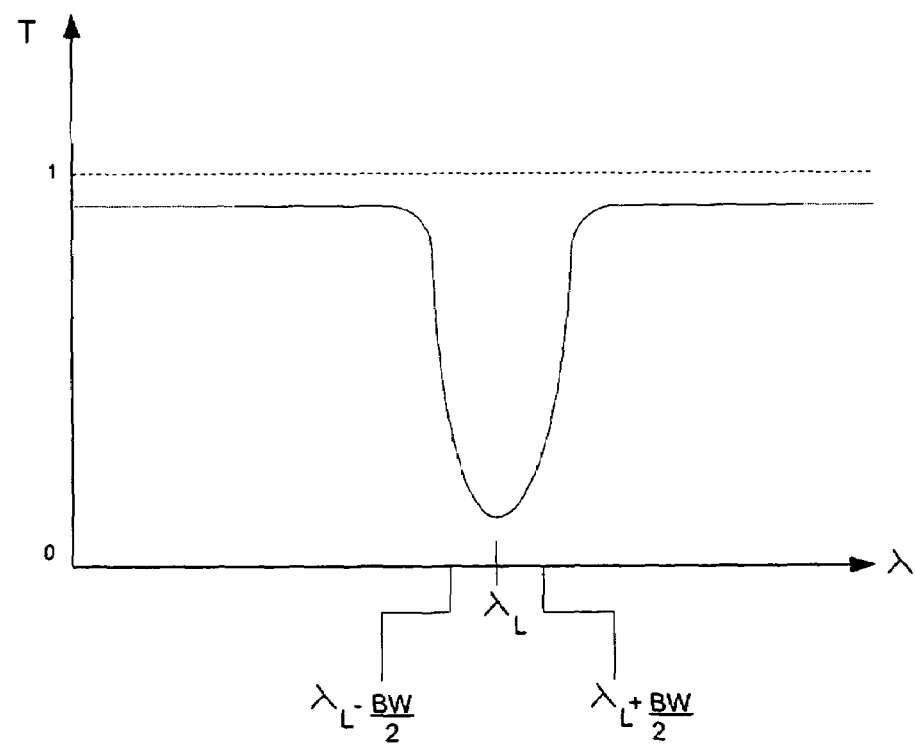
Figure 2:
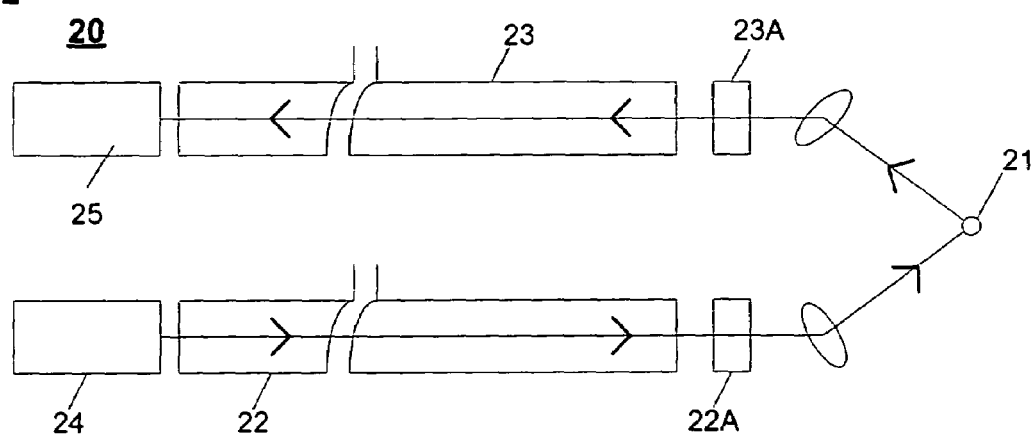
FIG. 2 is a schematic diagram of a conventional Raman probe.

The inventive filters can improve the performance of a variety of optical analysis systems that excite a sample of material with light of a first wavelength to produce a measurable or viewable response of light at a second wavelength different from the first. Such systems, which include Raman spectroscopy and fluorescence spectroscopy, are typically of the construction schematically shown in FIG. 2. They comprise a source of excitation light, an optical path coupling the excitation light to the sample, and one or more first filters in the path between the source and the sample for blocking light at some wavelengths different from the excitation light. They also include an optical path coupling the optical response light from the sample to an analyzer or viewer, and one or more second filters in the path between the sample and the analyzer or viewer for blocking some light other than the optical response. As previously discussed, the first filter(s) may be one or more edge filters, and the second filter(s) may be one or more notch filters and/or edge filters.

One or more optical edge filters and/or notch filters in accordance with an embodiment of the invention can substantially improve the performance of such optical analytical systems. The greater steepness of edge slope in the edge filter(s) permit(s) return of response wavelengths closer to the excitation wavelength providing an increase in the information content of the returned response. The greater steepness of edge slope in the notch filter provides better blocking of unshifted scattered excitation light in the returned response. The reduction in transmission loss means that the enhanced information return response will be at higher brightness, and the greater hardness and durability of the inventive filters permits a more robust and versatile instrument.

It is to be understood that the exemplary embodiments are merely illustrative of the present invention and that many variations of the above-described embodiment can be devised by one skilled in the art without departing from the scope of the invention. It is therefore intended that all such variations be included within the scope of the following claims and their equivalents.

APPENDIX A

| Layer # | Material | Optical Thickness | Metric Thickness (nm) |
|---|---|---|---|
| 1 | Ta2O5 | 2.5790 | 171.93 |
| 2 | SiO2 | 0.7851 | 74.97 |
| 3 | Ta2O5 | 0.7323 | 48.82 |
| 4 | SiO2 | 0.7163 | 68.40 |
| 5 | Ta2O5 | 0.8253 | 55.02 |
| 6 | SiO2 | 0.8398 | 80.19 |
| 7 | Ta2O5 | 0.8490 | 56.60 |
| 8 | SiO2 | 0.7960 | 76.01 |
| 9 | Ta2O5 | 0.8058 | 53.72 |
| 10 | SiO2 | 0.8080 | 77.15 |
| 11 | Ta2O5 | 0.8513 | 56.75 |
| 12 | SiO2 | 0.8356 | 79.79 |
| 13 | Ta2O5 | 0.8351 | 55.67 |
| 14 | SiO2 | 0.8029 | 76.67 |
| 15 | Ta2O5 | 0.8280 | 55.20 |
| 16 | SiO2 | 0.8286 | 79.12 |
| 17 | Ta2O5 | 0.8510 | 56.73 |
| 18 | SiO2 | 0.8276 | 79.03 |
| 19 | Ta2O5 | 0.8295 | 55.30 |
| 20 | SiO2 | 0.8124 | 77.57 |
| 21 | Ta2O5 | 0.8402 | 56.01 |
| 22 | SiO2 | 0.8333 | 79.57 |
| 23 | Ta2O5 | 0.8466 | 58.44 |
| 24 | SiO2 | 0.8209 | 78.39 |
| 25 | Ta2O5 | 0.8324 | 55.49 |
| 26 | SiO2 | 0.8202 | 78.32 |
| 27 | Ta2O5 | 0.8441 | 56.27 |
| 28 | SiO2 | 0.8337 | 79.61 |
| 29 | Ta2O5 | 0.8420 | 56.13 |
| 30 | SiO2 | 0.8193 | 78.23 |
| 31 | Ta2O5 | 0.8345 | 55.63 |
| 32 | SiO2 | 0.8262 | 78.89 |
| 33 | Ta2O5 | 0.8475 | 56.50 |
| 34 | SiO2 | 0.8296 | 79.22 |
| 35 | Ta2O5 | 0.8385 | 55.90 |
| 36 | SiO2 | 0.8197 | 78.27 |
| 37 | Ta2O5 | 0.8379 | 55.86 |
| 38 | SiO2 | 0.8305 | 79.30 |
| 39 | Ta2O5 | 0.8472 | 56.48 |
| 40 | SiO2 | 0.8259 | 78.86 |
| 41 | Ta2O5 | 0.8363 | 55.75 |
| 42 | SiO2 | 0.8223 | 78.52 |
| 43 | Ta2O5 | 0.8424 | 56.16 |
| 44 | SiO2 | 0.8311 | 79.36 |
| 45 | Ta2O5 | 0.8432 | 56.21 |
| 46 | SiO2 | 0.8242 | 78.70 |
| 47 | Ta2O5 | 0.8375 | 55.83 |
| 48 | SiO2 | 0.8250 | 78.78 |
| 49 | Ta2O5 | 0.8439 | 56.26 |
| 50 | SiO2 | 0.8305 | 79.30 |
| 51 | Ta2O5 | 0.8417 | 56.11 |
| 52 | SiO2 | 0.8223 | 78.52 |
| 53 | Ta2O5 | 0.8391 | 55.94 |
| 54 | SiO2 | 0.8276 | 79.03 |
| 55 | Ta2O5 | 0.8445 | 56.30 |
| 56 | SiO2 | 0.8282 | 79.08 |
| 57 | Ta2O5 | 0.8402 | 56.01 |
| 58 | SiO2 | 0.8237 | 78.65 |
| 59 | Ta2O5 | 0.8405 | 56.03 |
| 60 | SiO2 | 0.8285 | 79.11 |
| 61 | Ta2O5 | 0.8447 | 56.31 |
| 62 | SiO2 | 0.8264 | 78.91 |
| 63 | Ta2O5 | 0.8391 | 55.94 |
| 64 | SiO2 | 0.8242 | 78.70 |
| 65 | Ta2O5 | 0.8433 | 56.22 |
| 66 | SiO2 | 0.8284 | 79.10 |
| 67 | Ta2O5 | 0.8436 | 56.24 |
| 68 | SiO2 | 0.8256 | 78.83 |
| 69 | Ta2O5 | 0.8382 | 55.88 |
| 70 | SiO2 | 0.8260 | 78.87 |
| 71 | Ta2O5 | 0.8445 | 56.30 |
| 72 | SiO2 | 0.8279 | 79.05 |
| 73 | Ta2O5 | 0.8424 | 56.16 |
| 74 | SiO2 | 0.8242 | 78.70 |
| 75 | Ta2O5 | 0.8400 | 56.00 |
| 76 | SiO2 | 0.8276 | 79.03 |
| 77 | Ta2O5 | 0.8445 | 56.30 |
| 78 | SiO2 | 0.8266 | 78.93 |
| 79 | Ta2O5 | 0.8402 | 56.01 |
| 80 | SiO2 | 0.8246 | 78.74 |
| 81 | Ta2O5 | 0.8432 | 56.21 |
| 82 | SiO2 | 0.8275 | 79.02 |
| 83 | Ta2O5 | 0.8429 | 56.19 |
| 84 | SiO2 | 0.8262 | 78.89 |
| 85 | Ta2O5 | 0.8402 | 56.01 |
| 86 | SiO2 | 0.8265 | 78.92 |
| 87 | Ta2O5 | 0.8417 | 56.11 |
| 88 | SiO2 | 0.8282 | 79.08 |
| 89 | Ta2O5 | 0.8435 | 56.23 |
| 90 | SiO2 | 0.8244 | 78.72 |
| 91 | Ta2O5 | 0.8399 | 55.99 |
| 92 | SiO2 | 0.8275 | 79.02 |
| 93 | Ta2O5 | 0.8436 | 56.24 |
| 94 | SiO2 | 0.8275 | 79.02 |
| 95 | Ta2O5 | 0.8403 | 56.02 |
| 96 | SiO2 | 0.8252 | 78.80 |
| 97 | Ta2O5 | 0.8423 | 56.15 |
| 98 | SiO2 | 0.8278 | 79.04 |
| 99 | Ta2O5 | 0.8426 | 56.17 |
| 100 | SiO2 | 0.8260 | 78.87 |
| 101 | Ta2O5 | 0.8405 | 56.03 |
| 102 | SiO2 | 0.8257 | 78.84 |
| 103 | Ta2O5 | 0.8444 | 56.29 |
| 104 | SiO2 | 0.8268 | 78.95 |
| 105 | Ta2O5 | 0.8414 | 56.09 |
| 106 | SiO2 | 0.8256 | 78.83 |
| 107 | Ta2O5 | 0.8412 | 56.08 |
| 108 | SiO2 | 0.8268 | 78.95 |
| 109 | Ta2O5 | 0.8433 | 56.22 |
| 110 | SiO2 | 0.8266 | 78.93 |
| 111 | Ta2O5 | 0.8409 | 56.06 |
| 112 | SiO2 | 0.8259 | 78.86 |
| 113 | Ta2O5 | 0.8424 | 56.16 |
| 114 | SiO2 | 0.8266 | 78.93 |
| 115 | Ta2O5 | 0.8424 | 56.16 |
| 116 | SiO2 | 0.8265 | 78.92 |
| 117 | Ta2O5 | 0.8406 | 56.04 |
| 118 | SiO2 | 0.8260 | 78.87 |
| 119 | Ta2O5 | 0.8426 | 56.17 |
| 120 | SiO2 | 0.8275 | 79.02 |
| 121 | Ta2O5 | 0.8421 | 56.14 |
| 122 | SiO2 | 0.8249 | 78.77 |
| 123 | Ta2O5 | 0.8405 | 56.03 |
| 124 | SiO2 | 0.8270 | 78.97 |
| 125 | Ta2O5 | 0.8424 | 56.16 |
| 126 | SiO2 | 0.8282 | 79.08 |
| 127 | Ta2O5 | 0.8400 | 56.00 |
| 128 | SiO2 | 0.8245 | 78.73 |
| 129 | Ta2O5 | 0.8421 | 56.14 |
| 130 | SiO2 | 0.8273 | 79.00 |
| 131 | Ta2O5 | 0.8432 | 56.21 |
| 132 | SiO2 | 0.8257 | 78.84 |
| 133 | Ta2O5 | 0.8397 | 55.98 |
| 134 | SiO2 | 0.8246 | 78.74 |
| 135 | Ta2O5 | 0.8429 | 56.19 |
| 136 | SiO2 | 0.8288 | 79.14 |
| 137 | Ta2O5 | 0.8412 | 56.08 |
| 138 | SiO2 | 0.8239 | 78.67 |
| 139 | Ta2O5 | 0.8403 | 56.02 |
| 140 | SiO2 | 0.8261 | 78.88 |
| 141 | Ta2O5 | 0.8423 | 56.15 |
| 142 | SiO2 | 0.8283 | 79.09 |
| 143 | Ta2O5 | 0.8409 | 56.06 |
| 144 | SiO2 | 0.8220 | 78.49 |
| 145 | Ta2O5 | 0.8396 | 55.97 |
| 146 | SiO2 | 0.8283 | 79.09 |
| 147 | Ta2O5 | 0.8441 | 56.27 |
| 148 | SiO2 | 0.8262 | 78.89 |
| 149 | Ta2O5 | 0.8379 | 55.86 |
| 150 | SiO2 | 0.8197 | 78.27 |
| 151 | Ta2O5 | 0.8429 | 56.19 |
| 152 | SiO2 | 0.8307 | 79.32 |
| 153 | Ta2O5 | 0.8420 | 56.13 |
| 154 | SiO2 | 0.8217 | 78.46 |

APPENDIX A-continued

| Layer # | Material | Optical Thickness | Metric Thickness (nm) |
|---|---|---|---|
| 155 | Ta2O5 | 0.8357 | 55.71 |
| 156 | SiO2 | 0.8223 | 78.52 |
| 157 | Ta2O5 | 0.8450 | 56.33 |
| 158 | SiO2 | 0.8308 | 79.33 |
| 159 | Ta2O5 | 0.8372 | 55.81 |
| 160 | SiO2 | 0.8161 | 77.93 |
| 161 | Ta2O5 | 0.8354 | 55.69 |
| 162 | SiO2 | 0.8263 | 78.90 |
| 163 | Ta2O5 | 0.8474 | 56.40 |
| 164 | SiO2 | 0.8253 | 78.81 |
| 165 | Ta2O5 | 0.8288 | 55.25 |
| 166 | SiO2 | 0.8103 | 77.37 |
| 167 | Ta2O5 | 0.8391 | 55.94 |
| 168 | SiO2 | 0.8318 | 79.43 |
| 169 | Ta2O5 | 0.8423 | 56.15 |
| 170 | SiO2 | 0.8083 | 77.18 |
| 171 | Ta2O5 | 0.8178 | 54.52 |
| 172 | SiO2 | 0.8087 | 77.22 |
| 173 | Ta2O5 | 0.8436 | 56.24 |
| 174 | SiO2 | 0.8224 | 78.53 |
| 175 | Ta2O5 | 0.8187 | 54.58 |
| 176 | SiO2 | 0.7696 | 73.49 |
| 177 | Ta2O5 | 0.8021 | 53.47 |
| 178 | SiO2 | 0.7686 | 73.39 |
| 179 | Ta2O5 | 0.7329 | 48.86 |
| 180 | SiO2 | 1.5674 | 149.67 |

APPENDIX B

| Layer # | Material | Optical Thickness | Metric Thickness (nm) |
|---|---|---|---|
| 1 | Ta2O5 | 1.5070 | 89.32 |
| 2 | SiO2 | 1.1544 | 98.77 |
| 3 | Ta2O5 | 1.3342 | 79.08 |
| 4 | SiO2 | 1.1510 | 98.48 |
| 5 | Ta2O5 | 1.1930 | 70.71 |
| 6 | SiO2 | 1.1508 | 98.46 |
| 7 | Ta2O5 | 1.2262 | 72.68 |
| 8 | SiO2 | 1.1508 | 98.46 |
| 9 | Ta2O5 | 1.1812 | 70.01 |
| 10 | SiO2 | 1.1501 | 98.40 |
| 11 | Ta2O5 | 1.1692 | 69.30 |
| 12 | SiO2 | 1.1503 | 98.42 |
| 13 | Ta2O5 | 1.1852 | 70.25 |
| 14 | SiO2 | 1.1503 | 98.42 |
| 15 | Ta2O5 | 1.1635 | 68.96 |
| 16 | SiO2 | 1.1500 | 98.39 |
| 17 | Ta2O5 | 1.1530 | 68.34 |
| 18 | SiO2 | 1.1501 | 98.40 |
| 19 | Ta2O5 | 1.1765 | 69.73 |
| 20 | SiO2 | 1.1503 | 98.42 |
| 21 | Ta2O5 | 1.1721 | 69.47 |
| 22 | SiO2 | 1.1500 | 98.39 |
| 23 | Ta2O5 | 1.1534 | 68.36 |
| 24 | SiO2 | 1.1500 | 98.39 |
| 25 | Ta2O5 | 1.1621 | 68.88 |
| 26 | SiO2 | 1.1501 | 98.40 |
| 27 | Ta2O5 | 1.1635 | 68.96 |
| 28 | SiO2 | 1.1500 | 98.39 |
| 29 | Ta2O5 | 1.1483 | 68.06 |
| 30 | SiO2 | 1.1500 | 98.39 |
| 31 | Ta2O5 | 1.1608 | 68.80 |
| 32 | SiO2 | 1.1501 | 98.40 |
| 33 | Ta2O5 | 1.1699 | 69.34 |
| 34 | SiO2 | 1.1501 | 98.40 |
| 35 | Ta2O5 | 1.1566 | 68.49 |
| 36 | SiO2 | 1.1500 | 98.39 |
| 37 | Ta2O5 | 1.1574 | 68.60 |
| 38 | SiO2 | 1.1501 | 98.40 |
| 39 | Ta2O5 | 1.1665 | 69.14 |
| 40 | SiO2 | 1.1501 | 98.40 |
| 41 | Ta2O5 | 1.1544 | 68.42 |
| 42 | SiO2 | 1.1499 | 98.38 |
| 43 | Ta2O5 | 1.1505 | 68.19 |
| 44 | SiO2 | 1.1500 | 98.39 |
| 45 | Ta2O5 | 1.1640 | 68.99 |
| 46 | SiO2 | 1.1501 | 98.40 |
| 47 | Ta2O5 | 1.1591 | 68.70 |
| 48 | SiO2 | 1.1500 | 98.39 |
| 49 | Ta2O5 | 1.1517 | 68.26 |
| 50 | SiO2 | 1.1500 | 98.39 |
| 51 | Ta2O5 | 1.1625 | 68.90 |
| 52 | SiO2 | 1.1501 | 98.40 |
| 53 | Ta2O5 | 1.1608 | 68.80 |
| 54 | SiO2 | 1.1500 | 98.39 |
| 55 | Ta2O5 | 1.1508 | 68.21 |
| 56 | SiO2 | 1.1500 | 98.39 |
| 57 | Ta2O5 | 1.1589 | 68.69 |
| 58 | SiO2 | 1.1501 | 98.40 |
| 59 | Ta2O5 | 1.1628 | 68.92 |
| 60 | SiO2 | 1.1500 | 98.39 |
| 61 | Ta2O5 | 1.1534 | 68.36 |
| 62 | SiO2 | 1.1500 | 98.39 |
| 63 | Ta2O5 | 1.1567 | 68.56 |
| 64 | SiO2 | 1.1500 | 98.39 |
| 65 | Ta2O5 | 1.1623 | 68.89 |
| 66 | SiO2 | 1.1500 | 98.39 |
| 67 | Ta2O5 | 1.1544 | 68.42 |
| 68 | SiO2 | 1.1500 | 98.39 |
| 69 | Ta2O5 | 1.1549 | 68.45 |
| 70 | SiO2 | 1.1500 | 98.39 |
| 71 | Ta2O5 | 1.1620 | 68.87 |
| 72 | SiO2 | 1.1500 | 98.39 |
| 73 | Ta2O5 | 1.1576 | 68.61 |
| 74 | SiO2 | 1.1500 | 98.39 |
| 75 | Ta2O5 | 1.1544 | 68.42 |
| 76 | SiO2 | 1.1500 | 98.39 |
| 77 | Ta2O5 | 1.1596 | 68.73 |
| 78 | SiO2 | 1.1500 | 98.39 |
| 79 | Ta2O5 | 1.1582 | 68.65 |
| 80 | SiO2 | 1.1500 | 98.39 |
| 81 | Ta2O5 | 1.1537 | 68.38 |
| 82 | SiO2 | 1.1500 | 98.39 |
| 83 | Ta2O5 | 1.1576 | 68.61 |
| 84 | SiO2 | 1.1500 | 98.39 |
| 85 | Ta2O5 | 1.1608 | 68.80 |
| 86 | SiO2 | 1.1500 | 98.39 |
| 87 | Ta2O5 | 1.1562 | 68.53 |
| 88 | SiO2 | 1.1500 | 98.39 |
| 89 | Ta2O5 | 1.1561 | 68.52 |
| 90 | SiO2 | 1.1500 | 98.39 |
| 91 | Ta2O5 | 1.1604 | 68.78 |
| 92 | SiO2 | 1.1500 | 98.39 |
| 93 | Ta2O5 | 1.1578 | 68.61 |
| 94 | SiO2 | 1.1500 | 98.39 |
| 95 | Ta2O5 | 1.1537 | 68.38 |
| 96 | SiO2 | 1.1500 | 98.39 |
| 97 | Ta2O5 | 1.1591 | 68.70 |
| 98 | SiO2 | 1.1501 | 98.40 |
| 99 | Ta2O5 | 1.1603 | 68.77 |
| 100 | SiO2 | 1.1500 | 98.39 |
| 101 | Ta2O5 | 1.1532 | 68.35 |
| 102 | SiO2 | 1.1500 | 98.39 |
| 103 | Ta2O5 | 1.1567 | 68.56 |
| 104 | SiO2 | 1.1501 | 98.40 |
| 105 | Ta2O5 | 1.1621 | 68.88 |
| 106 | SiO2 | 1.1500 | 98.39 |
| 107 | Ta2O5 | 1.1552 | 68.47 |
| 108 | SiO2 | 1.1500 | 98.39 |
| 109 | Ta2O5 | 1.1557 | 68.50 |
| 110 | SiO2 | 1.1500 | 98.39 |
| 111 | Ta2O5 | 1.1635 | 68.96 |
| 112 | SiO2 | 1.1501 | 98.40 |
| 113 | Ta2O5 | 1.1569 | 68.57 |
| 114 | SiO2 | 1.1500 | 98.39 |
| 115 | Ta2O5 | 1.1516 | 68.27 |
| 116 | SiO2 | 1.1500 | 98.39 |
| 117 | Ta2O5 | 1.1603 | 68.77 |
| 118 | SiO2 | 1.1501 | 98.40 |
| 119 | Ta2O5 | 1.1593 | 68.71 |
| 120 | SiO2 | 1.1500 | 98.39 |

APPENDIX B-continued

| Layer # | Material | Optical Thickness | Metric Thickness (nm) |
|---|---|---|---|
| 121 | Ta2O5 | 1.1530 | 68.34 |
| 122 | SiO2 | 1.1500 | 98.39 |
| 123 | Ta2O5 | 1.1608 | 68.80 |
| 124 | SiO2 | 1.1501 | 98.40 |
| 125 | Ta2O5 | 1.1640 | 68.99 |
| 126 | SiO2 | 1.1500 | 98.39 |
| 127 | Ta2O5 | 1.1539 | 68.39 |
| 128 | SiO2 | 1.1500 | 98.39 |
| 129 | Ta2O5 | 1.1569 | 68.57 |
| 130 | SiO2 | 1.1501 | 98.40 |
| 131 | Ta2O5 | 1.1642 | 69.00 |
| 132 | SiO2 | 1.1501 | 98.40 |
| 133 | Ta2O5 | 1.1562 | 68.53 |
| 134 | SiO2 | 1.1500 | 98.39 |
| 135 | Ta2O5 | 1.1554 | 68.48 |
| 136 | SiO2 | 1.1500 | 98.39 |
| 137 | Ta2O5 | 1.1643 | 69.01 |
| 138 | SiO2 | 1.1501 | 98.40 |
| 139 | Ta2O5 | 1.1579 | 68.63 |
| 140 | SiO2 | 1.1500 | 98.39 |
| 141 | Ta2O5 | 1.1513 | 68.24 |
| 142 | SiO2 | 1.1500 | 98.39 |
| 143 | Ta2O5 | 1.1626 | 68.91 |
| 144 | SiO2 | 1.1501 | 98.40 |
| 145 | Ta2O5 | 1.1665 | 69.14 |
| 146 | SiO2 | 1.1501 | 98.40 |
| 147 | Ta2O5 | 1.1576 | 68.61 |
| 148 | SiO2 | 1.1500 | 98.39 |
| 149 | Ta2O5 | 1.1643 | 69.01 |
| 150 | SiO2 | 1.1501 | 98.40 |
| 151 | Ta2O5 | 1.1687 | 69.27 |
| 152 | SiO2 | 1.1501 | 98.40 |
| 153 | Ta2O5 | 1.1520 | 68.28 |
| 154 | SiO2 | 1.1499 | 98.38 |
| 155 | Ta2O5 | 1.1569 | 68.57 |
| 156 | SiO2 | 1.1501 | 98.40 |
| 157 | Ta2O5 | 1.1758 | 69.69 |
| 158 | SiO2 | 1.1502 | 98.41 |
| 159 | Ta2O5 | 1.1685 | 69.26 |
| 160 | SiO2 | 1.1501 | 98.40 |
| 161 | Ta2O5 | 1.1655 | 69.08 |
| 162 | SiO2 | 1.1502 | 98.41 |
| 163 | Ta2O5 | 1.1812 | 70.01 |
| 164 | SiO2 | 1.1503 | 98.42 |
| 165 | Ta2O5 | 1.1739 | 69.58 |
| 166 | SiO2 | 1.1501 | 98.40 |
| 167 | Ta2O5 | 1.1716 | 69.44 |
| 168 | SiO2 | 1.1505 | 98.43 |
| 169 | Ta2O5 | 1.2062 | 71.49 |
| 170 | SiO2 | 1.1507 | 98.45 |
| 171 | Ta2O5 | 1.2025 | 71.27 |
| 172 | SiO2 | 1.1506 | 98.44 |
| 173 | Ta2O5 | 1.2021 | 71.25 |
| 174 | SiO2 | 1.1512 | 98.49 |
| 175 | Ta2O5 | 1.2828 | 76.03 |
| 176 | SiO2 | 1.1521 | 98.57 |
| 177 | Ta2O5 | 1.3081 | 77.53 |
| 178 | SiO2 | 1.1524 | 98.60 |
| 179 | Ta2O5 | 1.3750 | 81.50 |
| 180 | SiO2 | 0.5780 | 49.45 |

APPENDIX C 633 nm single-notch filter example
Total number of layers: 152
Reference wavelength: 632.8 nm

| Layer # | Material | Metric Thickness (nm) |
|---|---|---|
| 1 | Ta2O5 | 139.28811 |
| 2 | SiO2 | 213.911479 |
| 3 | Ta2O5 | 138.698607 |
| 4 | SiO2 | 222.923555 |
| 5 | Ta2O5 | 142.834465 |
| 6 | SiO2 | 224.190623 |
| 7 | Ta2O5 | 139.953649 |
| 8 | SiO2 | 222.700222 |
| 9 | Ta2O5 | 140.723242 |
| 10 | SiO2 | 225.591053 |
| 11 | Ta2O5 | 140.069792 |
| 12 | SiO2 | 226.494695 |
| 13 | Ta2O5 | 139.733658 |
| 14 | SiO2 | 230.057231 |
| 15 | Ta2O5 | 138.455212 |
| 16 | SiO2 | 230.012006 |
| 17 | Ta2O5 | 137.652405 |
| 18 | SiO2 | 231.491287 |
| 19 | Ta2O5 | 137.112544 |
| 20 | SiO2 | 230.898071 |
| 21 | Ta2O5 | 136.56315 |
| 22 | SiO2 | 232.401128 |
| 23 | Ta2O5 | 136.193571 |
| 24 | SiO2 | 233.290131 |
| 25 | Ta2O5 | 135.525826 |
| 26 | SiO2 | 234.138504 |
| 27 | Ta2O5 | 135.235488 |
| 28 | SiO2 | 234.436992 |
| 29 | Ta2O5 | 134.751592 |
| 30 | SiO2 | 234.215835 |
| 31 | Ta2O5 | 134.700197 |
| 32 | SiO2 | 235.215953 |
| 33 | Ta2O5 | 134.319285 |
| 34 | SiO2 | 235.23197 |
| 35 | Ta2O5 | 134.141431 |
| 36 | SiO2 | 236.26591 |
| 37 | Ta2O5 | 133.852823 |
| 38 | SiO2 | 235.692752 |
| 39 | Ta2O5 | 133.791075 |
| 40 | SiO2 | 236.227239 |
| 41 | Ta2O5 | 133.634831 |
| 42 | SiO2 | 236.023971 |
| 43 | Ta2O5 | 133.498929 |
| 44 | SiO2 | 236.819458 |
| 45 | Ta2O5 | 133.389332 |
| 46 | SiO2 | 236.800651 |
| 47 | Ta2O5 | 133.236556 |
| 48 | SiO2 | 236.754549 |
| 49 | Ta2O5 | 133.258851 |
| 50 | SiO2 | 236.738611 |
| 51 | Ta2O5 | 133.165059 |
| 52 | SiO2 | 236.713197 |
| 53 | Ta2O5 | 133.1584 |
| 54 | SiO2 | 237.328616 |
| 55 | Ta2O5 | 133.033007 |
| 56 | SiO2 | 237.0356 |
| 57 | Ta2O5 | 133.04785 |
| 58 | SiO2 | 237.337405 |
| 59 | Ta2O5 | 132.968077 |
| 60 | SiO2 | 236.786098 |
| 61 | Ta2O5 | 132.962244 |
| 62 | SiO2 | 237.399614 |
| 63 | Ta2O5 | 132.890701 |
| 64 | SiO2 | 237.228576 |
| 65 | Ta2O5 | 132.901903 |
| 66 | SiO2 | 237.587371 |
| 67 | Ta2O5 | 132.884176 |
| 68 | SiO2 | 237.211067 |
| 69 | Ta2O5 | 132.866745 |
| 70 | SiO2 | 237.156016 |
| 71 | Ta2O5 | 132.8752 |
| 72 | SiO2 | 237.333498 |
| 73 | Ta2O5 | 132.832563 |
| 74 | SiO2 | 237.392681 |
| 75 | Ta2O5 | 132.885776 |
| 76 | SiO2 | 237.666196 |
| 77 | Ta2O5 | 132.834586 |
| 78 | SiO2 | 237.116806 |
| 79 | Ta2O5 | 132.858486 |

APPENDIX C-continued 633 nm single-notch filter example
Total number of layers: 152
Reference wavelength: 632.8 nm

| Layer # | Material | Metric Thickness (nm) |
|---|---|---|
| 80 | SiO2 | 237.326207 |
| 81 | Ta2O5 | 132.83121 |
| 82 | SiO2 | 237.021654 |
| 83 | Ta2O5 | 132.902491 |
| 84 | SiO2 | 237.650372 |
| 85 | Ta2O5 | 132.904564 |
| 86 | SiO2 | 237.21769 |
| 87 | Ta2O5 | 132.926435 |
| 88 | SiO2 | 237.306033 |
| 89 | Ta2O5 | 132.918344 |
| 90 | SiO2 | 236.899546 |
| 91 | Ta2O5 | 132.965657 |
| 92 | SiO2 | 237.091782 |
| 93 | Ta2O5 | 133.046134 |
| 94 | SiO2 | 237.269179 |
| 95 | Ta2O5 | 133.067987 |
| 96 | SiO2 | 237.056435 |
| 97 | Ta2O5 | 133.103914 |
| 98 | SiO2 | 237.000356 |
| 99 | Ta2O5 | 133.073437 |
| 100 | SiO2 | 236.439923 |
| 101 | Ta2O5 | 133.217288 |
| 102 | SiO2 | 236.905146 |
| 103 | Ta2O5 | 133.335387 |
| 104 | SiO2 | 236.553741 |
| 105 | Ta2O5 | 133.463364 |
| 106 | SiO2 | 236.834114 |
| 107 | Ta2O5 | 133.484189 |
| 108 | SiO2 | 235.9224 |
| 109 | Ta2O5 | 133.581673 |
| 110 | SiO2 | 235.998739 |
| 111 | Ta2O5 | 133.725284 |
| 112 | SiO2 | 235.754216 |
| 113 | Ta2O5 | 133.941867 |
| 114 | SiO2 | 235.94738 |
| 115 | Ta2O5 | 134.182591 |
| 116 | SiO2 | 235.531469 |
| 117 | Ta2O5 | 134.219385 |
| 118 | SiO2 | 234.742682 |
| 119 | Ta2O5 | 134.41059 |
| 120 | SiO2 | 234.584301 |
| 121 | Ta2O5 | 134.738459 |
| 122 | SiO2 | 234.055298 |
| 123 | Ta2O5 | 135.211026 |
| 124 | SiO2 | 234.545358 |
| 125 | Ta2O5 | 135.481658 |
| 126 | SiO2 | 233.143237 |
| 127 | Ta2O5 | 135.728033 |
| 128 | SiO2 | 232.701538 |
| 129 | Ta2O5 | 136.048534 |
| 130 | SiO2 | 231.152273 |
| 131 | Ta2O5 | 136.595729 |
| 132 | SiO2 | 231.748662 |
| 133 | Ta2O5 | 137.530855 |
| 134 | SiO2 | 230.960454 |
| 135 | Ta2O5 | 137.947255 |
| 136 | SiO2 | 230.072331 |
| 137 | Ta2O5 | 138.451153 |
| 138 | SiO2 | 227.742065 |
| 139 | Ta2O5 | 138.497134 |
| 140 | SiO2 | 225.988236 |
| 141 | Ta2O5 | 140.177979 |
| 142 | SiO2 | 226.801241 |
| 143 | Ta2O5 | 141.49776 |
| 144 | SiO2 | 226.145332 |
| 145 | Ta2O5 | 143.665141 |
| 146 | SiO2 | 228.484731 |
| 147 | Ta2O5 | 144.557317 |
| 148 | SiO2 | 223.516892 |
| 149 | Ta2O5 | 145.28608 |
| 150 | SiO2 | 228.838173 |
| 151 | Ta2O5 | 146.633943 |
| 152 | SiO2 | 112.925644 |

APPENDIX D

Triple Notch Filter - Example 1
Total number of layers: 120

| Layer # | Material | Metric Thickness (nm) |
|---|---|---|
| 1 | Ta2O5 | 151.12 |
| 2 | SiO2 | 217 |
| 3 | Ta2O5 | 171.64 |
| 4 | SiO2 | 229.88 |
| 5 | Ta2O5 | 173.23 |
| 6 | SiO2 | 201.44 |
| 7 | Ta2O5 | 183.5 |
| 8 | SiO2 | 270.79 |
| 9 | Ta2O5 | 145.34 |
| 10 | SiO2 | 233.66 |
| 11 | Ta2O5 | 151.48 |
| 12 | SiO2 | 288.84 |
| 13 | Ta2O5 | 182.25 |
| 14 | SiO2 | 170.12 |
| 15 | Ta2O5 | 203.39 |
| 16 | SiO2 | 226.94 |
| 17 | Ta2O5 | 180.4 |
| 18 | SiO2 | 263.07 |
| 19 | Ta2O5 | 120.98 |
| 20 | SiO2 | 92.79 |
| 21 | Ta2O5 | 194.26 |
| 22 | SiO2 | 248.44 |
| 23 | Ta2O5 | 147.55 |
| 24 | SiO2 | 364.18 |
| 25 | Ta2O5 | 80.89 |
| 26 | SiO2 | 283.31 |
| 27 | Ta2O5 | 179.72 |
| 28 | SiO2 | 160.01 |
| 29 | Ta2O5 | 102.43 |
| 30 | SiO2 | 171.99 |
| 31 | Ta2O5 | 203.75 |
| 32 | SiO2 | 292.8 |
| 33 | Ta2O5 | 193.03 |
| 34 | SiO2 | 142.13 |
| 35 | Ta2O5 | 119.82 |
| 36 | SiO2 | 367.16 |
| 37 | Ta2O5 | 179.8 |
| 38 | SiO2 | 96.24 |
| 39 | Ta2O5 | 205.85 |
| 40 | SiO2 | 172.98 |
| 41 | Ta2O5 | 170.21 |
| 42 | SiO2 | 236.3 |
| 43 | Ta2O5 | 54.01 |
| 44 | SiO2 | 259.02 |
| 45 | Ta2O5 | 97.77 |
| 46 | SiO2 | 141.69 |
| 47 | Ta2O5 | 175.48 |
| 48 | SiO2 | 143.74 |
| 49 | Ta2O5 | 152.44 |
| 50 | SiO2 | 256.19 |
| 51 | Ta2O5 | 186.63 |
| 52 | SiO2 | 169.46 |
| 53 | Ta2O5 | 66.38 |
| 54 | SiO2 | 95.6 |
| 55 | Ta2O5 | 171.86 |
| 56 | SiO2 | 130.02 |
| 57 | Ta2O5 | 123.68 |
| 58 | SiO2 | 354.01 |
| 59 | Ta2O5 | 219.38 |
| 60 | SiO2 | 86.66 |

APPENDIX D-continued

Triple Notch Filter - Example 1
Total number of layers: 120

| Layer # | Material | Metric Thickness (nm) |
|---|---|---|
| 61 | Ta2O5 | 200.09 |
| 62 | SiO2 | 95.49 |
| 63 | Ta2O5 | 128.88 |
| 64 | SiO2 | 252.19 |
| 65 | Ta2O5 | 155.48 |
| 66 | SiO2 | 78.93 |
| 67 | Ta2O5 | 193.21 |
| 68 | SiO2 | 109.59 |
| 69 | Ta2O5 | 227.4 |
| 70 | SiO2 | 108.66 |
| 71 | Ta2O5 | 181.63 |
| 72 | SiO2 | 235.01 |
| 73 | Ta2O5 | 178.47 |
| 74 | SiO2 | 157 |
| 75 | Ta2O5 | 209.59 |
| 76 | SiO2 | 97.4 |
| 77 | Ta2O5 | 65.33 |
| 78 | SiO2 | 239.19 |
| 79 | Ta2O5 | 119.79 |
| 80 | SiO2 | 143.37 |
| 81 | Ta2O5 | 122.2 |
| 82 | SiO2 | 294.51 |
| 83 | Ta2O5 | 205.8 |
| 84 | SiO2 | 99.03 |
| 85 | Ta2O5 | 211.92 |
| 86 | SiO2 | 340.42 |
| 87 | Ta2O5 | 141.04 |
| 88 | SiO2 | 275.84 |
| 89 | Ta2O5 | 200.67 |
| 90 | SiO2 | 99.19 |
| 91 | Ta2O5 | 103.35 |
| 92 | SiO2 | 290.15 |
| 93 | Ta2O5 | 179.76 |
| 94 | SiO2 | 227.27 |
| 95 | Ta2O5 | 196.98 |
| 96 | SiO2 | 151.68 |
| 97 | Ta2O5 | 205.66 |
| 98 | SiO2 | 93.75 |
| 99 | Ta2O5 | 193.92 |
| 100 | SiO2 | 210.8 |
| 101 | Ta2O5 | 147.71 |
| 102 | SiO2 | 178.36 |
| 103 | Ta2O5 | 107.16 |
| 104 | SiO2 | 92.93 |
| 105 | Ta2O5 | 202.39 |
| 106 | SiO2 | 265.16 |
| 107 | Ta2O5 | 116.18 |
| 108 | SiO2 | 130.33 |
| 109 | Ta2O5 | 143.89 |
| 110 | SiO2 | 250.52 |
| 111 | Ta2O5 | 196.66 |
| 112 | SiO2 | 356.2 |
| 113 | Ta2O5 | 180.33 |
| 114 | SiO2 | 415.76 |
| 115 | Ta2O5 | 155.37 |
| 116 | SiO2 | 189.38 |
| 117 | Ta2O5 | 100.78 |
| 118 | SiO2 | 205.98 |
| 119 | Ta2O5 | 94.38 |
| 120 | SiO2 | 78.28 |

APPENDIX E

Triple Notch Filter - Example 2

| Layer # | Material | Metric Thickness (nm) |
|---|---|---|
| Side 1 Coating (dual-notch filter coating): Total number of layers: 182 | | |
| 1 | Ta2O5 | 114.153439 |
| 2 | SiO2 | 157.717654 |
| 3 | Ta2O5 | 93.775614 |
| 4 | SiO2 | 151.16149 |
| 5 | Ta2O5 | 94.674041 |
| 6 | SiO2 | 153.177853 |
| 7 | Ta2O5 | 103.330594 |
| 8 | SiO2 | 136.813886 |
| 9 | Ta2O5 | 123.221684 |
| 10 | SiO2 | 170.165231 |
| 11 | Ta2O5 | 131.802866 |
| 12 | SiO2 | 183.052286 |
| 13 | Ta2O5 | 113.731231 |
| 14 | SiO2 | 190.263665 |
| 15 | Ta2O5 | 109.033293 |
| 16 | SiO2 | 197.218221 |
| 17 | Ta2O5 | 117.499573 |
| 18 | SiO2 | 177.377991 |
| 19 | Ta2O5 | 128.187949 |
| 20 | SiO2 | 153.245943 |
| 21 | Ta2O5 | 138.270341 |
| 22 | SiO2 | 156.06567 |
| 23 | Ta2O5 | 138.799491 |
| 24 | SiO2 | 175.892865 |
| 25 | Ta2O5 | 111.031003 |
| 26 | SiO2 | 176.275269 |
| 27 | Ta2O5 | 108.18978 |
| 28 | SiO2 | 69.395768 |
| 29 | Ta2O5 | 125.750681 |
| 30 | SiO2 | 161.92254 |
| 31 | Ta2O5 | 80.222207 |
| 32 | SiO2 | 156.885469 |
| 33 | Ta2O5 | 82.843287 |
| 34 | SiO2 | 177.228343 |
| 35 | Ta2O5 | 105.576423 |
| 36 | SiO2 | 108.649611 |
| 37 | Ta2O5 | 133.440193 |
| 38 | SiO2 | 150.061469 |
| 39 | Ta2O5 | 99.706309 |
| 40 | SiO2 | 159.044032 |
| 41 | Ta2O5 | 142.29338 |
| 42 | SiO2 | 260.832475 |
| 43 | Ta2O5 | 100.621191 |
| 44 | SiO2 | 204.029954 |
| 45 | Ta2O5 | 138.556941 |
| 46 | SiO2 | 197.31996 |
| 47 | Ta2O5 | 119.275496 |
| 48 | SiO2 | 79.241534 |
| 49 | Ta2O5 | 38.649707 |
| 50 | SiO2 | 194.279972 |
| 51 | Ta2O5 | 117.970841 |
| 52 | SiO2 | 101.317606 |
| 53 | Ta2O5 | 116.649342 |
| 54 | SiO2 | 86.423162 |
| 55 | Ta2O5 | 106.866918 |
| 56 | SiO2 | 171.463451 |
| 57 | Ta2O5 | 88.669544 |
| 58 | SiO2 | 94.453435 |
| 59 | Ta2O5 | 123.339871 |
| 60 | SiO2 | 178.026171 |
| 61 | Ta2O5 | 126.463133 |
| 62 | SiO2 | 216.184838 |
| 63 | Ta2O5 | 96.986333 |
| 64 | SiO2 | 221.49827 |
| 65 | Ta2O5 | 98.358886 |
| 66 | SiO2 | 165.895218 |
| 67 | Ta2O5 | 105.83176 |
| 68 | SiO2 | 166.715711 |
| 69 | Ta2O5 | 62.200485 |
| 70 | SiO2 | 141.712221 |
| 71 | Ta2O5 | 142.288195 |
| 72 | SiO2 | 276.477646 |

APPENDIX E-continued

Triple Notch Filter - Example 2

| Layer # | Material | Metric Thickness (nm) |
|---|---|---|
| 73 | Ta2O5 | 105.035264 |
| 74 | SiO2 | 128.703943 |
| 75 | Ta2O5 | 90.234135 |
| 76 | SiO2 | 177.307184 |
| 77 | Ta2O5 | 89.075119 |
| 78 | SiO2 | 90.540569 |
| 79 | Ta2O5 | 101.505992 |
| 80 | SiO2 | 159.415818 |
| 81 | Ta2O5 | 97.202491 |
| 82 | SiO2 | 175.720535 |
| 83 | Ta2O5 | 37.388654 |
| 84 | SiO2 | 151.427469 |
| 85 | Ta2O5 | 142.952872 |
| 86 | SiO2 | 138.37107 |
| 87 | Ta2O5 | 139.214391 |
| 88 | SiO2 | 161.411918 |
| 89 | Ta2O5 | 97.112001 |
| 90 | SiO2 | 129.914329 |
| 91 | Ta2O5 | 134.878447 |
| 92 | SiO2 | 133.556056 |
| 93 | Ta2O5 | 172.842172 |
| 94 | SiO2 | 165.902157 |
| 95 | Ta2O5 | 109.01547 |
| 96 | SiO2 | 179.235282 |
| 97 | Ta2O5 | 93.081471 |
| 98 | SiO2 | 235.132262 |
| 99 | Ta2O5 | 94.507558 |
| 100 | SiO2 | 180.248743 |
| 101 | Ta2O5 | 103.966842 |
| 102 | SiO2 | 151.429185 |
| 103 | Ta2O5 | 89.321644 |
| 104 | SiO2 | 218.852726 |
| 105 | Ta2O5 | 99.344103 |
| 106 | SiO2 | 197.235949 |
| 107 | Ta2O5 | 88.921128 |
| 108 | SiO2 | 148.713969 |
| 109 | Ta2O5 | 83.639602 |
| 110 | SiO2 | 142.596972 |
| 111 | Ta2O5 | 122.495755 |
| 112 | SiO2 | 108.518164 |
| 113 | Ta2O5 | 74.482388 |
| 114 | SiO2 | 143.88971 |
| 115 | Ta2O5 | 109.781714 |
| 116 | SiO2 | 133.173706 |
| 117 | Ta2O5 | 115.265969 |
| 118 | SiO2 | 78.616539 |
| 119 | Ta2O5 | 105.110668 |
| 120 | SiO2 | 215.958027 |
| 121 | Ta2O5 | 37.701767 |
| 122 | SiO2 | 164.218016 |
| 123 | Ta2O5 | 128.468658 |
| 124 | SiO2 | 171.639224 |
| 125 | Ta2O5 | 94.15999 |
| 126 | SiO2 | 120.467284 |
| 127 | Ta2O5 | 126.390211 |
| 128 | SiO2 | 139.13556 |
| 129 | Ta2O5 | 61.089981 |
| 130 | SiO2 | 146.147387 |
| 131 | Ta2O5 | 96.952437 |
| 132 | SiO2 | 138.688893 |
| 133 | Ta2O5 | 109.292782 |
| 134 | SiO2 | 122.811223 |
| 135 | Ta2O5 | 68.085994 |
| 136 | SiO2 | 136.051226 |
| 137 | Ta2O5 | 116.260881 |
| 138 | SiO2 | 124.50687 |
| 139 | Ta2O5 | 89.970705 |
| 140 | SiO2 | 142.168433 |
| 141 | Ta2O5 | 69.084155 |
| 142 | SiO2 | 148.777999 |
| 143 | Ta2O5 | 131.197681 |
| 144 | SiO2 | 60.311187 |
| 145 | Ta2O5 | 96.187059 |
| 146 | SiO2 | 123.528594 |
| 147 | Ta2O5 | 102.422788 |
| 148 | SiO2 | 128.350868 |
| 149 | Ta2O5 | 108.014485 |
| 150 | SiO2 | 128.522579 |
| 151 | Ta2O5 | 76.936842 |
| 152 | SiO2 | 117.161904 |
| 153 | Ta2O5 | 112.360414 |
| 154 | SiO2 | 137.892631 |
| 155 | Ta2O5 | 85.703113 |
| 156 | SiO2 | 139.033299 |
| 157 | Ta2O5 | 82.154875 |
| 158 | SiO2 | 125.658942 |
| 159 | Ta2O5 | 111.108391 |
| 160 | SiO2 | 141.083905 |
| 161 | Ta2O5 | 70.362136 |
| 162 | SiO2 | 136.557935 |
| 163 | Ta2O5 | 95.533347 |
| 164 | SiO2 | 134.59897 |
| 165 | Ta2O5 | 100.468621 |
| 166 | SiO2 | 138.552046 |
| 167 | Ta2O5 | 75.619664 |
| 168 | SiO2 | 130.234071 |
| 169 | Ta2O5 | 104.758228 |
| 170 | SiO2 | 140.001703 |
| 171 | Ta2O5 | 87.542283 |
| 172 | SiO2 | 140.070545 |
| 173 | Ta2O5 | 84.584695 |
| 174 | SiO2 | 142.914639 |
| 175 | Ta2O5 | 105.431785 |
| 176 | SiO2 | 130.68232 |
| 177 | Ta2O5 | 91.421305 |
| 178 | SiO2 | 154.264364 |
| 179 | Ta2O5 | 111.859298 |
| 180 | SiO2 | 171.979159 |
| 181 | Ta2O5 | 128.597735 |
| 182 | SiO2 | 88.984374 |

Side 2 Coating (LWP coating):
Total number of layers: 92

| Layer # | Material | Metric Thickness (nm) |
|---|---|---|
| 1 | Ta2O5 | 116.088031 |
| 2 | SiO2 | 156.080041 |
| 3 | Ta2O5 | 106.596232 |
| 4 | SiO2 | 200.382664 |
| 5 | Ta2O5 | 28.199931 |
| 6 | SiO2 | 62.137413 |
| 7 | Ta2O5 | 41.708366 |
| 8 | SiO2 | 42.343909 |
| 9 | Ta2O5 | 51.054043 |
| 10 | SiO2 | 59.506799 |
| 11 | Ta2O5 | 35.932895 |
| 12 | SiO2 | 54.587367 |
| 13 | Ta2O5 | 50.349591 |
| 14 | SiO2 | 61.44422 |
| 15 | Ta2O5 | 36.083168 |
| 16 | SiO2 | 50.886042 |
| 17 | Ta2O5 | 54.096038 |
| 18 | SiO2 | 56.61749 |
| 19 | Ta2O5 | 35.224914 |
| 20 | SiO2 | 60.09087 |
| 21 | Ta2O5 | 48.702367 |
| 22 | SiO2 | 58.717084 |
| 23 | Ta2O5 | 37.691627 |
| 24 | SiO2 | 56.469018 |
| 25 | Ta2O5 | 49.794435 |
| 26 | SiO2 | 55.675671 |
| 27 | Ta2O5 | 36.44051 |
| 28 | SiO2 | 58.416781 |
| 29 | Ta2O5 | 52.889348 |
| 30 | SiO2 | 55.277351 |
| 31 | Ta2O5 | 37.091512 |
| 32 | SiO2 | 59.219815 |
| 33 | Ta2O5 | 48.714621 |
| 34 | SiO2 | 55.366964 |
| 35 | Ta2O5 | 36.672424 |
| 36 | SiO2 | 62.401163 |
| 37 | Ta2O5 | 48.715399 |

APPENDIX E-continued

Triple Notch Filter - Example 2

| Layer # | Material | Metric Thickness (nm) |
|---|---|---|
| 38 | SiO2 | 53.696184 |
| 39 | Ta2O5 | 39.799015 |
| 40 | SiO2 | 59.798715 |
| 41 | Ta2O5 | 49.008374 |
| 42 | SiO2 | 52.094972 |
| 43 | Ta2O5 | 38.641915 |
| 44 | SiO2 | 61.044881 |
| 45 | Ta2O5 | 46.880749 |
| 46 | SiO2 | 58.897418 |
| 47 | Ta2O5 | 37.976951 |
| 48 | SiO2 | 59.908084 |
| 49 | Ta2O5 | 47.700491 |
| 50 | SiO2 | 55.525992 |
| 51 | Ta2O5 | 36.49871 |
| 52 | SiO2 | 62.877184 |
| 53 | Ta2O5 | 49.532916 |
| 54 | SiO2 | 50.960957 |
| 55 | Ta2O5 | 40.054229 |
| 56 | SiO2 | 63.001077 |
| 57 | Ta2O5 | 46.502656 |
| 58 | SiO2 | 55.825009 |
| 59 | Ta2O5 | 35.497826 |
| 60 | SiO2 | 66.045386 |
| 61 | Ta2O5 | 45.688436 |
| 62 | SiO2 | 53.864834 |
| 63 | Ta2O5 | 40.834133 |
| 64 | SiO2 | 62.032116 |
| 65 | Ta2O5 | 45.704171 |
| 66 | SiO2 | 54.643351 |
| 67 | Ta2O5 | 37.651991 |
| 68 | SiO2 | 63.758016 |
| 69 | Ta2O5 | 46.395918 |
| 70 | SiO2 | 54.935054 |
| 71 | Ta2O5 | 37.056207 |
| 72 | SiO2 | 64.475794 |
| 73 | Ta2O5 | 48.996168 |
| 74 | SiO2 | 50.792097 |
| 75 | Ta2O5 | 37.019818 |
| 76 | SiO2 | 65.188044 |
| 77 | Ta2O5 | 47.744456 |
| 78 | SiO2 | 48.824458 |
| 79 | Ta2O5 | 37.772169 |
| 80 | SiO2 | 69.082305 |
| 81 | Ta2O5 | 50.798138 |
| 82 | SiO2 | 36.906081 |
| 83 | Ta2O5 | 41.827675 |
| 84 | SiO2 | 72.011966 |
| 85 | Ta2O5 | 45.644578 |
| 86 | SiO2 | 27.997071 |
| 87 | Ta2O5 | 52.947732 |
| 88 | SiO2 | 86.408622 |
| 89 | Ta2O5 | 21.662357 |
| 90 | SiO2 | 41.675003 |
| 91 | Ta2O5 | 63.907358 |
| 92 | SiO2 | 88.987848 |

APPENDIX F

45 Degree Single Notch Filter Example
Total number of layers: 186
Total metric thickness: 31.5 μm
Reference wavelength: 532.0 nm

| Layer # | Material | Metric Thickness (nm) |
|---|---|---|
| 1 | Ti2O5 | 123.60 |
| 2 | SiO2 | 203.72 |
| 3 | Ti2O5 | 123.36 |
| 4 | SiO2 | 209.59 |
| 5 | Ti2O5 | 126.07 |
| 6 | SiO2 | 209.34 |
| 7 | Ti2O5 | 123.84 |
| 8 | SiO2 | 207.84 |
| 9 | Ti2O5 | 125.09 |
| 10 | SiO2 | 212.20 |
| 11 | Ti2O5 | 125.77 |
| 12 | SiO2 | 213.54 |
| 13 | Ti2O5 | 125.30 |
| 14 | SiO2 | 215.37 |
| 15 | Ti2O5 | 124.23 |
| 16 | SiO2 | 214.55 |
| 17 | Ti2O5 | 123.32 |
| 18 | SiO2 | 214.94 |
| 19 | Ti2O5 | 123.38 |
| 20 | SiO2 | 215.84 |
| 21 | Ti2O5 | 123.16 |
| 22 | SiO2 | 216.67 |
| 23 | Ti2O5 | 122.92 |
| 24 | SiO2 | 217.79 |
| 25 | Ti2O5 | 122.17 |
| 26 | SiO2 | 217.20 |
| 27 | Ti2O5 | 121.85 |
| 28 | SiO2 | 217.86 |
| 29 | Ti2O5 | 121.85 |
| 30 | SiO2 | 218.04 |
| 31 | Ti2O5 | 121.73 |
| 32 | SiO2 | 219.12 |
| 33 | Ti2O5 | 121.41 |
| 34 | SiO2 | 219.14 |
| 35 | Ti2O5 | 120.98 |
| 36 | SiO2 | 218.93 |
| 37 | Ti2O5 | 120.93 |
| 38 | SiO2 | 219.38 |
| 39 | Ti2O5 | 120.91 |
| 40 | SiO2 | 219.61 |
| 41 | Ti2O5 | 120.87 |
| 42 | SiO2 | 220.41 |
| 43 | Ti2O5 | 120.54 |
| 44 | SiO2 | 219.95 |
| 45 | Ti2O5 | 120.34 |
| 46 | SiO2 | 220.12 |
| 47 | Ti2O5 | 120.40 |
| 48 | SiO2 | 220.20 |
| 49 | Ti2O5 | 120.43 |
| 50 | SiO2 | 220.68 |
| 51 | Ti2O5 | 120.30 |
| 52 | SiO2 | 220.81 |
| 53 | Ti2O5 | 120.06 |
| 54 | SiO2 | 220.50 |
| 55 | Ti2O5 | 120.09 |
| 56 | SiO2 | 220.71 |
| 57 | Ti2O5 | 120.14 |
| 58 | SiO2 | 220.72 |
| 59 | Ti2O5 | 120.11 |
| 60 | SiO2 | 221.29 |
| 61 | Ti2O5 | 119.97 |
| 62 | SiO2 | 220.83 |
| 63 | Ti2O5 | 119.88 |
| 64 | SiO2 | 220.84 |
| 65 | Ti2O5 | 119.91 |
| 66 | SiO2 | 221.00 |
| 67 | Ti2O5 | 120.02 |
| 68 | SiO2 | 221.17 |
| 69 | Ti2O5 | 119.90 |
| 70 | SiO2 | 221.37 |
| 71 | Ti2O5 | 119.70 |
| 72 | SiO2 | 220.89 |
| 73 | Ti2O5 | 119.74 |
| 74 | SiO2 | 221.25 |
| 75 | Ti2O5 | 119.88 |
| 76 | SiO2 | 221.18 |
| 77 | Ti2O5 | 119.91 |
| 78 | SiO2 | 221.56 |
| 79 | Ti2O5 | 119.76 |

APPENDIX F-continued

45 Degree Single Notch Filter Example
Total number of layers: 186
Total metric thickness: 31.5 μm
Reference wavelength: 532.0 nm

| Layer # | Material | Metric Thickness (nm) |
|---|---|---|
| 80 | SiO2 | 221.26 |
| 81 | Ti2O5 | 119.68 |
| 82 | SiO2 | 221.06 |
| 83 | Ti2O5 | 119.78 |
| 84 | SiO2 | 221.28 |
| 85 | Ti2O5 | 119.84 |
| 86 | SiO2 | 221.33 |
| 87 | Ti2O5 | 119.77 |
| 88 | SiO2 | 221.55 |
| 89 | Ti2O5 | 119.65 |
| 90 | SiO2 | 221.08 |
| 91 | Ti2O5 | 119.67 |
| 92 | SiO2 | 221.32 |
| 93 | Ti2O5 | 119.76 |
| 94 | SiO2 | 221.23 |
| 95 | Ti2O5 | 119.82 |
| 96 | SiO2 | 221.50 |
| 97 | Ti2O5 | 119.78 |
| 98 | SiO2 | 221.47 |
| 99 | Ti2O5 | 119.68 |
| 100 | SiO2 | 221.13 |
| 101 | Ti2O5 | 119.72 |
| 102 | SiO2 | 221.24 |
| 103 | Ti2O5 | 119.82 |
| 104 | SiO2 | 221.23 |
| 105 | Ti2O5 | 119.89 |
| 106 | SiO2 | 221.60 |
| 107 | Ti2O5 | 119.73 |
| 108 | SiO2 | 221.02 |
| 109 | Ti2O5 | 119.67 |
| 110 | SiO2 | 221.05 |
| 111 | Ti2O5 | 119.82 |
| 112 | SiO2 | 221.11 |
| 113 | Ti2O5 | 120.00 |
| 114 | SiO2 | 221.27 |
| 115 | Ti2O5 | 119.87 |
| 116 | SiO2 | 221.27 |
| 117 | Ti2O5 | 119.78 |
| 118 | SiO2 | 220.85 |
| 119 | Ti2O5 | 119.83 |
| 120 | SiO2 | 221.11 |
| 121 | Ti2O5 | 119.99 |
| 122 | SiO2 | 220.89 |
| 123 | Ti2O5 | 120.04 |
| 124 | SiO2 | 221.30 |
| 125 | Ti2O5 | 119.99 |
| 126 | SiO2 | 220.81 |
| 127 | Ti2O5 | 119.91 |
| 128 | SiO2 | 220.55 |
| 129 | Ti2O5 | 120.07 |
| 130 | SiO2 | 220.76 |
| 131 | Ti2O5 | 120.23 |
| 132 | SiO2 | 220.86 |
| 133 | Ti2O5 | 120.29 |
| 134 | SiO2 | 220.79 |
| 135 | Ti2O5 | 120.09 |
| 136 | SiO2 | 220.09 |
| 137 | Ti2O5 | 120.22 |
| 138 | SiO2 | 220.34 |
| 139 | Ti2O5 | 120.50 |
| 140 | SiO2 | 220.26 |
| 141 | Ti2O5 | 120.60 |
| 142 | SiO2 | 220.43 |
| 143 | Ti2O5 | 120.55 |
| 144 | SiO2 | 219.83 |
| 145 | Ti2O5 | 120.53 |
| 146 | SiO2 | 219.37 |
| 147 | Ti2O5 | 120.79 |
| 148 | SiO2 | 219.55 |
| 149 | Ti2O5 | 121.13 |
| 150 | SiO2 | 219.40 |
| 151 | Ti2O5 | 121.27 |
| 152 | SiO2 | 219.46 |
| 153 | Ti2O5 | 121.17 |
| 154 | SiO2 | 218.22 |
| 155 | Ti2O5 | 121.30 |
| 156 | SiO2 | 218.14 |
| 157 | Ti2O5 | 121.87 |
| 158 | SiO2 | 218.01 |
| 159 | Ti2O5 | 122.23 |
| 160 | SiO2 | 218.04 |
| 161 | Ti2O5 | 122.39 |
| 162 | SiO2 | 217.18 |
| 163 | Ti2O5 | 122.25 |
| 164 | SiO2 | 215.81 |
| 165 | Ti2O5 | 122.74 |
| 166 | SiO2 | 215.99 |
| 167 | Ti2O5 | 123.61 |
| 168 | SiO2 | 215.56 |
| 169 | Ti2O5 | 124.16 |
| 170 | SiO2 | 215.84 |
| 171 | Ti2O5 | 124.05 |
| 172 | SiO2 | 213.33 |
| 173 | Ti2O5 | 123.76 |
| 174 | SiO2 | 212.14 |
| 175 | Ti2O5 | 125.08 |
| 176 | SiO2 | 212.08 |
| 177 | Ti2O5 | 126.39 |
| 178 | SiO2 | 213.29 |
| 179 | Ti2O5 | 128.31 |
| 180 | SiO2 | 215.71 |
| 181 | Ti2O5 | 128.69 |
| 182 | SiO2 | 212.95 |
| 183 | Ti2O5 | 129.07 |
| 184 | SiO2 | 216.23 |
| 185 | Ti2O5 | 129.24 |
| 186 | SiO2 | 106.98 |

APPENDIX G

Quadruple-notch Filter Example

| Layer # | Material | Metric Thickness (nm) |
|---|---|---|
| Side 1 Coating (triple-notch filter coating): Total number of layers = 152 Total thickness = 19.40648 micrometers ||| 
| 1 | Nb2O5 | 101.92 |
| 2 | SiO2 | 162.5 |
| 3 | Nb2O5 | 92.46 |
| 4 | SiO2 | 156.76 |
| 5 | Nb2O5 | 91.04 |
| 6 | SiO2 | 153.88 |
| 7 | Nb2O5 | 199.39 |
| 8 | SiO2 | 170.78 |
| 9 | Nb2O5 | 87.39 |
| 10 | SiO2 | 150.74 |
| 11 | Nb2O5 | 100.5 |
| 12 | SiO2 | 124.45 |
| 13 | Nb2O5 | 85.14 |
| 14 | SiO2 | 142.78 |
| 15 | Nb2O5 | 88.34 |
| 16 | SiO2 | 148.85 |
| 17 | Nb2O5 | 101.38 |
| 18 | SiO2 | 185.73 |
| 19 | Nb2O5 | 194.95 |
| 20 | SiO2 | 189.19 |
| 21 | Nb2O5 | 97.25 |
| 22 | SiO2 | 184.79 |
| 23 | Nb2O5 | 98.53 |

APPENDIX G-continued

Quadruple-notch Filter Example

| Layer # | Material | Metric Thickness (nm) |
|---|---|---|
| 24 | SiO2 | 336.62 |
| 25 | Nb2O5 | 101.18 |
| 26 | SiO2 | 143.35 |
| 27 | Nb2O5 | 89.86 |
| 28 | SiO2 | 194.69 |
| 29 | Nb2O5 | 191.09 |
| 30 | SiO2 | 178.48 |
| 31 | Nb2O5 | 83.11 |
| 32 | SiO2 | 126.39 |
| 33 | Nb2O5 | 100.86 |
| 34 | SiO2 | 175.48 |
| 35 | Nb2O5 | 119.67 |
| 36 | SiO2 | 40 |
| 37 | Nb2O5 | 121.17 |
| 38 | SiO2 | 140.9 |
| 39 | Nb2O5 | 80.77 |
| 40 | SiO2 | 195.29 |
| 41 | Nb2O5 | 80.27 |
| 42 | SiO2 | 146.36 |
| 43 | Nb2O5 | 95.81 |
| 44 | SiO2 | 116.65 |
| 45 | Nb2O5 | 84.42 |
| 46 | SiO2 | 156.08 |
| 47 | Nb2O5 | 109.8 |
| 48 | SiO2 | 147.36 |
| 49 | Nb2O5 | 71.34 |
| 50 | SiO2 | 158.05 |
| 51 | Nb2O5 | 97.78 |
| 52 | SiO2 | 54.35 |
| 53 | Nb2O5 | 96.24 |
| 54 | SiO2 | 189.42 |
| 55 | Nb2O5 | 83.79 |
| 56 | SiO2 | 147.78 |
| 57 | Nb2O5 | 89.43 |
| 58 | SiO2 | 116.73 |
| 59 | Nb2O5 | 87.44 |
| 60 | SiO2 | 118.84 |
| 61 | Nb2O5 | 91.55 |
| 62 | SiO2 | 183.51 |
| 63 | Nh2O5 | 72.48 |
| 64 | SiO2 | 155.62 |
| 65 | Nb2O5 | 101.34 |
| 66 | SiO2 | 102.32 |
| 67 | Nb2O5 | 175.64 |
| 68 | SiO2 | 161.6 |
| 69 | Nb2O5 | 101.38 |
| 70 | SiO2 | 190.1 |
| 71 | Nh2O5 | 109.54 |
| 72 | SiO2 | 138.02 |
| 73 | Nb2O5 | 83.95 |
| 74 | SiO2 | 201.74 |
| 75 | Nb2O5 | 76.68 |
| 76 | SiO2 | 151.87 |
| 77 | Nb2O5 | 96.69 |
| 78 | SiO2 | 104.51 |
| 79 | Nb2O5 | 71.13 |
| 80 | SiO2 | 143.51 |
| 81 | Nb2O5 | 93.38 |
| 82 | SiO2 | 159.31 |
| 83 | Nb2O5 | 92.66 |
| 84 | SiO2 | 134.29 |
| 85 | Nb2O5 | 109.58 |
| 86 | SiO2 | 64.3 |
| 87 | Nb2O5 | 95.83 |
| 88 | SiO2 | 80.61 |
| 89 | Nb2O5 | 121.17 |
| 90 | SiO2 | 158.16 |
| 91 | Nb2O5 | 126.18 |
| 92 | SiO2 | 304.12 |
| 93 | Nb2O5 | 91.08 |
| 94 | SiO2 | 142.31 |
| 95 | Nb2O5 | 116.44 |
| 96 | SiO2 | 142.9 |
| 97 | Nb2O5 | 102.19 |
| 98 | SiO2 | 155.26 |
| 99 | Nb2O5 | 42.77 |
| 100 | SiO2 | 117.74 |
| 101 | Nb2O5 | 96.83 |
| 102 | SiO2 | 157.4 |
| 103 | Nb2O5 | 80.23 |
| 104 | SiO2 | 170.92 |
| 105 | Nb2O5 | 80.26 |
| 106 | SiO2 | 152.18 |
| 107 | Nb2O5 | 59.5 |
| 108 | SiO2 | 150.8 |
| 109 | Nb2O5 | 55.05 |
| 110 | SiO2 | 179.98 |
| 111 | Nb2O5 | 72.95 |
| 112 | SiO2 | 147.86 |
| 113 | Nb2O5 | 113.24 |
| 114 | SiO2 | 113.94 |
| 115 | Nb2O5 | 75.53 |
| 116 | SiO2 | 148.34 |
| 117 | Nb2O5 | 86.68 |
| 118 | SiO2 | 151.37 |
| 119 | Nb2O5 | 112.12 |
| 120 | SiO2 | 187.87 |
| 121 | Nb2O5 | 173.08 |
| 122 | SiO2 | 142.73 |
| 123 | Nh2O5 | 111.37 |
| 124 | SiO2 | 130.1 |
| 125 | Nb2O5 | 111.36 |
| 126 | SiO2 | 169.22 |
| 127 | Nb2O5 | 40.48 |
| 128 | SiO2 | 165.45 |
| 129 | Nb2O5 | 80.24 |
| 130 | SiO2 | 152.88 |
| 131 | Nb2O5 | 93.66 |
| 132 | SiO2 | 142.15 |
| 133 | Nb2O5 | 101.36 |
| 134 | SiO2 | 139.3 |
| 135 | Nb2O5 | 68.39 |
| 136 | SiO2 | 169.49 |
| 137 | Nb2O5 | 103.48 |
| 138 | SiO2 | 375.72 |
| 139 | Nb2O5 | 104.58 |
| 140 | SiO2 | 334.56 |
| 141 | Nb2O5 | 109.17 |
| 142 | SiO2 | 145.03 |
| 143 | Nb2O5 | 90.92 |
| 144 | SiO2 | 154.29 |
| 145 | Nb2O5 | 78.49 |
| 146 | SiO2 | 140.27 |
| 147 | Nb2O5 | 92.97 |
| 148 | SiO2 | 144.86 |
| 149 | Nb2O5 | 93.92 |
| 150 | SiO2 | 153.94 |
| 151 | Nb2O5 | 88.36 |
| 152 | SiO2 | 72.56 |

Side 2 Coating (long-wave-pass filter coating):
Total number of layers = 62
Total thickness = 2.94689 micrometers

| Layer # | Material | Metric Thickness (nm) |
|---|---|---|
| 1 | Nb2O5 | 20.02 |
| 2 | SiO2 | 50.32 |
| 3 | Nb2O5 | 35.28 |
| 4 | SiO2 | 54.08 |
| 5 | Nb2O5 | 31.38 |
| 6 | SiO2 | 62.56 |
| 7 | Nb2O5 | 34.52 |
| 8 | SiO2 | 56.07 |
| 9 | Nb2O5 | 34.68 |
| 10 | SiO2 | 62.44 |
| 11 | Nb2O5 | 33.45 |
| 12 | SiO2 | 58.99 |
| 13 | Nb2O5 | 35.4 |
| 14 | SiO2 | 60.77 |
| 15 | Nb2O5 | 33.56 |
| 16 | SiO2 | 60.87 |
| 17 | Nb2O5 | 34.43 |

APPENDIX G-continued

Quadruple-notch Filter Example

| Layer # | Material | Metric Thickness (nm) |
|---|---|---|
| 18 | SiO2 | 60.55 |
| 19 | Nb2O5 | 34.81 |
| 20 | SiO2 | 60.22 |
| 21 | Nb2O5 | 34.69 |
| 22 | SiO2 | 61.21 |
| 23 | Nb2O5 | 34.13 |
| 24 | SiO2 | 61.26 |
| 25 | Nb2O5 | 34.84 |
| 26 | SiO2 | 59.87 |
| 27 | Nb2O5 | 34.51 |
| 28 | SiO2 | 61.73 |
| 29 | Nb2O5 | 34.78 |
| 30 | SiO2 | 59.61 |
| 31 | Nb2O5 | 34.7 |
| 32 | SiO2 | 62.29 |
| 33 | Nb2O5 | 34.39 |
| 34 | SiO2 | 59.12 |
| 35 | Nb2O5 | 35.16 |
| 36 | SiO2 | 62.52 |
| 37 | Nb2O5 | 33.71 |
| 38 | SiO2 | 59.14 |
| 39 | Nb2O5 | 35.78 |
| 40 | SiO2 | 62.24 |
| 41 | Nb2O5 | 32.88 |
| 42 | SiO2 | 59.83 |
| 43 | Nb2O5 | 36.47 |
| 44 | SiO2 | 61.3 |
| 45 | Nb2O5 | 32.22 |
| 46 | SiO2 | 62.34 |
| 47 | Nb2O5 | 36.1 |
| 48 | SiO2 | 58.96 |
| 49 | Nb2O5 | 33.41 |
| 50 | SiO2 | 62.89 |
| 51 | Nb2O5 | 35.17 |
| 52 | SiO2 | 57.13 |
| 53 | Nb2O5 | 34.31 |
| 54 | SiO2 | 62.12 |
| 55 | Nb2O5 | 35.25 |
| 56 | SiO2 | 54.53 |
| 57 | Nb2O5 | 33.72 |
| 58 | SiO2 | 65.6 |
| 59 | Nb2O5 | 32.81 |
| 60 | SiO2 | 44.44 |
| 61 | Nb2O5 | 37.87 |
| 62 | SiO2 | 107.46 |

What is claimed is:

1. A method for depositing a layer of material onto a substrate in order to manufacture a notch filter, the method comprising the steps of:

calculating, with a data processor, a theoretical transmission $T_i$ of light through the layer;

calculating, with the data processor, an expected deposition time $t_i$ of the layer;

measuring, during deposition of the layer for a period less than $t_i$, a measured transmission $T_m$ of light through the layer; and determining, with the data processor, when deposition of the layer is to terminate based upon the theoretical transmission $T_i$ and the measured transmission $T_m$.

2. The method of claim 1, wherein calculating $T_i$ calculates $T_i$ based upon a desired thickness d of the layer at a series of wavelengths, thereby generating a series of curves $T_i$ vs. d at each of the series of wavelengths, wherein measuring $T_m$ measures $T_m$ as a function of actual times transpired t, thereby generating a curve $T_m$ vs. t, and wherein the method further comprises:

determining an optical monitoring wavelength lm based upon the series of curves $T_i$ vs. d, thereby selecting a single curve $T_i$ vs. d at λm from the series of curves; and converting the single curve $T_i$ vs. d at λm to $T_i$ vs. t using the equation t=d/r, where r is a known deposition rate for the layer, wherein determining when deposition of the layer is to terminate comprises:

calculating a deposition rate rci by minimizing an error between the curve $T_i$ vs. t and the curve $T_m$ vs. t, the minimizing occurring by varying parameters pertaining to the curve $T_i$ vs. t; and determining when deposition of the layer is to terminate based upon the calculated deposition rate rci or a deposition rate derived therefrom.

3. The method of claim 2, wherein the notch filter is a single-sided-coating notch filter.

4. The method of claim 2, wherein the notch filter is a single-notch filter or a multi-notch filter.

5. A notch filter comprising a transparent substrate having a first surface, wherein a plurality of layers of alternating higher- and lower-index-of-refraction material are disposed overlying the first surface, and wherein at least one of the layers is formed by the method of claim 1.

6. An optical analysis system for exciting a sample of material with light of a first wavelength to produce a measurable or viewable optical response at a second wavelength different from the first, the system comprising a source of excitation light, an optical path coupling the excitation light to the sample, an optical path coupling light from the sample to an analyzer or viewer, and a filter in the path between the sample and the analyzer or viewer for blocking some light other than the optical response at the second wavelength, wherein the filter is an optical notch filter comprising a layer made by the method of claim 1.

7. The optical analysis system of claim 6, wherein the optical analysis system is a fluorescence measurement system.

8. The optical analysis system of claim 6, wherein the optical analysis system is a Raman spectroscopy system.

9. A method for making a notch filter using an apparatus, the filter designed to have N layers, and the method comprising the steps of:

calculating, with a data processor, theoretical transmission data for each layer;

determining, with the data processor, which of the N layers are to be optically monitored;

calculating an expected deposition time for a current layer being deposited based upon a designed thickness of the layer and a deposition rate of the apparatus for the layer, the current layer being one of the N layers;

measuring, during deposition of the current layer for a time less than the expected deposition time, measured transmission data for the current layer, if the current layer is determined to be an optically monitored layer;

determining, with the data processor, when deposition of the current layer is to terminate based upon the theoretical transmission data and the measured transmission data, if the current layer is determined to be an optically monitored layer; and determining, with the data processor, when deposition of the current layer is to terminate based upon expiration of the expected deposition duration, if the current layer is not determined to be an optically monitored layer.

10. The method of claim 9 wherein determining which of the N layers are to be optically monitored comprises:
   adding noise to the theoretical transmission data, thereby generating estimated actual transmission data;
   simulating deposition of the N layers using the theoretical transmission data and the estimated actual transmission data, the simulating producing a simulated thickness for each layer;
   calculating an error between the simulated thickness and the designed thickness for each layer;
   selecting layers that have an error below a threshold as layers to be optically monitored.

11. The method of claim 10, wherein the notch filter is a single-sided-coating notch filter.

12. The method of claim 10, wherein the notch filter is a single-notch filter or a multi-notch filter.

13. The method of claim 10, wherein the notch filter is a dual-sided-coating notch filter.

14. A notch filter comprising a transparent substrate having a first surface, wherein a plurality of layers of alternating higher- and lower-index-of-refraction material are disposed overlying the first surface, and wherein the layers are formed by the method of Claim 9.

15. The notch filter of claim 14, wherein the layers form a single-notch coating.

16. The notch filter of claim 14, wherein the layers form a multi-notch coating.

17. The notch filter of claim 14, wherein the substrate has a second surface, wherein the notch filter further comprises a plurality of layers of alternating higher- and lower-index-of-refraction material disposed overlying the second surface, and wherein the layers disposed overlying the second surface are formed by the method of claim 9.

18. The notch filter of claim 17, wherein the layers disposed overlying the second surface form a long-wave-pass-filter coating.

19. An optical analysis system for exciting a sample of material with light of a first wavelength to produce a measurable or viewable optical response at a second wavelength different from the first, the system comprising a source of excitation light, an optical path coupling the excitation light to the sample, an optical path coupling light from the sample to an analyzer or viewer, and a filter in the path between the sample and the analyzer or viewer for blocking some light other than the optical response at the second wavelength,
   wherein the filter is an optical notch filter comprising a layer made by the method of claim 9.

20. The optical analysis system of claim 19, wherein the optical analysis system is a fluorescence measurement system.

21. The optical analysis system of claim 19, wherein the optical analysis system is a Raman spectroscopy system.

22. A multi-layer, thin-film optical filter that blocks light at a particular wavelength ($\lambda_L$) with an optical density greater than 6, wherein the filter exhibits transmission greater than 90% and less than or equal to approximately 100% at wavelengths that are greater than or equal to $\lambda_L$+1.3 (Notch Bandwidth) and less than or equal to $\lambda_L$−1.3(Notch Bandwidth) and wherein Notch Bandwidth ("NBW") is defined as:

$$NBW = 55 \times 10^{-6} \times \lambda_L^2 + 14 \times 10^{-3} \times \lambda_L - 5.9, \text{ and}$$

wherein NBW and $\lambda_L$ are in units of nm.

23. The multi-layer, thin-film optical filter of claim 22, wherein the multi-layer, thin-film optical filter includes a hard coating.

24. The multi-layer, thin film optical filter of claim 22, wherein a spectral feature of the filter shifts less than approximately 0.0005% per degree Celsius and greater than or equal to approximately 0.00005% per degree Celsius.

25. The multi-layer, thin film optical filter of claim 24, wherein the spectral feature is a wavelength at which 50% transmission occurs.

26. The multi-layer, thin film optical filter of claim 24, wherein the spectral feature is a wavelength at which the filter achieves a maximum optical density.

27. The multi-layer, thin film optical filter of claim 22, wherein a laser damage threshold of the filter exceeds 1 Joule/cm$^2$ of pulse energy in a pulse of approximate duration of 10 ns, wherein the laser damage threshold is associated with a laser wavelength approximately equal to a design laser wavelength, and wherein the laser damage threshold is within a notch bandwidth.

28. The multi-layer, thin film optical filter of claim 22, wherein the optical filter is a multi-notch filter.

29. The multi-layer, thin film optical filter of claim 22, wherein the optical filter is a dual-notch filter.

30. The multi-layer, thin film optical filter of claim 22, wherein the optical filter is a triple-notch filter.

31. The multi-layer, thin film optical filter of claim 22, wherein the optical filter is a quadruple-notch filter.

32. The multi-layer, thin film optical filter of claim 22, wherein the optical filter comprises a substrate, a multi-notch coating on a first side of the substrate, and a long-wave-pass filter coating on a second side of the substrate.

33. The multi-layer, thin-film optical filter of Claim 22, wherein the optical filter comprises a substrate, a first multi-notch coating on a first side of the substrate, and a second multi-notch coating on a second side of the substrate.

34. The multi-layer, thin-film optical filter of claim 22, wherein the light is blocked via reflection.

35. An optical analysis system for exciting a sample of material with light of a first wavelength to produce a measurable or viewable optical response at a second wavelength different from the first, the system comprising a source of excitation light, an optical path coupling the excitation light to the sample, an optical path coupling light from the sample to an analyzer or viewer, and a filter in the path between the sample and the analyzer or viewer for blocking some light other than the optical response at the second wavelength,
   wherein the filter is a multi-layer, thin film optical filter according to claim 22.

36. The optical analysis system of claim 35, wherein the optical analysis system is a fluorescence measurement system.

37. The optical analysis system of claim 35, wherein the optical analysis system is a Raman spectroscopy system.

38. A multi-layer, thin-film optical filter that blocks light at a particular wavelength ($\lambda_L$) with an optical density greater than 6, wherein the filter exhibits transmission greater than 90% and less than or equal to approximately 100% at wavelength between ($\lambda_L$+0.65(NBW)) and $\lambda_L$/0.75, and between 0.75($\lambda_L$) and ($\lambda_L$−0.65(NBW)), and wherein NBW is defined as:

$$NBW = 55 \times 10^{-6} \times \lambda_L^2 + 14 \times 10^{-3} \times \lambda_L - 5.9, \text{ and}$$

wherein NBW and $\lambda_L$ are in units of nm.

39. A multi-layer, in-film optical filter that blocks light at a particular wavelength ($\lambda_L$) with an optical density greater than 6, wherein the filter exhibits transmission greater than 90% and less than or equal to approximately 100% at wavelengths between $(\lambda_L+1.3(NBW))$ and $\lambda_L/0.75$, and between $0.75(\lambda_L)$ and $(\lambda_L-1.3(NBW))$, and wherein NBW is defined as:

$$NBW = 55 \times 10^{-6} \times \lambda_L^2 + 14 \times 10^{-3} \times \lambda_L - 5.9, \text{ and}$$

wherein NBW and $\lambda_L$ are in units of nm.

40. A multi-layer, thin-film optical filter that blocks light at a particular wavelength $(\lambda_L)$ with an optical density greater than 6, wherein the filter exhibits transmission greater than 90% and less than or equal to approximately 100% at wavelengths that are greater than or equal to $\lambda_L+0.65(NBW)$, and less than or equal to $\lambda_L-0.65(NBW)$, and wherein NBW is defined as:

$$NBW = 55 \times 10^{-6} \times \lambda_L^2 + 14 \times 10^{-3} \times \lambda_L - 5.9, \text{ and}$$

wherein NBW and $\lambda_L$ are in units of mm.

41. A multi-layer, thin-film optical filter that, when operated at an angle of incidence of approximately 45 degrees, blocks light of all polarizations at a particular wavelength $(\lambda_L)$ with an optical density greater than 5 and exhibits transmission greater than 90% and less than or equal to approximately 100% at wavelengths that are greater than or equal to $\lambda_L+1.3(NBW)$ and less than or equal to $\lambda_L-1.3(NBW)$, wherein NBW is defined as:

$$NBW = 55 \times 10^{-6} \times \lambda_L^2 + 14 \times 10^{-3} \times \lambda_L - 5.9, \text{ and}$$

wherein NBW and $\lambda_L$ are in units of nm.

42. The multi-layer, thin-film optical filter of claim 41, wherein the multi-layer, thin-film optical filter exhibits very efficient beamsplitting.

43. An optical analysis system for exciting a sample of material with light of a fist wavelength to produce a measurable or viewable optical response at a second wavelength different from the first, the system comprising a source of excitation light, an optical path coupling the excitation light to the sample, an optical path coupling light from the sample to an analyzer or viewer, and a filter in the path between the sample and the analyzer or viewer for blocking some light other than the optical response at the second wavelength, wherein the filter is a multi-layer, thin film optical filter according to claim 42.

44. The optical analysis system of claim 43, wherein the optical analysis system is fluorescence measurement system.

45. The optical analysis system of claim 43, wherein the optical analysis system is a Raman spectroscopy system.

46. The multi-layer, thin-film optical filter of claim 41, wherein, when operated at an angle of incidence of approximately 45 degrees, the filter exhibits transmission greater than 90% and less than or equal to approximately 100% at wavelengths between $(\lambda^L+1.3(NBW))$ and $\lambda_L/0.75$, and between $0.75(\lambda_L)$ and $(\lambda_L-1.3(NBW))$, wherein NBW is defined as:

$$NBW = 55 \times 10^{-6} \times \lambda_L^2 + 14 \times 10^{-3} \times \lambda_L - 5.9, \text{ and}$$

wherein NBW and $\lambda_L$ are in units of nm.

47. The multi-layer, thin-film optical filter of claim 41, a spectral feature of the filter shifts less than approximately 0.0005% per degree Celsius and greater than or equal to approximately 0.00005% per degree Celsius.

48. The multi-layer, thin-film optical filter of claim 47, wherein the spectral feature is a wavelength at which 50% transmission occurs.

49. The multi-layer, thin-film optical filter of claim 47, wherein the spectral feature is a wavelength at which the filter achieves a maximum optical density.

50. The multi-layer, thin-film optical filter of claim 44, wherein a laser damage threshold of the filter exceeds 1 Joule/cm$^2$ of pulse energy in a pulse of approximate duration of 10 ns, wherein the laser damage threshold is associated with a laser wavelength approximately equal to a design laser wavelength, and wherein the laser damage threshold is within a notch bandwidth.

51. An optical analysis system for exciting a sample of material with light of a first waelength to produce a measurable or viewable optical response at a second wavelength diffrent from the first, the system comprising a source of excitation light, an optical path coupling the excitation light to the sample, an optical path coupling light from the sample to an analyzer or viewer, and a filter in the path between the sample and the analyzer or viewer for blocking some light other than the optical response at the second wavelength.

52. The optical analysis system of claim 51, wherein the optical analysis system is a fluorescence measurement system.

53. The optical analysis system of claim 51, wherein the optical analysis system is a Raman spectroscopy system.

* * * * *

(12) EX PARTE REEXAMINATION CERTIFICATE (7885th)
United States Patent
Erdogan et al.

(10) Number: US 7,123,416 C1
(45) Certificate Issued: *Nov. 23, 2010

(54) METHOD OF MAKING HIGH PERFORMANCE OPTICAL EDGE AND NOTCH FILTERS AND RESULTING PRODUCTS

(75) Inventors: Turan Erdogan, Spencerport, NY (US); Joseph T. Foss, Rochester, NY (US); Ligang Wang, Rochester, NY (US)

(73) Assignee: Semrock, Inc., Rochester, NY (US)

Reexamination Request:
No. 90/010,880, Feb. 26, 2010

Reexamination Certificate for:
Patent No.: 7,123,416
Issued: Oct. 17, 2006
Appl. No.: 11/248,456
Filed: Oct. 11, 2005

(*) Notice: This patent is subject to a terminal disclaimer.

Related U.S. Application Data

(63) Continuation-in-part of application No. 10/840,134, filed on May 6, 2004, now Pat. No. 7,068,430.
(60) Provisional application No. 60/468,245, filed on May 6, 2003, and provisional application No. 60/637,697, filed on Dec. 21, 2004.

(51) Int. Cl.
*G02B 5/28* (2006.01)
*G02B 1/10* (2006.01)

(52) U.S. Cl. .................. 359/589; 359/580; 359/587; 359/588

(58) Field of Classification Search .................. None
See application file for complete search history.

(56) References Cited
U.S. PATENT DOCUMENTS

| | | |
|---|---|---|
| 5,216,542 A | 6/1993 | Szczyrbowski et al. |
| 5,272,518 A | 12/1993 | Vincent |
| 5,828,489 A | 10/1998 | Johnson |
| 6,110,337 A | 8/2000 | Sullivan et al. |
| 6,217,720 B1 | 4/2001 | Sullivan et al. |
| 6,641,704 B2 | 11/2003 | Someno |
| 7,068,430 B1 | 6/2006 | Clarke et al. |
| 7,119,960 B1 | 10/2006 | Erdogan et al. |
| 2005/0167264 A1 | 8/2005 | Sternbergh et al. |

OTHER PUBLICATIONS

R.L. Hall, et al., "The Fabrication of Rugate Filters Using the Digital Technique," Optical Interference Coatings, Technical Digest Series, vol. 6, (Optical Society of America, Washington, DC 1988), pp. TuF10-1-TuF10-4 (4 pages).
Cover page and Table of Contents of vol. 1 of 3 of the Technical Program Proceedings of NFOEC 2001, Tuesday Jul. 10, 2001, pp. v-x (7 pages).
Cover page and Table of Contents of vol. 2 of 3 of the Technical Program Proceedings of NFOEC 2001, Wednesday Jul. 11, 2001, pp. v-x (7 pages).
Cover page and Table of Contents of vol. 3 of 3 of the Technical Program Proceedings of NFOEC 2001, Thursday Jul. 12, 2001, pp. v-xi (8 pages).

(Continued)

*Primary Examiner*—James Menefee

(57) ABSTRACT

High performance optical edge and notch filters and methods of making the same are disclosed. The multi-layer, thin-film optical edge filters have an edge steepness greater than about 0.8% as measured by dividing (a) the edge width from the 50% transmission wavelength to the optical density 6 ("OD6") wavelength by (b) the 50% transmission wavelength. The optical edge filters also have an average transmission above about 95%. The notch filters exhibit a blocking of OD>6, very high transmission (>90%) outside the notch(es), and a narrow notch bandwidth comparable to that of holographic notch filters. The methods for making such filters accurately determine when deposition of each layer of the filter should terminate.

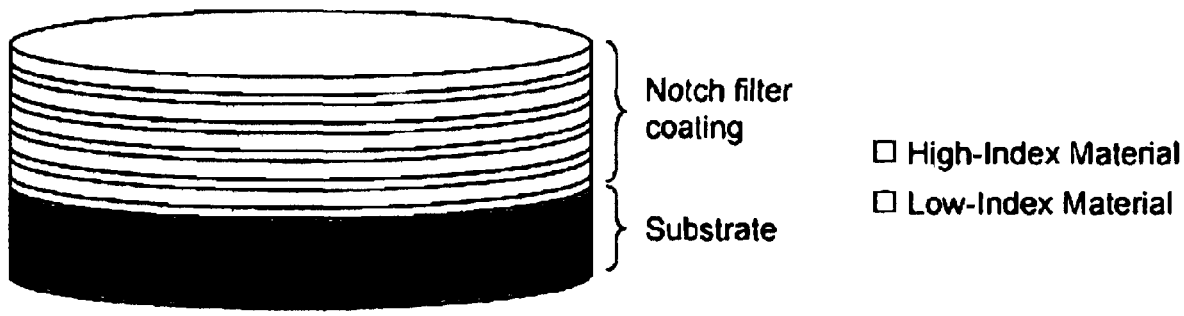

OTHER PUBLICATIONS

R. Fortenberry, et al., "Optical Filter Dispersion in 40 Gb/s DWDM Transmission Systems" in vol. 2 of 3 of the Technical Program Proceedings of NFOEC 2001, Jul. 11, 2001, pp. 670–677 (8 pages).

R. Fortenberry, et al., "NFOEC 2001 Optical Filter Dispersion in 40 Gb/s DWDM Transmission Systems", Captioned: "Cierra Photonics, Inc." (16 pages, dated "Jun. 22, 2001").

SH. A. Furman, et al., "Chapter 1 Spectral Characteristics of Multilayer Coatings; Theory" from *Basics of Optics of Multilayer Systems*, Edition Frontieres, Gif–Sur–Yvette (1992), pp. 1–103 (104 pages total).

T.R. Jensen, et al., "Environmentally Stable UV Raman Edge Filters", Society of Vacuum Coaters 43rd Annual Technical Conference Proceedings (2000) pp. 1–5 (5 pages).

G. Lenz, et al., "Dispersive Properties of Optical Filters for WDM Systems," IEEE Journal of Quantum Electronics, Aug. 1998, vol. 34, No. 8, pp. 1390–1402 (13 pages).

H.A. Macleod "Thin–Film Optical Coating Design", from *Thin Films for Optical Systems*, F.R. Flory, ed., Marcel Dekker, Inc., 1995, pp. 17–19, 30–32 (7 pages).

H.A. Macleod, *Thin–Film Optical Filters*, Third Edition, Taylor & Francis, NY, 2001, pp. vii–xi, 20–35, 46–50, 190–200, 210–267 (97 pages total).

Omega Optical Inc., "Precision Interference Filters," (3 page document, 1998 copyright) (4 pages total).

Robert B. Sargent, et al., "Review of Thin Films in Telecommunications Applications", Optical Interference Coatings (OIC) 2001, Banff, Canada, OIC Proc. Telecommunication Filters I (WA), p. WA2–1–WA2–3 (Jul. 15, 2001) (3 pages).

M.A. Scobey, et al. "Improved Temperature and Humidity Stability of Ultra–Narrow Band Filters" Society of Vacuum Coaters 37th Annual Technical Conference Proceedings (1994) pp. 47–52 (6 pages).

Software Spectra, "Summary of TFCalc features", web.archive.org/web/20020204022003635/www.sspectra.com, (3 pages).

Thin Film Center, Inc. "The Concise Macleod," web.archive.org/web/20020205061111/www.thinfilmcenter.com (3 pages).

R.–Y. Tsai, et al., "Comparative Study of Ultraviolet–Infrared Cutoff Filters Prepared by Reactive Electron–Beam Deposition and Reactive Ion–Assisted Deposition", Opt. Eng., May 1998, pp. 1475–1481 (7 pages).

Robert Q. Fugate, "Prospects for benefits to astronomical adaptive optics from US military programs," Procedings of SPIE vol. 4007 (2000) p. 422–429.

H. Hagedorn, A. Lotz, P. Pecher, and O. Treichel, "Ultra narrow band pass filters produced by plasma ion assisted deposition," in Optical Interference Coatings, OSA Technical Digest Series (Optical Society of America, 2001), paper WA4.

Fornier, High laser damage threshold HfO2/SiO2 mirrors manufactured by sputtering process, Proceedings of the SPIE, the International Society for Optical Engineering (1999).

Walter E. Johnson and Robert L. Crane, "Introduction to rugate filter technology," in Inhomogeneous and Quasi–Inhomogeneous Optical Coatings, Jerzy A. Dobrowolski, Pierre G. Verly, Editors, Proc. SPIE 2046, p. 88–108 (1993).

H. A. Macleod, Thin Film Optical Filters, 3rd Edition, MacMillan Publishing Co., NY (2001).

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 22-32, 34, 38-42 and 46-49 is confirmed.

Claims 1-21, 33, 35-37, 43-45 and 50-53 were not reexamined.

\* \* \* \* \*